(12) United States Patent
Bergan et al.

(10) Patent No.: US 8,742,141 B2
(45) Date of Patent: *Jun. 3, 2014

(54) INHIBITION AND TREATMENT OF PROSTATE CANCER METASTASIS

(71) Applicant: Northwestern University, Evanston, IL (US)

(72) Inventors: Raymond C. Bergan, Chicago, IL (US); Karl A. Scheidt, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/932,300

(22) Filed: Jul. 1, 2013

(65) Prior Publication Data

US 2013/0296582 A1     Nov. 7, 2013

Related U.S. Application Data

(63) Continuation of application No. 12/578,137, filed on Oct. 13, 2009, now Pat. No. 8,481,760.

(60) Provisional application No. 61/104,564, filed on Oct. 10, 2008.

(51) Int. Cl.
    *C07D 311/00*    (2006.01)
    *A61K 31/35*    (2006.01)

(52) U.S. Cl.
    USPC .......................................... 549/403; 514/456

(58) Field of Classification Search
    USPC .......................................... 549/403; 514/456
    See application file for complete search history.

(56) References Cited

U.S. PATENT DOCUMENTS

| 3,687,808 | A | 8/1972 | Merigan, Jr. |
| 4,312,806 | A | 1/1982 | Lambert |
| 4,816,567 | A | 3/1989 | Cabilly |
| 5,034,506 | A | 7/1991 | Summerton |
| 5,216,002 | A | 6/1993 | Gidda |
| 5,238,931 | A | 8/1993 | Yoshikawa |
| 5,270,163 | A | 12/1993 | Gold |
| 5,294,630 | A | 3/1994 | Blake |
| 5,368,854 | A | 11/1994 | Rennick |
| 5,391,555 | A | 2/1995 | Marshall |
| 5,489,677 | A | 2/1996 | Sanghvi |
| 5,506,213 | A | 4/1996 | Carson |
| 5,539,082 | A | 7/1996 | Nielsen |
| 5,552,439 | A | 9/1996 | Panetta |
| 5,567,588 | A | 10/1996 | Gold |
| 5,569,680 | A | 10/1996 | Wu |
| 5,595,877 | A | 1/1997 | Gold |
| 5,602,240 | A | 2/1997 | De Mesmaeker |
| 5,660,985 | A | 8/1997 | Pieken |
| 5,696,249 | A | 12/1997 | Gold |
| 5,714,331 | A | 2/1998 | Buchardt |
| 5,719,262 | A | 2/1998 | Buchardt |
| 5,756,449 | A | 5/1998 | Andersen |
| 5,763,177 | A | 6/1998 | Gold |
| 5,792,795 | A | 8/1998 | Buser |
| 5,817,785 | A | 10/1998 | Gold |
| 5,834,021 | A | 11/1998 | Speirs |
| 5,888,969 | A | 3/1999 | Girten |
| 5,889,028 | A | 3/1999 | Sandborn |
| 5,911,995 | A | 6/1999 | Uckun ..................... 424/195.11 |
| 5,932,214 | A | 8/1999 | Lobb |
| 5,998,596 | A | 12/1999 | Bergan |
| 6,001,577 | A | 12/1999 | Gold |
| 6,028,088 | A | 2/2000 | Pershadsingh |
| 6,046,231 | A | 4/2000 | Kosmeder |
| 6,184,364 | B1 | 2/2001 | Pieken |
| 6,344,318 | B1 | 2/2002 | Gold |
| 6,376,190 | B1 | 4/2002 | Gold |
| 6,482,594 | B2 | 11/2002 | Gold |
| 6,506,559 | B1 | 1/2003 | Fire et al. |
| 6,677,350 | B1 | 1/2004 | Lin |
| 2004/0147551 | A1 | 7/2004 | Heaton |
| 2005/0049424 | A1 | 3/2005 | Kelly |
| 2008/0014249 | A1 | 1/2008 | Heaton et al. ................. 424/439 |

FOREIGN PATENT DOCUMENTS

| JP | 07-330600 A | 12/1995 |
| WO | 00/66576 | 11/2000 |
| WO | 01/26668 | 4/2001 |
| WO | 01/27160 A1 | 4/2001 |
| WO | 03/070966 A2 | 8/2003 |
| WO | 2005/038054 A1 | 4/2005 |
| WO | 2005/049008 | 6/2005 |
| WO | 2005/054270 | 6/2005 |
| WO | 2007/126871 | 8/2007 |

OTHER PUBLICATIONS

Lima et al. (Current Medicinal Chemistry, (2005, 12, 23-49).
Devere White, et al., "Effects of a Genistein-Rich Extract on PSA Levels in Men with a History of Prostate Cancer," Urology (2004), vol. 63, pp. 259-263.
Ghafar, et al., "Regression of Prostate Cancer Following Administration of Genistein Combined Polysaccharide (GCPtm), a Nutritional Supplement: A Case Report," The Journal of Alternative and Complementary Medicine (2002), vol. 8, No. 4, pp. 493-497.
Hillman, et al. "Genistein potentiates inhibition of tumor growth by radiation in a prostate cancer orthotopic model," Molecular Cancer Therapeutics (2004), vol. 3, No. 10, pp. 1271-1279.
Miltyk, et al., "Lack of significant genotoxicity of purified soy isoflavones (genistein, daidzein, and glycitein) in 20 patients with prostate cancer 1-3", Am. J. Clin. Nutr. (2003), vol. 77, pp. 875-882.
Rice, et al., "Mechanisms of the Growth Inhibitory Effects of the Isoflavonoid Biochanin A on LNCaP Cells and Xenografts," The Prostate (2002), vol. 52, pp. 201-212.
Jarred, et al., "Induction of Apoptosis in Low to Moderate-Grade Human Prostate Carcinoma by Red Clover-derived Dietary Isoflavones," Cancer Epidemiology, Biomarkers & Prevention (2002), vol. 11, pp. 1689-1696.

(Continued)

*Primary Examiner* — Shirley V Gembeh
(74) *Attorney, Agent, or Firm* — Casimir Jones SC

(57) ABSTRACT

The present invention provides compounds and methods of inhibiting and treating metastatic prostate cancer. The compounds include MEK4 inhibitors. In another aspect the invention provides methods of identifying inhibitors of metastatic prostate cancer by screening for inhibitors of MEK4.

16 Claims, 41 Drawing Sheets

(56) References Cited

OTHER PUBLICATIONS

Saito et al. (Bulletin of Chemical Society of Japan 46, 1776-1779 (1973)).
Carney et al. Journal of Medicinal Chemistry (1966), 9(4), 516-20.
Godsey et al., 2007, "The 2.2 A resolution crystal structure of a *Bacillus cereus* Nif3-family protein YqfO, revels a conserved dimetal binding motif and a regulatory domain," Protein Science, 16:1285-1293.
Goedert et al., 1997, "Activation of the novel stress-activated protein kinase SAPK4 by cytokines and cellular stresses is mediated by SKK3 (MKK6); comparison of its substrate specificity with that of other SAP kinases," EMBO J. 16:3563-71.
Goodman et al., 2009, "Circulating tumor cells in patients with castration-resistant prostate cancer baseline values and correlation with prognostic factors," Cancer Epidemiol. Biomarkers Prev. 18:1904-1913.
Graves et al., 2006, "Enantioselective MSPV reduction of ketimines using 2-propanol and (BINOL)AI(III)," Org Lett, 8:1229-1232.
Greco et al., 1979, "Evaluation of methods for estimating the dissociation constant of tight binding enzyme inhibitors," J Biol Chem, 254:12104-12109.
Han et al., 2002, "Rac1-MKK3-p38-MAPKAPK2 pathway promotes urokinase plasminogen activator mRNA stability in invasive breast cancer cells," J Biol Chem, 277:48379-48385.
Hanks et al., 1992, "Focal adhesion protein-tyrosine kinase associated with focal adhesions," PNAS, 89:8487-8491.
Hayes et al., 2003, "p38 MAP kinase modulates Smad-dependent changes in human prostate cell adhesion," Oncogene 22:4841-4850.
Heldin et al., 1997, "TGF-beta signaling from cell membrane to nucleus through SMAD proteins," Nature, 390:465-471.
Helo et al., 2009, "Circulating prostate tumor cells detected by reverse transcription-PCR in men with localized or castration-refractory prostate cancer: concordance with CellSearch assay and association with bone metastases and with survival," Clin. Chem., 55:765-773.
Herberich et al., 2008, "Discovery of highly selective and potent p38 inhibitors based on a phthalazine scaffold," J. Med. Chem, 51:6271-6279.
Hoffman et al., 1991, "The effects of heparin cofactor II-derived chemotaxins on neutrophil actin conformation and cyclic AMP levels," Biochim Biophys Acta, 1095: 78-82.
Holen et al., 2002, "Positional effects of short interfering RNAs targeting the human coagulation trigger Tissue Factor," Nucleic Acids Res, 30:1757-66.
Hood and Perlmutter, 2004, "The impact of systems approaches on biological problems in drug discovery," Nat Biotechnol, 22:1215-1217.
Horiuchi et al., 2000, "Effect of soy protein on bone metabolism in postmenopausal Japanes women," Osteoporos Int, 11:721-724.
Hoshino et al., 1988, "Novel Synthesis of Isoflavones by the Palladium-Catalyzed Cross-Coupling Reaction of 3-Bromochromosomes with Arylboronic Acids or Its Esters," Bulletin of the Chemical Society of Japan, 61(8): 3008-10.
Hu et al., 2005,"Validation of the neuroinflammation cycle as a drug discovery target using integrative chemical biology and lead compound development with an Alzheimer's disease-related mouse model," Curr Alzheimer Res, 2:197-205.
Huang et al., 1998, "Synthesis and antiplatelet activity of phenyl quinolones," Biorg. Med. Chem, 6:1657-62.
Huang et al., 2005, "Genistein inhibits p38 map kinase activation, matrix metalloproteinase type 2, and cell invasion in human prostate epithelial cells," Cancer Res. 65:3470-3478.
Humphries, 2001, "Cell adhesion assays," Mol Biotechnol, 18:57-61.
Inoue et al., 2005, "Androgen receptor, Ki67, and p53 expression in radical prostatectomy specimens predict treatment failure in Japanese population," Urology, 66:332-337.
Jackson et al., 1998,"Pharmacological effects of SB 220025, a selective inhibitor of P38 mitogen-activated protein kinase, in angiogenesis and chronic inflammatory disease models." J. Pharmacol. Exp Ther, 284:687-92.
Jemal et al., 2007, "Cancer statistics" CA Cancer J Clin, 57:43-66.
Ji et al., 2003, "MALAT-1, a novel noncoding RNA, and thymosin beta4 predict metastasis and survival in early-stage non small cell lung cancer," Oncogene 22:8031-41.
Jones et al., 1986, "Replacing the complementarity-determining regions in a human antibody with those from a mouse," Nature, 321:522-525.
Joseph et al., 2003, "Convenient Synthetic Routes to 5-Substituted 3-(4-Methoxyphenyl)-4(1h)-Quinolones," Synlett, 1542-44.
Jovanovic et al., 2001, "A simple analysis of gene expression and variability in gene arrays based on repeated observations," Am. J. Pharmacogenomics, 1: 145-52.
Jovanovic et al., 2002, "An analysis of gene array data related to cell adhesion and prostate cancer," Cancer Treat. Res. 113:91-111 (Abstract Only).
Kamsteeg et al., 2003, "Phenoxodiol—an isoflavone analog—induces apoptosis in chemoresistant ovarian cancer cells," Oncogene, 22:2611-2620.
Kanth and Brown, 2002, "A new catalytic enantioselective reducing reagent system from (−)-alpha,alpha-diphenylpyrrolidinemethanol and 9-borabicyclo [3.3.1]nonane, especially effective for hindered and substituted aralkylketones," Tetrahedron, 58:1069-74.
Kao et al., 2000, "Use of complementary health practices by prostate carcinoma patients undergoing radiation therapy," Cancer, 88:615-619.
Kasimir-Bauer, 2009,"Circulating tumor cells as markers for cancer risk assessment and treatment monitoring." Mol. Diagn. Ther. 13:209-215.
Kato et al., 2005, "Function of nuclear sex hormone receptors in gene regulation," Cancer Chemother Pharmacol, 56 Suppl 1:4-9.
Kawamura et al., 2002, "Synthesis of Isoflavones from 2'-hydroxylchlacones using poly[4-(diacetoxy)iodo]styrene or related hypervalent iodine reagent," Synthesis, 17:2490-96.
Kimira et al., 1998, "Japanese intake of flavonoids and isoflavonoids from foods," J Epidemiol, 1998, 8:168-175.
Kleiner and Stetler-Stevenson, 1999, "Matrix metalloproteinases and metastasis," Cancer Chemotherap Pharmacol, 43:542-551.
Kohler et al., 1975, "Continuous cultures of fused cells secreting antibody of predefined specificity," Nature 256:495-497.
Kohno et al., 2006, "Targeting the ERK signaling pathway in cancer therapy," Ann Med, 38:200-211.
Kola and Landis, 2004, "Can the pharmaceutical industry reduce attrition rates?" Nat Rev Drug Discov, 3:711-715.
Kostenuik et al., 1997, "Transforming growth factor beta upregulates the integrin-mediated adhesion of human prostatic carcinoma cells to type I collagen," Clin Exp Metastasis, 15:41-52.
Kozbor, 1984, "A human hybrid myeloma for production of human monoclonal antibodies," J Immunol 133:3001.
Kretschmer-Kazemi and Sczakiel, 2003, "The activity of siRNA in mammalian cells is related to structural target accessibility: a comparison with antisense oligonucleotides," Nucleic Acids Res 2003, 31(15):4417-24.
Kyle et al., 1997, "Genistein-induced apoptosis of prostate cancer cells is preceded by a specific decrease in focal adhesion kinase activity," Mol Pharmacol, 51(2): 193-200.
Lakshman et al., 2004, "CD44 negatively regulates apoptosis in murine colonic epithelium via the mitochondrial pathway," Exp. Mol. Pathol. 76:196-204.
Lakshman et al., 2005, "CD44 promotes resistance to apoptosis in murine colonic epithelium," J. Cell Physiol. 203:583-588.
Lakshman et al., 2008, "Dietary genistein inhibits metastasis of human prostate cancer in mice," Cancer Res. 68:2024-2032.
Laux et al., 2000, "GAP43, MARCKS, and CAP-23 modulate PI(4,5) at plasmalemmal rafts, and regulate cell cortex actin dynamics through a common mechanism," J. Cell Biol. 149:1455-72.
Lawson et al., 2007, "Multivitamin use and risk of prostate cancer in the National Institutes of Health-AARP Diet and Health Study," J Natl Cancer Inst, 99:754-764.

(56) References Cited

OTHER PUBLICATIONS

Leav et al., 2001, "Comparative studies of the estrogen beta and alpha and the androgen receptor in normal human prostate glands, dysplasia, and in primary and metastatic carcinoma," Am J Pathol, 159:79-92.
Lebrin et al., 2004, "Endoglin promotes endothelial cell proliferation and TGF-beta/ALK1 signal transduction," EMBO J. 23:4018-4028.
Nielsen et al., 1991, "Sequence-Selective Recognition of DNA by Strand Displacement with a Thymine-Substituted Polyamide," Science 254:1497-1500.
Ota et al., 2002, "Targets of transcriptional regulation by two distinct type I receptors for transforming growth factor-beta in human umbilical vein endothelial cells," J. Cell Physiol. 193:299-318.
Overall et al., 2002, "Strategies for MMP inhibition in cancer: innovations for the post-trial era," Nat Rev Cancer, 2:657-672.
Overhoff et al., 2005, "Local RNA target structure influences siRNA efficacy: a systematic global analysis," J Mol Biol, 348(4):871-81.
Oxmann et al., 2008, "Endoglin expression in metastatic breast cancer cells enhances their invasive phenotype," Oncogene 27:3567-3575.
Pandini et al., 2005 "Androgens up-regulate the insulin-like growth factor-I receptor in prostate cancer cells," Cancer Res, 65:1849-1857.
Perez-Gomez et al., 2007, "A role for endoglin as a suppressor of malignancy during mouse skin carcinogenesis," Cancer Res. 67:10268-10277.
Peterson and Barnes, 1993, "Genistein and biochanin A inhibit the growth of human prostate cancer cell but not epidermal growth factor receptor tyrosine autophosphorylation," Prostate, 22:335-45 (Abstract Only).
Pilat et al., 1993, "Differential induction of pS2 and cathepsin D mRNAs by structurally altered estrogens," Biochemistry, 32:7009-7015.
Platanias, 2003, "Map kinase signaling pathways and hematologic malignancies," Blood, 101:4667-4679.
Pollack et al., 2004, "Ki-67 staining is a strong predictor of distant metastasis and mortality for men with prostate cancer treated with radiotherapy plus androgen deprivation: Radiation Therapy Oncology Group Trial 92-02," J. Clin. Oncol. 22:2133-2140.
Posner, 2005, "High-throughput screening-driven lead discovery: meeting the challenges of finding new therapeutics," Curr Opin Drug Discov Devel, 8:487-494.
Prakash et al., 1990, "1,2-Aryl Shift in the Hypervalent Iodine Oxidation of Flavanones—a New Useful Synthesis of Isoflavones," Synlett, 6:337-38.
Raingeaud et al., 1996, "MKK3- and MKK6-regulated gene expression is mediated by the p38 mitogen-activated protein kinase signal transduction pathway," Mol Cell Biol, 16:1247-1255.
Rajan et al., 2004, "Novel catalytic mechanism of glycoside hydrolysis based on the structure of an NAD+/Mn2-dependent phosphor-alpha-glucosidase from *Bacillus subtilis*," Structure, 12:1619-1629.
Rajan et al., 2004, "YfiT from *Bacillus subtilis* is a probable metal-dependent hydrolase with an unusual four-helix bundle topology," Biochemistry, 43:15472-15479.
Rajan et al., 2006, "Crystal structure of YfiR, an unusual TetR/CamR-type putative transcriptional regulator from *Bacillus subtilis*," Proteins, 65:255-257.
Ralay et al., 2006, "Glia as a therapeutic target: selective suppression of human amyloid-beta-induced upregulation of brain proinflammatory cytokine production attenuates neurodegeneration," J Neurosci, 26:662-670.
Rennebeck et al., 2005, "Anoikis and survival connections in the tumor microenvironment : is there a role in prostate cancer metastasis?" Cancer Res, 2005, 65:11230-11235.
Revill et al., 2006, "AZD-6244" Drugs of the Future, 31:854 (Abstract Only).
Richardson et al., 2000, "Complementary/alternative medicine use in a comprehensive cancer center and the amplifications for oncology," J Clin Oncol, 18:2505-2514.

Riechmann et al., 1988, "Reshaping human antibodies for therapy," Nature, 332:323-327.
Rinehart et al., 2004, "Multicenter phase II study of the oral MEK inhibitor, CI-1040, in patients with advanced non-small-cell lung, breast, colon, and pancreatic cancer," J Clin Oncol, 22:4456-4462.
Rocchi et al., 2004, "Heat shock protein 27 increases after androgen ablation and plays a cytoprotective role in hormone-refractory prostate cancer," Cancer Res, 64:6595-6602.
Rocchi et al., 2005, "Increased Hsp27 after androgen ablation facilitates androgen-independent progression in prostate cancer via signal transducers and activators of transcription 3-mediated suppression of apoptosis," Cancer Res, 65:11083-11093.
Rohlff et al., 1998, "Prostate Cancer Cell Growth Inhibition by Tamoxifen is Associated with Inhibition of Protein Kinase C and Induction of p21waf1/cip1," Prostate 37:51-59.
Rubin et al., 2000, "Rapid ("warm") autopsy study for procurement of metastatic prostate cancer," Clin. Cancer Res. 6:1038-1045.
Ruoslahti et al.,1996, "How cancer spreads," Sci Am, 275:72-77.
Sams-Dodd, 2005, "Target-based drug discovery: is something wrong?" Drug Discov Today, 10:139-147.
Sastre et al., 2008, "Circulating tumor cells in colorectal cancer: correlation with clinical and pathological variables," Ann Oncol. 19:935-938.
Sastry and Burridge, 2000, "Focal adhesions: A nexus for intracellular signaling and cytoskeletal dynamics," Exp Cell Res, 261:25-36.
Schaller et al., 1992, "pp125FAK a structurally distinctive protein-tyrosine kinase associated with focal adhesions," PNAS, 89:5192-5196.
Schubert et al., 2005, "Local RNA target structure influences siRNA efficacy: a systematic analysis of intentionally designed binding regions," J Mol Biol, 348(4):883-93.
Schumacher et al., 2002, "DAPK catalytic activity in the hippocampus increases during the recovery phase in an animal model of brain hypoxic-ischemic injury," Biochim Biophys Acta, 1600:128-137.
Schumacher et al., 2002, "Death-associated protein kinase as a potential therapeutic target," Expert Opin Ther Targets, 6:497-506.
Schumacher et al., 2004, "A calmodulin-regulated protein kinase linked to neuron survival is a substrate for the calmodulin-regulated death-associated protein kinase," Biochemistry, 43:8116-8124.
Schwartz et al., 1998. "Growth inhibition of chronic myelogenous leukemia cells by ODN-1, an aptameric inhibitor of p210bcr-abl tyrosine kinase activity". Antisense Nucleic Acid Drug Dev, 8:329-39.
Severson et al., 1989, "A prospective study of demographics, diet, and prostate cancer among men of Japanese ancestry in Hawaii," Cancer Res. 49:1857-1860.
Shah et al., 2004, "Androgen-independent prostate cancer is a heterogeneous group of diseases: lessons from a rapid autopsy program," Cancer Res, 64:9209-9216.
Shimizu et al., 1991, "Cancers of the prostate and breast among Japanese and white immigrants in Los Angeles County," Br J Cancer, 63(6):963-6.
Sohail et al., 2001, "Antisense oligonucleotides selected by hybridisation to scanning arrays are effective reagents in vivo," Nucleic Acids Res, 29(10): 2041-2045.
Stearns and Stearns, 1996, "Evidence for increased activated metalloproteinase 2 (MMP-2a) expression associated with human prostate cancer progression," Oncol Res, 8:69-75 (Abstract Only).
Stearns and Stearns, 1996, "Immunohistochemical studies of activated matrix metalloproteinase-2 (MMP-2a) expression in human prostate cancer," Oncol Res, 8:63-67(Abstract Only).
Stearns and Wang, 1993, "Type IV collagenase (M(r) 72,000) expression in human prostate: benign and malignant tissue," Cancer Res, 53:878-883.
Stetler-Stevenson et al., 2001, "Proteases in invasion: matrix metalloproteinases," 11:143-152.
Susse et al., 1992, "Synthesis and Behavior of Isoflavones Substituted in 2'-Position," Helv. Chim. Acta, 75:457-70.
Takahashi et al., 2001, "Association of serum endoglin with metastasis in patients with colorectal, breast, and other solid tumors, and suppressive effect of chemotherapy on the serum endoglin," Clin. Cancer Res. 7:524-532.

(56) References Cited

OTHER PUBLICATIONS

Takimoto et al., 2003, "Phase I pharmacokinetic and pharmacodynamic analysis of unconjugated soy isoflavones administered to individuals with cancer," Cancer Epidemio Biomarkers Prevo 12:1213-21.
Taneja et al., 2003, "Structure of the *Bacillus subtilis* YYCN protein: a putative N-acetyltransferase," Proteins, 53:950-952.
Tang and Zhang, 2003, "New chiral phosphorus ligands for enantioselective hydrogenation," Chemical Reviews, 103:3029-70.
Lee et al., 2005, "MAP kinase p38 Inhibitors: Clinical Results and an Intimate Look at Their Interactions with p38 Protein," Current Medicinal Chemistry, 12:2979-2994.
Lettan et al., 2005, "Lewis base-catalyzed additions of alkynes using trialkoxysilyalkynes" Org Lett, 7:3227-3230.
Lettan et al., 2007, "Synthesis of Acylsilanes from Morpholine Amides. Synthesis of 1-(Dimethyl(Phenyl)silylpropan-1-one," Organic Syntheses, vol. 84, p. 22-31.
Li, 2001. "Screening for human ADME/Tox drug properties in drug discovery," Drug Discovery Today, 6:357-366.
Lipinski and Hopkins, 2004, "Navigating chemical space for biology and medicine," 432:855-861.
Lipinski, 2003, "Compound Properties and drug quality" The Practice of Medicinal Chemistry (Abstract Only).
Liu and Bergan, 2001,"Improved intracellular delivery of oligonucleotides by square wave electroporation," Antisense Nucleic Acid Drug Dev, 11:7-14.
Liu et al., 1996, "A human Mad protein acting as a BMP-regulated transcriptional activator [see comments]," Nature, 381:620-623.
Liu et al., 2000, "Focal adhesion kinase (FAK) phosphorylation is not required for genistein-induced FAK-b-1-integrin complex formation," Clin. and Exp. Metastasis, 18:203-212.
Liu et al., 2001, "Prostate cancer chemoprevention agents exhibit selective activity against early stage prostate cancer cells", Prostate Cancer Prostatic Dis. 4: 81-91.
Liu et al., 2002, "Over expression of endoglin in human prostate cancer suppresses cell detachment, migration and invasion," Oncogene 21:8272-8281.
Locklin et al., 2001, "Assessment of gene regulation by bone morphogenetic protein 2 in human marrow stromal cells using gene array technology," J. Bone Miner. Res., 16:2192-2204.
Loganadane et al., 1999, "Transforming growth factor-beta 1 increases the adhesion of MDA-MB-231 mammary adenocarcinoma cells to the microvascular subendothelium," Cell Adhes Commun,7:57-71.
Lorusso et al., 2005, "Phase I and pharmacodynamic study of the oral MEK inhibitor CI-1040 in patients with advanced malignancies," J Clin Oncol, 23:5281-5293.
Losa et al., 2003, "Role of the p38 MAPK pathway in cisplatin-based therapy," Oncogene, 22:3998-4006.
Lukas et al., 1999, "Identification of novel classes of protein kinase inhibitors using combinatorial peptide chemistry based on functional genomics knowledge," J Med Chem, 42:910-919.
Lygo and Andrews, 2004, "Asymmetric phase-transfer catalysis utilizing chiral quaternary ammonium salts: asymmetric alkylation of glycine imines," Acc Chem Res, 37:518-525.
Manas et al., 2004, "Understanding the selectivity of genistein for human estrogen receptor-beta using X-ray crystallography and computational methods," Structure, 2197-2207.
Marhefka et al., 2001, "Homology modeling using multiple molecular dynamics simulations and docking studies of the human androgen receptor ligand binding domain bound to testosterone and nonsteroidal ligands," J Med Chem, 44:1729-1740.
Marks et al., 1991, "By-passing immunization. Human antibodies from V-gene libraries displayed on phage," J Mol Biol 222: 581-597.
Marks et al., 1992, "By-passing immunization: building high affinity human antibodies by chain shuffling,"BioTechnology 10: 779-783 (Abstract Only).
Martin et al., 1995, "A New Access to 2'-O-Alkylated Ribonucleotides and Properties of 2'-O-Alkylated Oligoribonucleotides," Helv Chim Acta 78:486-504.

Massague et al., 1996, "TGFbeta signaling: receptors, transducers, and Mad proteins," Cell, 85:947-950.
Massague, 1998, "TGF-beta signal transduction," Annu Rev Biochem, 67:753-791.
Matsumura et al., 2005, "Comparative study of oestrogenic properties of eight phytoestrogens in MCF7 human breast cells", J Steroid Biochem Mol Biol. 94(5):431-43.
Mattson et al., 2004, "Catalytic additions of acylsilanes to imines: an acyl anion strategy for the direct synthesis of alpha-amino ketones," Org Lett, 6:4363-4366.
Mattson et al., 2004, "The thiazolium-catalyzed Sila-Stetter reaction: conjugate addition of acylsilanes to unsaturated esters and ketones," J Am Chem Soc, 126:2314-2315.
Mattson et al., 2006, "Direct Nucleophilic Acylation of Nitroalkenes Promoted by a Fluoride Anion/Thiourea Combination" J. Am. Chem. Soc., 128, 4932-4933.
McCafferty et al., 1990, "Phage antibodies: filamentous phage displaying antibody variable domains," Nature 348:552-554.
McKillop et al., 1970, "Thallium in Organic Synthesis.21. Direct Conversion of Chalcones into Benzils with Thallium (Iii) Nitrate (Ttn)," Tet. Lett, 5281.
Merzak, et al., 1994, "Control of human glioma cell growth, migration and invasion in vitro by transforming growth factor beta 1," Br J Cancer, 70:199-203.
Messina et al., 1994, "Soy intake and cancer risk: a review of the in vitro and in vivo data," Nutr Cancer, 21:113-31 (Abstract Only).
Messina et al., 2001 "Soy for breast cancer survivors: a critical review of the literature," J Nutr, 131(11 Suppl):3095S-3108S.
Miller et al., 2003, "Crystal complexes of a predicted S-adenosylmethionine-dependent methyltransferase," Protein Sci, 12:1432-1442.
Miller et al., 2007, "Structural and Biochemical Characterization of a novel Mn2+-Dependent Phosphodiesterase Encoded by the yfcE Gene," Protein Science, 16(7):1338-48.
Minasov et al., 2000, "Functional implications from crystal structures of the conserved *Bacillus subtilis* protein Maf with and without dUTP," PNAS, 97:6328-6333.
Mirzoeva et al., 1999, "Screening in a cell-based assay for inhibitors of microglial nitric oxide production reveals calmodulin-regulated protein kinases as potential drug discovery targets," Brain Res, 844:126-134.
Mirzoeva et al., 2002, "Discovery of a 3-amino-6-phenyl-pyridazine derivative as a new synthetic antineuroinflammatory compound," J Med Chem, 45:563-566.
Mol, et al., 1994, "Structure of an immunoglobin Fab fragment specific for poly (dG). poly(dC)," J Biol Chem, 269:3605-3614.
Morino et al., 1997, "Specific expression of HSP27 in human tumor cell lines in vitro," In Vivo, 11:179-184 (Abstract Only).
Morris et al., 2005, "Stereoselective synthesis of tetrahydrophan-4-ones from dioxinones catalyzed by scandium (III) triflate," Org Lett, 7:1113-1116.
Morrison et al., 1984, "Chimeric human antibody molecules: mouse antigen-binding domains with human constant region domains," Proc Nat Acad Sci USA, 81:6851-5.
Myers et al., 2005, "Catalytic conjugate additions of carbonyl anions under neutral aqueous conditions," J Am Chem Soc, 127:14675-14680.
Mysliwiec et al., 2008, "Combined perioperative plasma endoglin and VEGF-A assessment in colorectal cancer patients," Folia Histochem. Cytobiol. 46:487-492.
Nagata et al., 1997, "Decreased serum estradiol concentration associated with high dietary intake of soy products in premenopausal Japanese women," Nutr Cancer, 29:228-233 (Abstract Only).
Nagata et al., 1998, "Decreased serum total cholesterol concentration is associated with high intake of soy products in Japanese men and women," J Nutr, 128:209-213.
Nagata et al., 2000, "Association of diet with the onset of menopause in Japanese women," Am J Epidemiol, 152:863-867.
Nagata et al., 2000, "Inverse associationof soy product intake with serum androgen and estrogen concentrations in Japanese men," Nutr Cancer, 36:14-18.

(56) References Cited

OTHER PUBLICATIONS

Nagata et al., 2000, "Relations of insulin resistance and serum concentrations of estradiol and sex hormone-binding globulin to potential breast cancer risk factors," Jpn J Cancer Res, 91:948-953 (Abstract Only).
Nagle et al., 1994, "Adhesion molecules, extracellular matrix, and proteases in prostate carcinoma," J Cell Biochem Suppl, 19:232-237 (Abstract Only).
Ten Dijke and Hill, 2004, "New insights into TGF-beta-Smad signaling," Trends Biochem Sci, 29:265-273.
Teplova et al., 2000, "The structure of the yrdC gene product from *Escherichia coli* reveal a new fold and suggest a role in RNA building," Protein Sci, 9:2557-2566.
Tereshko et al., 2001, "Crystal structures of the catalytic domain of human protein kinase associated with apoptosis and tumor suppression," Nat Struct Biol, 8:899-907.
Teti et al., 1997, "Transforming growth factor-beta enhances adhesion of melanoma cells to the endothelium in vitro," Int J Cancer, 72:1013-20.
The Alpha-Tocopherol, Beta Carotene Cancer Prevention Study Group, 1994, "The effect of vitamin E and beta carotene on the incidence of lung cancer and others in male smokers," N Engl J Med, 330:1029-1035.
The Leuprolide Study Group, 1984, "Leuprolide versus diethylstilbestrol for metastatic prostate cancer," N Engl J Med, 311:1281-1286 (Abstract Only).
Traxler et al., 1999, "Use of a pharmacophore model for the design of EGFR tyrosine kinase inhibitors: Isoflavones and 3-phenyl-4(1H)-quinolones," J. Med. Chem., 42:1018-26.
Tremblay, et al., 1996, "Focal adhesion kinase (pp125FAK) expression, activation and association with paxillin and p50CSK in human metastatic prostate carcinoma," Int J Cancer, 68:164-171.
Tuerk and Gold, 1990, "Systematic Evolution of Ligands by Exponential Enrichment: RNA Ligands to Bacteriophage T4 DNA Polymerase," Science, 249:505-10.
Tuschl and Borkhardt, 2002, "Small Interfering RNAs: A Revolutionary Tool for the Analysis of Gene Function and Gene Therapy,"Molecular Intervent 2(3):158-67.
Uneda et al., 2009, "Anti-endoglin monoclonal antibodies are effective for suppressing metastasis and the primary tumors by targeting tumor vasculature," Int. J. Cancer 125:1446-1453.
Van Bokhoven et al., 2003, "Molecular Characterization of human prostate carcinoma cell lines," Prostate, 57:205-225.
Van Den Bemd, et al., 2003, "The atypical GATA protein TRPS1 represses androgen-induced prostate-specific antigen expression in LNCaP prostate cancer cells," Biochem Biophys Res Commun, 312:577-584.
Van Der Greef and McBurney, 2005, "Innovation: Rescuing drug discovery: in vivo systems pathology and systems pharmacology," Nat Rev Drug Discov, 4:961-967.
Van Eldik et al., 2002, "Barriers to Alzheimer disease drug discovery and development in academia," Alzheimer Dis Assoc Disord., 16 Suppl 1:S18-28.
Vanloock et al., 2003, "Complexes of RecA with LexA and RecX differentiate between actibe and inactive RecA nucleoprotein filaments," J Mol Biol, 333:345-354.
Varrot et al., 2005, "NAD+ and metal-ion dependent hydrolysis by family glycosidases: structural insight into specificity for phosphor-beta-D-glucosides," J Mol Biol, 346:423-435.
Vasselin et al, 2006, "Structural Studies on Bioactive Compounds. 40.1 Synthesis and Biological Properties of Fluoro-, Methoxyl-, and Amino-Substituted 3-Phenyl-4H-1-benzopyran-4-ones and a Comparison of Their Antitumor Activities with the Activities of Related 2-Phenylbenzothiazoles", J. Med. Chem., 49 (13), pp. 3973-3981.
Velentza et al., 2001, "A protein kinase associated with apoptosis and tumor suppression: structure, activity, and discovery of peptide substrates," J Biol Chem, 276:38956-38965.
Velentza et al., 2002, "Structure, activity, regulation, and inhibitor discovery for a protein kinase associated with apoptosis and neuronal death," Pharmacol Ther., 93:217-224.
Velentza et al., 2003, "An aminopyridazine-based inhibitor of a pro-apoptotic protein kinase attenuates hypoxia-ischemia induced acute brain injury," Bioorg Med Chem Lett, 13:3465-3470.
Veltri et al., 2000, "Quantitative nuclear grade (QNG): a new image-analysis-based biomarker of clinically relevant nuclear structure alterations," J. Cell Biochem. Suppl 151-57.
Verhoeyen et al., 1988, "Reshaping human antibodies: grafting an antilysozyme activity," Science, 239:1534-1536.
Vieth et al., 2004, "Characteristic physical properties and structural fragments of marketed oral drugs," J Med Chem, 47:224-232.
Vo et al., 2010, "Elevated plasma endoglin (CD105) predicts decreased response and survival in a metastatic breast cancer trial of hormone therapy," Breast Cancer Res. Treat., 119: 767-771.
Wahala and Tapio, 1991, "Expedient synthesis of polyhydroxyisoflavones," J Chem Soc—Perkin Trans 1, p. 3005-3008.
Wainwright et al., 2003, "Protein kinase involved in lung injury susceptibility: evidence from enzyme isoform genetic knockout and in vivo inhibitor treatment," PNAS, 100:6233-6238.
Wakai et al., 1999, "Dietary intake and souces of isoflavones among Japanese," Nutr Cancer, 33:139-145.
Walker et al., 1994, "Relationship of transforming growth factor beta-1 to extracellular matrix and stromal infiltrates in invasive breast carcinoma," Br J Cancer, 69:1160-1165.
Ware et al., 1999, "Structure of the fibrinogen gamma-chain integrin recognition segment of the fibrinogen gamma chain obtained by carrier protein-driven crystallization," Protein Sci, 8:2663-2671.
Waterhouse et al., 1993, "Combinatorial infection and in vivo recombination: a strategy for making large phage antibody repertoires," Nuc Acids Res 21:2265-2266.
Watterson et al., 2002, "Discovery of new chemical classes of synthetic ligands that suppress neuroinflammatory responses," J Mol Neurosci, 19:89-93.
Watterson et al., 2003, "Discovery of a new class of synthetic protein kinase inhibitors that suppress selective aspects of glial activation and protect against beta-amyloid induced injury: a foundation for future medicinal chemistry efforts focused on targeting Alzheimer's disease progression," J Mol Neurosci, 20:411-423.
Wells et al., 2002, "Growth factor-induced cell motility in tumor invasion," Acta Oncol, 41:124-130.
Wermuth et al., 2004, "Selective optimization of side activities: another way for drug discovery," J Med Chem, 47:1303-1314.
White, 2002, "PC-SPES—a lesson for future dietary supplement research," J Natl Cancer Inst, 94:1261-1263.
Wiederkehr et al., 1997,"The motility-associated proteins GAP-43, MARCKS, and CAP-23 share unique targeting and surface activity-inducing properties," Exp. Cell Res. 236:103-16.
Wing et al., 2006, "De novo and molecular targetindependent discovery of orally bioavailable lead compounds for neurological disorders," Curr Alzheimer Res, 3(3):205-14.
Witkowski et al., 1993, "Characterization of integrin subunits, cellular adhesion and tumorgenicity of four human prostate cell lines," J Cancer Res Clin Oncol, 119:637-644 (Abstract Only).
Wong et al., 2008, "Identification of an invasion and tumor-suppressing gene, Endoglin (ENG), silenced by both epigenetic inactivation and allelic loss in esophageal squamous cell carcinoma," Int J Cancer, 123:2816-2823.
Wood et al., 1997, "In situ hybridization studies of metalloproteinases 2 and 9 and TIMP-1 and TIMP-2 expression in human prostate cancer," Clin Exp. Metastasis, 15:246-258.
Woodhouse et al., 1997, "General Mechanisms of metastasis," Cancer, 80 (8 Suppl):1529-1537.
Wyckoff et al., 2000, "A critical step in metastasis: in vivo analysis of intravasation at the primary tumor," Cancer Res. 60:2504-2511.
Xu et al., 2006, "MAPKAPK2 and HSP27 are downstream effectors of p38 MAP kinase-mediated matrix metalloproteinase type 2 activation and cell invasion in human prostate cancer," Oncogene, 25:2987-2998.
Xu et al., 2006. "Genistein Inhibits Matrix Metalloproteinase Type 2 Activation and Prostate Cancer Cell Invasion by Blocking the Transforming Growth Factor beta-Mediated Activation of Mitogen-Activated Protein Kinase-Activated Protein Kinase 2-27-kDa Heat Shock Protein Pathway," Mol Pharmacol, 70:869-77.

(56) References Cited

OTHER PUBLICATIONS

Xu et al., 2008, "Multiple effects of acetaminophen and p38 inhibitors: towards pathway toxicology," FEBS Lett, 8:1276-82.
Xu et al., 2009, "MEK4 function, genistein treatment, and invasion of human prostate cancer cells," J Natl. Cancer Inst. 101:1141-1155.
Xue et al., 2006, "Epidermal growth factor receptor overexpression results in increased tumor cell motility in vivo coordinately with enhanced intravasation and metastasis." Cancer Res. 66:192-197.
Yamada, 1997, "Integrin signaling," Matrix Biol, 16:137-141.
Yamamoto et al., 2001, "Validity and reproducibility of a self administered food-frequency questionnaire to assess isoflavone intake in a Japanese population in comparison with dietary records and blood and urine isoflavones," J Nutr, 131:2741-2747.
Young et al., 1997, "Pyridinyl imidazole inhibitors of p38 mitogen-activated protein kinase bind in the ATP site," J. Biol. Chem 272:12116-21.
Zeisel et al., 1999, "Regulation of "nutraceuticals"," Science, 285:1853-1855.
[No Author Listed], 1996, "Clinical Development Plan: Genistein", J Cell Biochem Suppl, 26:114-126.
Adlercreutz et al., 1990, "Western diet and Western diseases: some hormonal and biochemical mechanisms and associations", Scand. J. Clin. Lab. Invest. Suppl 201: 3-23 (Abstract Only).
Adlercreutz et al., 1991, "Urinary excretion of lignans and isoflavonoid phytoestrogens in Japanes men and women and consuming a traditional Japanese diet," Am J Clin Nutr, 54:1093-1100.
Adlercreutz et al., 1993, "Plasma concentrations of phyto-oestrogens in Japanese men," Lancet, 342:1209-10.
Akiyama et al., 1987, "Genistein, a specific inhibitor of tyrosine-specific protein kinases," J Biol Chem, 262:5592-5595.
Albo et al., 1997, "Thrombospondin-1 and transforming growth factor beta I promote breast tumor cell invasion through up-regulation of the plasminogen/plasmin system," Surgery, 122:493-499; discussion 499-500.
Al-Maharik and Botting, 2003, "Synthesis of lupiwighteone via a para-Claisen-Cope rearrangement," Tetrahedron, 59:4177-4181.
Anderson et al., 1981, "Structure of the cro repressor from bacteriophage lambda and its interaction with DNA," Nature, 290:754-758.
Anderson et al., 1982, "Proposed alpha-helical super-secondary structure associated with protein-dna recognition," J Mol Biol, 159:745-751.
Antus et al., 1981, "Unusual Regioselectivity in the Reduction of Alpha, Beta-Unsaturated Carbonyl-Compounds with Diisobutylaluminum Hydride (Dibah)—Direct Conversion of Isoflavones to Isoflavon-4-ones," Synthesis—Stuttgart, 7:574-576.
Arai et al., 2000, "Comparison of isoflavones among dietary intake, plasma concentration and urinary excretion for accurate estimation of phytoestrogen intake," J Epidemiol, 10:127-135.
Arai et al., 2000, "Dietary intakes of flavonols, flavones, and isoflavones by Japanese women and the inverse correlation between quercetin intake and plasma LDL cholesterol concentration," J Nutr, 130:2243-2250.
Bacon and Anderson, 1986, "Multiple sequence alignment," J Mol Biol, 191:153-161.
Baker et al., 1928, "Synthetical Experiments in the isoFlavone Group. Part III. A Synthesis of Genistein," Journal of the Chemical Society, 3115-3118.
Balasubramanian et al., 2000, "An efficient "one pot" synthesis of Isoflavones," Synthetic Communications, 30:469-484.
Ballweg et al., 2005, "Stereoselective synthesis of alpha-silylamines by the direct addition of silyl anions to activated imines," Org Lett, 7:1403-1406.
Bao et al., 2006, "p38 MAP kinase inhibitors: metabolically stabilized piperidine-substituted quinolinones and naphthyridinones," Bioorg. Medicinal Chem Lett. 16:64-8.
Barbara et al., 1999, "Endoglin is an accessory protein that interacts with the signaling receptor complex of multiple members of the transforming growth factor-beta superfamily," J. Biol. Chem, 274:584-594.
Bardin et al., 2004, "Involvement of estrogen receptor beta in ovarian carcinogenesis," Cancer Res, 64:5861-5869.
Bartels et al., 1998, "Nuclear chromatin texture in prostatic lesions I. PIN and adenocarcinoma," Anal. Quant. Cytol. Histol. 20:389-96 (Abstract Only).
Bartels et al., 1998, "Nuclear chromatin texture in prostatic lesions. II. PIN and malignancy associated changes," Anal Quant Cytol Histol, 20:397-406 (Abstract Only).
Bartels et al., 2001, "Karyometry of secretory cell nuclei in high-grade PIN lesions," Prostate, 48:144-55.
Bergan et al., 1993, "Electroporation enhances c-myc antisense oligodeoxynucleotide efficacy," Nucleic Acids Res, 21:3567-3573.
Bergan et al., 1994, "Aptameric inhibition of p210bcr-abl tyrosine kinase autophosphorylation by oligodeoxynucleotides of defined sequence and backbone structure," Nucleic Acids Res. 22:2150-54.
Bergan et al., 1995, "Inhibition of protein-tyrosine kinase in intact cells by the aptameric action of oligodeoxynucleotides," Antisense Res. Dev. 5:33-8.
Bergan et al., 1996, "Electroporation of synthetic oligodeoxynucleotides: a novel technique for ex vivo bone marrow purging," Blood, 88:731-741.
Bergan et al., 1996, "Genistein-stimulated adherence of prostate cancer cells is associated with the binding of focal adhesion kinase to beta-1-integrin," Clin Exp Metastasis, 389-398 (Abstract Only).
Bergan et al., 1999, "A Phase II Study of High Dose Tamoxifen in Patients with Hormone Refractory Prostate Cancer," Clinical Cancer Research, 5:2366-2373.
Bergan et al., 2001, "Tyrosine Kinase Inhibitors and Signal Transduction Modulators: Rationale and Current Status as Chemopreventive Agents for Prostate Cancer," Urology, 57(4 Suppl 1): 77-80.
Bertolino et al., 2005, "Transforming growth factor-beta signal transduction in angiogenesis and vascular disorders," Chest 128(6 Suppl) 585S-590S.
Bharadwaj et al., 2004, "Catalytic multicomponent synthesis of highly substituted pyrroles utilizing a one-plot sila-Stetter/Paal-Knorr strategy," Org Lett, 6:2465-2468.
Biddle et al., 2007. "Catalytic enantioselective synthesis of flavanones and chromanones," Journal of the American Chemical Society, 129:3830-3801.
Blanco et al., 2005, "Interaction and functional interplay between endoglin and ALK-1, two components of the endothelial transforming growth factor-beta receptor complex," J. Cell Physiol. 204:574-587.
Bleicher et al., 2003, "Hit and Lead Generation: beyond high-throughput screening," Nat Rev Drug Discov, 2:369-378.
Bloedon et al., 2002, "Safety and pharmacokinetics of purified soy isoflavones: a single-dose administration to postmenopausal women," Am J Clin Nutr, 76:1126-1137.
Bogenrieder et al., 2003, "Axis of evil: molecular mechanisms of cancer metastasis," Oncogene, 22:6524-6536.
Bohl et al., 2004, "A ligand-based approach to identify quantitative structure activity relationships for the androgen receptor," J Med Chem, 47:3765-3776.
Bohl et al., 2007, "Crystal structure of the T877A human androgen receptor ligand-binding domain complexed to cyproterone acetate provides insight for ligand-induced conformational changes and structure-based drug design," J Biol Chem, 282:13648-13655.
Bohula et al., 2003, "The efficacy of small interfering RNAs targeted to the type 1 insulin-like growth factor receptor (IGF1R) is influenced by secondary structure in the IGF1R transcript," J Biol Chem 278:15991-15997.
Boone et al., 2001, "Computer-Assisted image analysis-derived intermediate endpoints," Urology, 57:129-31.
Brody and Gold, 2000, "Aptamers as therapeutic and diagnostic agents," J. Biotechnol., 74: 5-13.
Brody et al., 1999, "The use of aptamers in large arrays for molecular diagnostics," Mol. Diagn. 4:381-88 (Abstract Only).
Brummelkamp et al., 2002, "A system for stable expression of short interfering RNAs in mammalian cells," Science 296:550-3.
Brunzelle et al., 2003, "Automated crystallographic system for high-throughput protein structure determination," Acta Crystallogr D Biol Crystallogr, 59:1138-1144.

(56) References Cited

OTHER PUBLICATIONS

Brunzelle et al., 2004, "Crystal structure of *Bacillus subtilis* YdaF protein: a putative ribosomal N-acetyltransferase," Proteins, 57:850-853.
Bubendorf et al., 1996, "Ki67 labelling index: an independent predictor of progression in prostate cancer treated by radical prostatectomy," J. Pathol. 178:437-441.
Burke and Gold, 1997, "RNA aptamers to the adenosine moiety of S-adenosyl methionine: structural inferences from variations on a theme and the reproducibility of SELEX," Nucleic Acids Res, 25:2020-4.
Busby et al., 2002, "Clinical characteristics and pharmacokinetics of purified soy isoflavones: a single-dose administration to healthy men," Am J Clin Nutr, 75:126-136.
Butcher, 2005, "Can cell systems biology rescue drug discovery?" Nat Reve Drug Discov, 4:461-467.
Cai et al., 2000, "TGF-beta 1 modulated the expression of alpha 5 beta 1 integrin and integrin-mediated signaling in human hepatocarcinoma cells," Biochem Biophys Res Commun, 274:519-525.

FIGURE 2
FIG. 2A
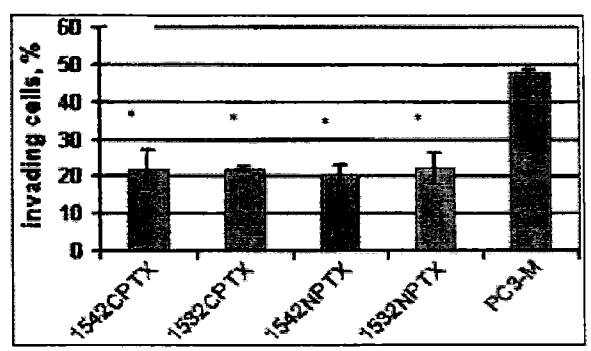
FIG. 2B
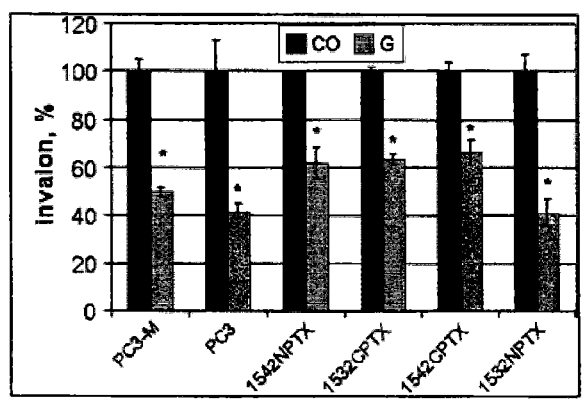

FIGURE 4
FIG. 4A
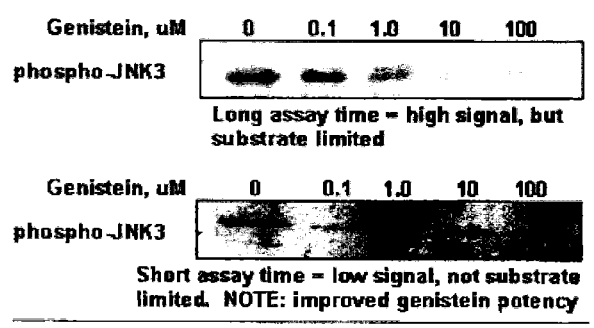
FIG. 4B
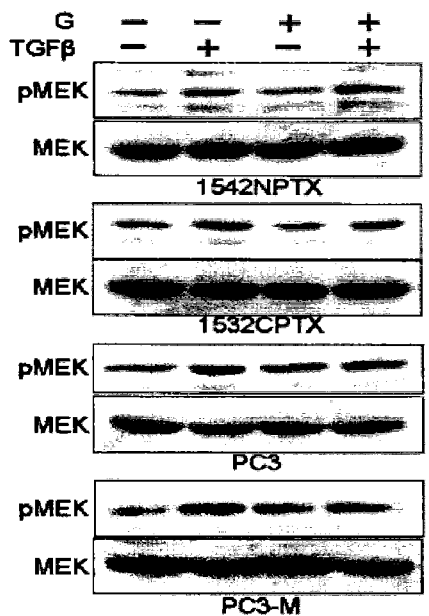

FIGURE 5
FIG. 5A
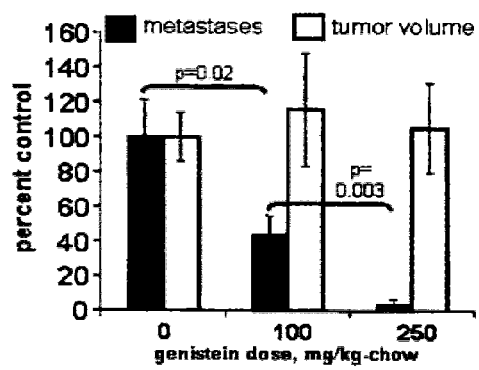
FIG. 5B (upper panel) & 5C (lower panel)
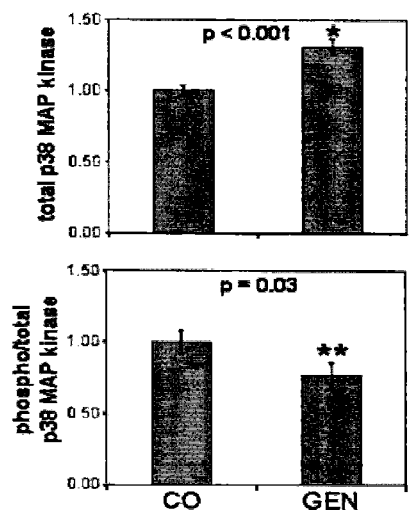

compound 23 compound 24 compound 25 compound 26 compound 33 compound 34 compound 35 compound 36 compound 37 compound 38 compound 41 compound 42 compound 47 compound 48

INHIBITION AND TREATMENT OF PROSTATE CANCER METASTASIS

CROSS-REFERENCE TO RELATED APPLICATION

This application is a continuation of U.S. patent application Ser. No. 12/578,137, filed Oct. 13, 2009, which will issue on Jul. 9, 2013 as U.S. Pat. No. 8,481,760, which claims priority to expired U.S. Provisional Patent Application No. 61/104,564, filed Oct. 10, 2008, the contents of which are incorporated by reference in their entireties.

STATEMENT REGARDING FEDERALLY SPONSORED RESEARCH OR DEVELOPMENT

This invention was made with government support under grant number R21 CA099263 awarded by the National Institutes of Health. The government has certain rights in the invention.

FIELD OF INVENTION

The present invention relates generally to the treatment of prostate cancer and in particular to the inhibition of prostate cancer metastasis. Thus, there are provided compounds and methods for treating prostate cancer metastasis by inhibition of MEK4 kinase.

BACKGROUND

Prostate cancer is the most common noncutaneous cancer in males and the second most common cause of cancer-related death in men in the United States (Jemal et al. (2008) CA Cancer J. Clin. 58:71-96; herein incorporated by reference in its entirety). The American Cancer Society estimates that in 2009, 92, 280 new cases of prostate cancer will be diagnosed and 27,360 men will die of prostate cancer. The incidence of prostate cancer diagnosis in men exceeds 1 in 6, and the death rate due to prostate cancer is approximately 1 in 35. Standard treatment of advanced and/or metastatic prostate cancer includes androgen suppression, cytotoxic chemotherapy, and radiation. These treatment modalities carry significant side effects, and treatment regimes (and consequently likelihood of success) are far more limited for hormone-refractory prostate tumors than hormone-responsive tumors. For metastatic prostate cancer, no form of therapy is curative, and thus this represents a terminal diagnosis. Surgical approaches and radiation, typically in combination with hormone therapy, may be used for intermediate-stage tumors; however, again, these modalities carry significant risk of undesirable side effects such as incontinence and/or impotence. For early-stage tumors, standard approaches consist of surgery, radiation (which may be combined with hormone therapy) or watchful waiting. With watchful waiting, consensus guidelines related to its implementation are lacking, changes in clinical parameters with time lead to frequent repetitive biopsies, and with the knowledge that they have confirmed prostate cancer patients experience high levels of anxiety. All of these factors contribute to a channeling of patients into eventual treatment with surgery or radiation. Prostate cancer can be prevented by finasteride. Finasteride blocks 5-alpha reductase and inhibits the synthesis of dihydrotestosterone. Treatment with finasteride daily for five years reduces prostate cancer incidence by 25%. However, impotence is a major side effect, is not acceptable to most people, and thus finasteride use is limited.

Better treatment of prostate cancer is needed. In particular, agents that prevent prostate cancer metastasis are needed.

SUMMARY OF THE INVENTION

It has been discovered that the kinase MEK4 regulates prostate cancer cell invasion, a key step in the metastasis of prostate cancer. Inhibition of MEK4 blocks downstream activation of MMP-2 and cell invasion and increases cell adhesion (Xu et al. (2009) J. Natl. Cancer Inst. 101:1141-1155; herein incorporated by reference in its entirety). Accordingly, there are provided herein methods of inhibiting and treating prostate cancer metastasis with inhibitors of MEK4 activity. Furthermore, there are provided methods of screening for inhibitors of metastatic prostate cancer by testing compounds for inhibition of MEK4 activity. Also, compounds for use in methods described herein are disclosed, including anti-MEK4 antibodies, siRNA, genistein, and genistein analogs, e.g., isoflavones, isoflavanols, and isoflavanes.

In certain embodiments, the present invention provides a method for inhibiting prostate cancer metastasis, comprising: administering a compound having formula:

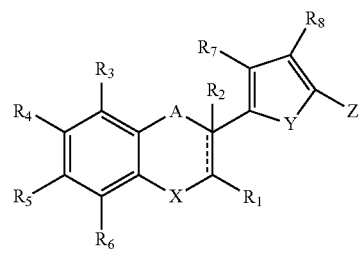

to a subject having prostate cancer; wherein A is O, C=O, CHOH, C=NR, or $CH_2$; X is C=O, O or NH; Y is O, NH, $CR_9$=$CR_{10}$, or CH=N; Z is OH, $OCH_3$, halogen, H provided that one of $R_7$ or $R_8$ is OH or $OCH_3$, or OCO wherein Z forms a heterocyclic group with the carbon at position $R_{10}$; the dashed line represents an optional double bond; R is H or a substituted or unsubstituted alkyl group; $R_1$ is selected from the group consisting of H and substituted or unsubstituted alkyl groups; $R_2$ is selected from the group consisting of H, OH, F and Cl; or is absent when the optional double bond is present; $R_3$, $R_4$, $R_5$, $R_6$, $R_7$, $R_8$, $R_9$ and $R_{10}$ are each independently selected from the group consisting of OH, F, Cl, Br, I, CN, $NO_2$, COOR, $CONH_2$, and substituted and unsubstituted alkyl and alkoxy groups; wherein said compound is not genistein. In some embodiments, if Z is H, one of $R_7$ or $R_8$ is OH or $OCH_3$. In some embodiments, $R_3$, $R_4$, $R_5$, and $R_6$ are each H. In some embodiments, Z is $OCH_3$, halogen, or H. In some embodiments, Z is halogen. In some embodiments, the compound is:

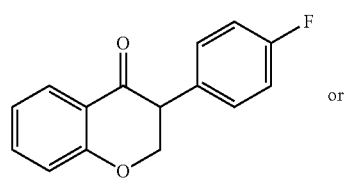

or

-continued

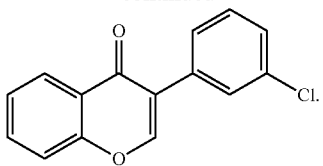

In some embodiments, the subject is a human. In some embodiments, the compound is administered prior to surgical removal of a tumor. In some embodiments, the compound is administered after surgical removal of a tumor. In some embodiments, the compound is co-administered with a different prostate cancer therapeutic agent.

In certain embodiments, the present invention provides a pharmaceutical preparation comprising a compound having formula:

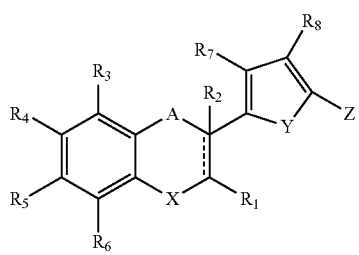

wherein A is O, C=O, CHOH, C=NR, or $CH_2$; X is C=O, O or NH; Y is O, NH, $CR_9$=$CR_{10}$, or CH=N; Z is OH, $OCH_3$, halogen, H provided that one of $R_7$ or $R_8$ is OH or $OCH_3$, or OCO wherein Z forms a heterocyclic group with the carbon at position $R_{10}$; the dashed line represents an optional double bond; R is H or a substituted or unsubstituted alkyl group; $R_1$ is selected from the group consisting of H and substituted or unsubstituted alkyl groups; $R_2$ is selected from the group consisting of H, OH, F and Cl; or is absent when the optional double bond is present; $R_3$, $R_4$, $R_5$, $R_6$, $R_7$, $R_8$, $R_9$ and $R_{10}$ are each independently selected from the group consisting of OH, F, Cl, Br, I, CN, $NO_2$, COOR, $CONH_2$, and substituted and unsubstituted alkyl and alkoxy groups; wherein said compound is not genistein. In some embodiments, if Z is H, one of $R_7$ or $R_8$ is OH or $OCH_3$. In some embodiments, $R_3$, $R_4$, $R_5$, and $R_6$ are each H. In some embodiments, Z is $OCH_3$, halogen, or H. In some embodiments, Z is halogen. In some embodiments, the compound is:

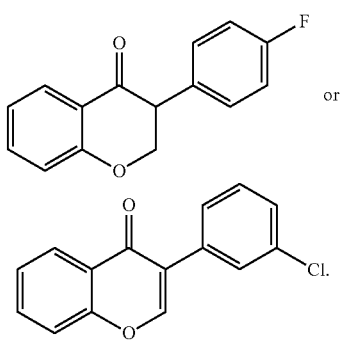

In certain embodiments, the present invention provides a compound having the formula:

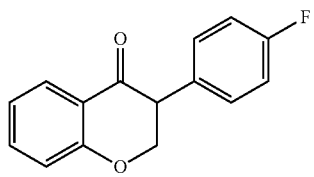 [SMILES: O=C1c2ccccc2OCC1c1ccc(F)cc1]

In some embodiments, this compound is provided as a pharmaceutical composition.

In certain embodiments, the present invention provides a method for treating a subject comprising: administering the compound having the formula

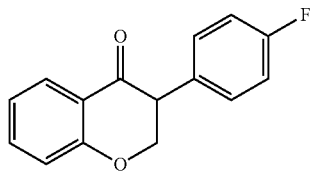 [SMILES: O=C1c2ccccc2OCC1c1ccc(F)cc1]

to a subject.

In certain embodiments, the present invention provides use of a compound having the formula

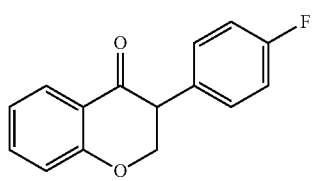 [SMILES: O=C1c2ccccc2OCC1c1ccc(F)cc1]

for the treatment of prostate cancer or for the manufacture of a medicament for use in the treatment or prevention of prostate cancer.

In certain embodiments, the present invention provides a compound having the formula:

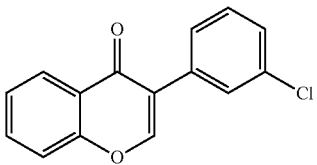 [SMILES: O=c1c(-c2cccc(Cl)c2)coc2ccccc12]

In some embodiments, this compound is provided as a pharmaceutical composition.

In certain embodiments, the present invention provides a method for treating a subject comprising: administering a compound having the formula

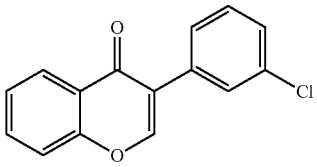 [SMILES: O=c1c(-c2cccc(Cl)c2)coc2ccccc12]

to a subject.

In certain embodiments, the present invention provides the use of a compound having the formula

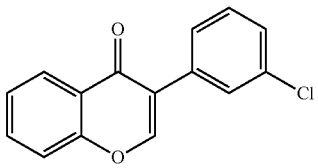 [SMILES: O=c1c(-c2cccc(Cl)c2)coc2ccccc12]

for the treatment of prostate cancer or for the manufacture of a medicament for use in the treatment of prostate cancer.

In certain embodiments, the present invention provides a method for inhibiting prostate cancer metastasis in a subject, comprising activating the endoglin pathway in the subject. In some embodiments, the activation results in increased expression of a gene such as a gene encoding endoglin, a gene encoding ALK2, a gene encoding Smad1, and genes activated by Smad1. In some embodiments, the activation results in increased activity of a protein such as endoglin, ALK2, and Smad1. In some embodiments, the activation is achieved through gene therapy. In some embodiments, the activation is achieved by administration of a small molecule. In some embodiments, the activation is achieved by administration of a compound having formula:

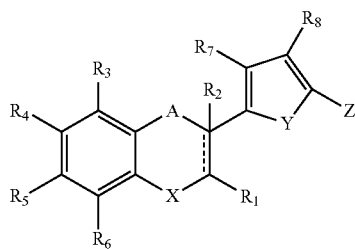

to the subject; wherein A is O, C═O, CHOH, C═NR, or $CH_2$; X is C═O, O or NH; Y is O, NH, $CR_9$═$CR_{10}$, or CH═N; Z is OH, $OCH_3$, halogen, H provided that one of $R_7$ or $R_8$ is OH or $OCH_3$, or OCO wherein Z forms a heterocyclic group with the carbon at position $R_{10}$; the dashed line represents an optional double bond; R is H or a substituted or unsubstituted alkyl group; $R_1$ is selected from the group consisting of H and substituted or unsubstituted alkyl groups; $R_2$ is selected from the group consisting of H, OH, F and Cl; or is absent when the optional double bond is present; $R_3$, $R_4$, $R_5$, $R_6$, $R_7$, $R_8$, $R_9$ and $R_{10}$ are each independently selected from the group consisting of OH, F, Cl, Br, I, CN, $NO_2$, COOR, $CONH_2$, and substituted and unsubstituted alkyl and alkoxy groups; wherein said compound is not genistein. In some embodiments, the activation is achieved by administration of a compound such as

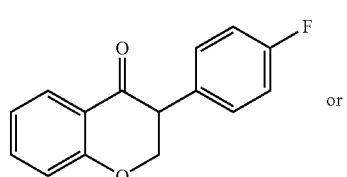

or

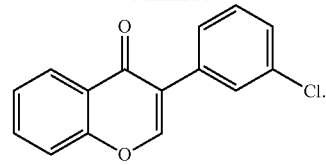

In certain embodiments, the present invention provides a method for preventing prostate cancer cell invasion in a subject, comprising administering a compound having formula:

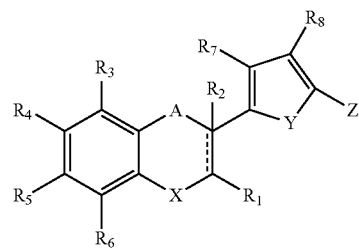

to the subject, wherein A is O, C═O, CHOH, C═NR, or $CH_2$; X is C═O, O or NH; Y is O, NH, $CR_9$═$CR_{10}$, or CH═N; Z is OH, $OCH_3$, halogen, H provided that one of $R_7$ or $R_8$ is OH or $OCH_3$, or OCO wherein Z forms a heterocyclic group with the carbon at position $R_{10}$; the dashed line represents an optional double bond; R is H or a substituted or unsubstituted alkyl group; $R_1$ is selected from the group consisting of H and substituted or unsubstituted alkyl groups; $R_2$ is selected from the group consisting of H, OH, F and Cl; or is absent when the optional double bond is present; $R_3$, $R_4$, $R_5$, $R_6$, $R_7$, $R_8$, $R_9$ and $R_{10}$ are each independently selected from the group consisting of OH, F, Cl, Br, I, CN, $NO_2$, COOR, $CONH_2$, and substituted and unsubstituted alkyl and alkoxy groups; wherein said compound is not genistein. In some embodiments, the subject has been diagnosed with prostatic intraepithelial neoplasmia. In some embodiments, the subject has not been diagnosed with prostatic intraepithelial neoplasmia. In some embodiments, the subject is at risk of developing prostatic intraepithelial neoplasmia.

In certain embodiments, the present invention provides a method for preventing prostate cancer cell invasion in a subject, comprising:

administering a compound selected from the group consisting of

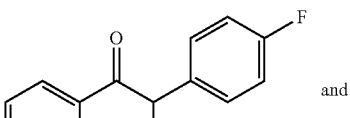

and

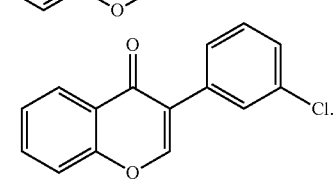

In some embodiments, the subject has been diagnosed with prostatic intraepithelial neoplasmia. In some embodiments, the subject has not been diagnosed with prostatic intraepithelial neoplasmia. In some embodiments, the subject is at risk of developing prostatic intraepithelial neoplasmia.

In certain embodiments, the present invention provides a method of preventing invasion of a prostate cell through the basement membrane into the prostate gland in a subject, comprising:
administering a compound having formula:

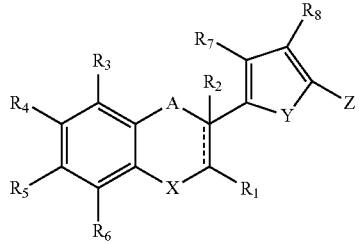

to the subject; wherein A is O, C=O, CHOH, C=NR, or CH$_2$; X is C=O, O or NH; Y is O, NH, CR$_9$=CR$_{10}$, or CH=N; Z is OH, OCH$_3$, halogen, H provided that one of R$_7$ or R$_8$ is OH or OCH$_3$, or OCO wherein Z forms a heterocyclic group with the carbon at position R$_{10}$; the dashed line represents an optional double bond; R is H or a substituted or unsubstituted alkyl group; R$_1$ is selected from the group consisting of H and substituted or unsubstituted alkyl groups; R$_2$ is selected from the group consisting of H, OH, F and Cl; or is absent when the optional double bond is present; R$_3$, R$_4$, R$_5$, R$_6$, R$_7$, R$_8$, R$_9$ and R$_{10}$ are each independently selected from the group consisting of OH, F, Cl, Br, I, CN, NO$_2$, COOR, CONH$_2$, and substituted and unsubstituted alkyl and alkoxy groups; wherein said compound is not genistein. In some embodiments, the subject has been diagnosed with prostatic intraepithelial neoplasmia. In some embodiments, the subject has not been diagnosed with prostatic intraepithelial neoplasmia. In some embodiments, the subject is at risk of developing prostatic intraepithelial neoplasmia.

In certain embodiments, the present invention provides a method of preventing invasion of a prostate cell through the basement membrane into the prostate gland in a subject, comprising:
administering a compound selected from the group consisting of

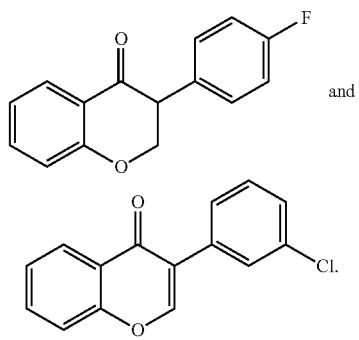

In some embodiments, the subject has been diagnosed with prostatic intraepithelial neoplasmia. In some embodiments, the subject has not been diagnosed with prostatic intraepithelial neoplasmia. In some embodiments, the subject is at risk of developing prostatic intraepithelial neoplasmia.

In certain embodiments, the present invention provides a method for preventing prostate cancer in a subject, comprising:
administering a compound having formula:

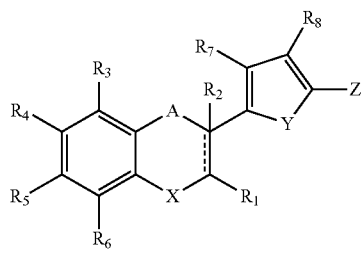

to the subject; wherein A is O, C=O, CHOH, C=NR, or CH$_2$; X is C=O, O or NH; Y is O, NH, CR$_9$=CR$_{10}$, or CH=N; Z is OH, OCH$_3$, halogen, H provided that one of R$_7$ or R$_8$ is OH or OCH$_3$, or OCO wherein Z forms a heterocyclic group with the carbon at position R$_{10}$; the dashed line represents an optional double bond; R is H or a substituted or unsubstituted alkyl group; R$_1$ is selected from the group consisting of H and substituted or unsubstituted alkyl groups; R$_2$ is selected from the group consisting of H, OH, F and Cl; or is absent when the optional double bond is present; R$_3$, R$_4$, R$_5$, R$_6$, R$_7$, R$_8$, R$_9$ and R$_{10}$ are each independently selected from the group consisting of OH, F, Cl, Br, I, CN, NO$_2$, COOR, CONH$_2$, and substituted and unsubstituted alkyl and alkoxy groups; wherein said compound is not genistein.

In certain embodiments, the present invention provides a method of preventing prostate cancer in a subject, comprising:
administering a compound selected from the group consisting of

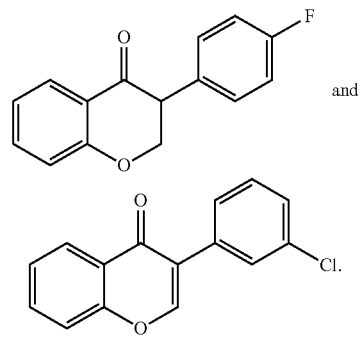

Additional embodiments will be apparent to persons skilled in the relevant art based on the teachings contained herein.

BRIEF DESCRIPTION OF THE DRAWINGS

FIGS. 2A and 2B show prostate cancer cell invasiveness in the absence (2A) and presence (2B) of genistein.

FIG. 3A shows gels showing the expression of MEK4 in various prostate cancer cell lines in the presence and absence of siRNA specific for MEK4. FIGS. 3B and 3C are bar graphs that show the results of RT-PCR experiments detecting the level of transcript for MEK3 (3B) and MEK4 (3C) in various prostate cancer cell lines in the absence and presence of siRNA. FIG. 3D is a bar graph showing that knockdown of MEK4 with siRNA specific for MEK4 suppresses prostate cancer cell invasion and abrogates the effect of genistein.

FIGS. 4A and 4B show the effects of genistein on phosphorylation by or of MEK4. FIG. 4A is a gel showing that genistein inhibits phosphorylation of JNK3 by MEK4. FIG. 4B shows that in vivo, genistein does not block TGF-β stimulated phosphorylation of MEK4 itself.

FIG. 5A is a graph showing that genistein decreased metastasis but not tumor volume in a dose dependent fashion. FIG. 5B are graphs showing that genistein blocks activation of p38 MAP kinase in vivo by decreasing phosphorylation of p38 MAP kinase even while the total amount of p38 MAP kinase increased.

DEFINITIONS

Figure 1:
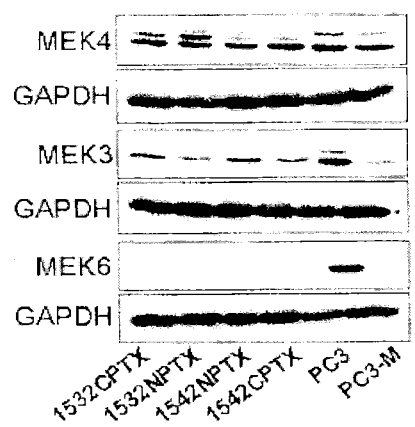
FIG. 1 shows SDS-PAGE gels resulting from a Western blot analysis of MEK3, MEK4, and MEK 6 expression in six prostate cancer cell lines.

As used herein, the term "MEK4 pathway protein" refers to proteins both upstream and downstream of MEK4, as well as MEK4 itself, that are related to cancer cell metastasis (e.g., in prostate cancer) and include, but is not limited to, the following proteins: MEK4 (MAP2K4; MKK4), p38 MAPK (MAPK14), MAPKAPK2 (MK2), HSP27 (HSB1), and MMP-2 (Matrix metallopeptidase 2).

As used herein, the term "MEK4 pathway nucleic acid" refers to nucleic acids that encode the MEK4 pathway proteins.

As used herein, the term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. In certain embodiments, the antibodies of the present invention are directed toward a MEK4 pathway protein (e.g., anti-MEK4, anti-p38 MAPK, anti-MEK4 pathway, anti-MAPKAPK2, anti-HSP27, and anti-MMP-2).

As used herein, the term "antibody fragments" refers to a portion of an intact antibody. Examples of antibody fragments include, but are not limited to, linear antibodies; single-chain antibody molecules; Fc or Fc' peptides, Fab and Fab' fragments, and multispecific antibodies formed from antibody fragments. The antibody fragments preferably retain at least part of the hinge and optionally the CH1 region of an IgG heavy chain. In other preferred embodiments, the antibody fragments comprise at least a portion of the CH2 region or the entire CH2 region. In certain embodiments, the antibody fragments of the present invention are directed toward a MEK4 pathway protein.

As used herein, the term "functional fragment", when used in reference to a monoclonal antibody, is intended to refer to a portion of the monoclonal antibody which still retains a functional activity. A functional activity can be, for example, antigen binding activity or specificity. Monoclonal antibody functional fragments include, for example, individual heavy or light or light chains and fragments thereof, such as VL, VH and Fd; monovalent fragments, such as Fv, Fab, and Fab'; bivalent fragments such as F(ab')$_2$; single chain Fv (scFv); and Fc fragments. Such terms are described in, for example, Harlowe and Lane, Antibodies: A Laboratory Manual, Cold Spring Harbor Laboratory, New York (1989); Molec. Biology and Biotechnology: A Comprehensive Desk Reference (Myers, R. A. (ed.), New York: VCH Publisher, Inc.); Huston et al., Cell Biophysics, 22:189-224 (1993); Pluckthun and Skerra, Meth. Enzymol., 178:497-515 (1989) and in Day, E. D., Advanced Immunochemistry, Second Ed., Wiley-Liss, Inc., New York, N.Y. (1990), all of which are herein incorporated by reference. The term functional fragment is intended to include, for example, fragments produced by protease digestion or reduction of a monoclonal antibody and by recombinant DNA methods known to those skilled in the art.

As used herein, "humanized" forms of non-human (e.g., murine) antibodies are chimeric antibodies that contain minimal sequence, or no sequence, derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are generally made to further refine antibody performance. In general, the humanized antibody will comprise substantially all of at least one, and typically two, variable domains, in which all or substantially all of the hypervariable loops correspond to those of a nonhuman immunoglobulin and all or substantially all of the FR residues are those of a human immunoglobulin sequence. The humanized antibody may also comprise at least a portion of an immunoglobulin constant region (Fc), typically that of a human immunoglobulin. Examples of methods used to generate humanized antibodies are described in U.S. Pat. No. 5,225,539 to Winter et al. (herein incorporated by reference). In certain embodiments, the present invention employs humanized anti-MEK4 pathway protein antibodies.

As used herein, the term "hypervariable region" refers to the amino acid residues of an antibody which are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196: 901-917 (1987), hereby incorporated by reference in its entirety). "Framework" or "FR" residues are those variable domain residues other than the hypervariable region residues as defined herein.

As used herein, the term "siRNAs" refers to small interfering RNAs. In some embodiments, siRNAs comprise a duplex, or double-stranded region, which can be in the form of a hairpin of about 18-25 nucleotides long; often siRNAs contain from about two to four unpaired nucleotides at the 3' end of each strand. At least one strand of the duplex or double-stranded region of a siRNA is substantially homologous to, or substantially complementary to, a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants. In certain embodiments, the siRNAs target MEK4 pathway nucleic acid, such as the mRNA that encodes one of the MEK4 pathway proteins.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and/or molecular screening tests.

As used herein, the term "initial diagnosis" refers to a test result of initial cancer diagnosis that reveals the presence or absence of cancerous cells (e.g., using a biopsy and histology).

As used herein, the term "prostate tumor tissue" refers to cancerous tissue of the prostate. In some embodiments, the prostate tumor tissue is "post surgical prostate tumor tissue."

As used herein, the term "post surgical tumor tissue" refers to cancerous tissue that has been removed from a subject (e.g., during surgery).

As used herein, the term "identifying the risk of said tumor metastasizing" refers to the relative risk (e.g., the percent chance or a relative score) of a tumor metastasizing.

As used herein, the term "identifying the risk of said tumor recurring" refers to the relative risk (e.g., the percent chance or a relative score) of a tumor recurring in the same organ as the original tumor.

As used herein, the term "subject at risk for cancer" refers to a subject with one or more risk factors for developing a specific cancer. Risk factors include, but are not limited to, gender, age, genetic predisposition, environmental exposure, and previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue and the stage of the cancer.

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

Several staging methods are commonly used for cancer (e.g, prostate cancer). Using prostate cancer as one non-limiting example, a common classification of the spread of prostate cancer uses the Whitmore-Jewett staging system. This system divides prostate tumors into four stages, A to D. Stage A, microscopic cancer within prostate, is further subdivided into stages A1 and A2. Sub-stage A1 is when only a small amount of cancer is present in the tissue. Treatment is generally observation, radical prostatectomy, or radiation with or without hormone therapy. Sub-stage A2 is when the percentage of cancer occupying the tissue is more extensive. Treatment is radical prostatectomy or radiation with or without hormone therapy. Stage B, palpable lump within the prostate, is also further subdivided into sub-stages B1 and B2. In sub-stage B1, the cancer forms a small nodule in one lobe of the prostate. In sub-stage B2, the cancer forms large or multiple nodules, or occurs in both lobes of the prostate. Treatment for sub-stages B1 and B2 is either radical prostatectomy or radiation with or without hormone therapy. With stage C, the cancer mass has extended beyond the prostate gland, typically involves a large cancer mass involving most or all of the prostate, and is also further subdivided into two sub-stages. In sub-stage C1, the cancer forms a continuous mass that extends beyond the prostate. In sub-stage C2, the cancer forms a continuous mass that extends beyond the prostate and invades the seminal vesicles. Treatment for both these sub-stages is radiation with or without hormone therapy and with or without chemotherapy to address the cancer. The fourth stage, Stage D is metastatic cancer and is also subdivided into two sub-stages. In sub-stage D1, the cancer appears in the lymph nodes of the pelvis. In sub-stage D2, the cancer involves tissues beyond lymph nodes. Treatment for both of these sub-stages is systemic drugs involving hormone therapy with or without chemotherapy to address the cancer as well as pain.

As a further example of cancer staging, using prostate cancer as a non-limiting example, a "GLEASON score" refers to a histologic grade that refers to the microscopic characteristics of malignant prostatic tumor. Individual areas receive a grade from 1 to 5. Cells that are well differentiated are given a low grade; poorly differentiated cells are given a high grade. A primary grade is assigned to the pattern occupying the greatest area of the specimen and a secondary grade is assigned to the second-largest affected area. These two grades are then added together for an overall Gleason score (or sum). The most well-differentiated cancer would receive a Gleason score of 2 (1+1), while the most poorly differentiated cancer would receive a Gleason score of 10 (5+5).

Staging of prostate cancer can also be based on the revised criteria of TNM staging by the American Joint Committee for Cancer (AJCC) published in 1988. Staging is the process of describing the extent to which cancer has spread from the site of its origin. It is used to assess a patient's prognosis and to determine the choice of therapy. The stage of a cancer is determined by the size and location in the body of the primary tumor, and whether it has spread to other areas of the body. Staging involves using the letters T, N and M to assess tumors by the size of the primary tumor (T); the degree to which regional lymph nodes (N) are involved; and the absence or presence of distant metastases (M)—cancer that has spread from the original (primary) tumor to distant organs or distant lymph nodes. Each of these categories is further classified with a number 1 through 4 to give the total stage. Once the T, N and M are determined, a "stage" of I, II, III or IV is assigned. Stage I cancers are small, localized, usually curable, and correspond to stage A of the Whitmore-Jewett staging system. Stage II cancers similarly correspond to stage B cancer in the Whitmore-Jewett staging system, and stage III cancers correspond to stage C cancers in the Whitmore-Jewett staging system. Stage IV cancers are metastatic (have spread to distant parts of the body), correspond to stage D in the Whitmore-Jewett staging system, and are considered inoperable.

As used herein, the term "characterizing tissue in a subject" refers to the identification of one or more properties of a tissue sample (e.g., including but not limited to, the presence of cancerous tissue, the presence of pre-cancerous tissue that is likely to become cancerous (such as prostatic intraepithelial neoplasia, or PIN), and the presence of cancerous tissue that is likely to metastasize).

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "non-human animals" refers to all non-human animals including, but not limited to, vertebrates such as rodents, non-human primates, ovines, bovines, ruminants, lagomorphs, porcines, caprines, equines, canines, felines, ayes, etc.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. Such examples are not however to be construed as limiting the sample types applicable to the present invention.

DETAILED DESCRIPTION

Figure 27:
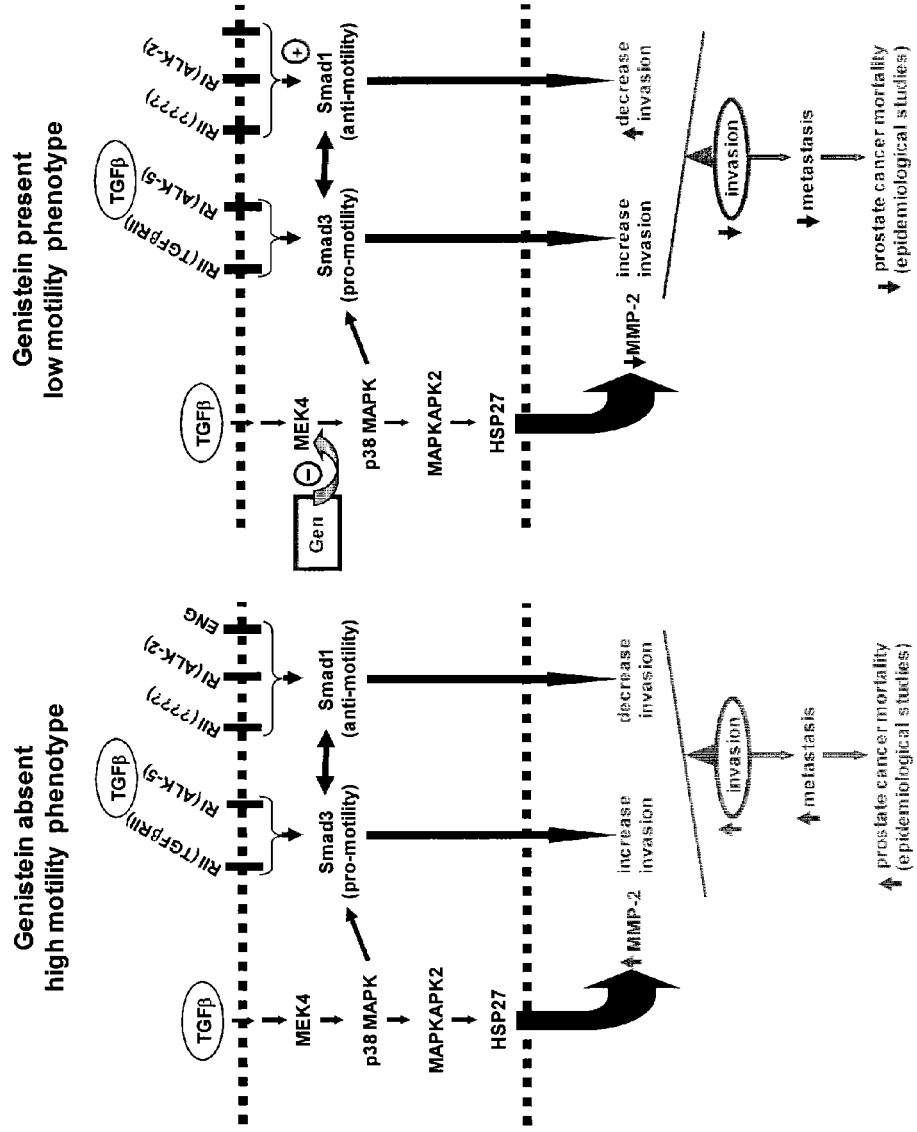
FIG. 27 shows a model for the MEK4 regulation of human prostate cell motility and for its inhibition by genistein. Left) High motility phenotype. Transforming growth factor 0 (TGFβ) activates MEK4. Activated MEK4 in turn activates downstream effector proteins, including p38 mitogen-activated protein kinase (MAPK) (Huang et al. (2005) Cancer Res. 65:3470-3478; herein incorporated by reference in its entirety), mitogen-activated protein kinase-activated protein kinase 2 (MAPKAPK2) (Xu et al. (2006) Oncogene 25:2987-2998; herein incorporated by reference in its entirety), and heat shock protein 27 (HSP27) (Xu et al. (2006) Oncogene 25:2987-2998; herein incorporated by reference in its entirety), all of which act to increase expression of matrix metalloproteinase type-2 (MMP-2) and cell invasion. Smad3 can be activated by p38 MAPK (Hayes et al. (2003) Oncogene 22:4841-4850; herein incorporated by reference in its entirety) or by the TGFβ superfamily receptors, ALK-5 and TGFβRII (Craft et al. (2007) Oncogene 26:7240-7250; herein incorporated by reference in its entirety). The pro-invasive action of Smad3 is mitigated by the anti-invasion action of Smad1 (Craft et al. (2007) Oncogene 26:7240-7250; herein incorporated by reference in its entirety). Smad1 is constitutively activated by endoglin in an ALK-2 dependent fashion (Craft et al. (2007) Oncogene 26:7240-7250; herein incorporated by reference in its entirety). Under the combined influence of pro-invasion MEK4 and Smad3 signaling, and of anti-invasion Smad1 signaling, cells have a high motility phenotype characterized by high invasion and metastatic potential (Lakshman et al. (2008) Cancer Res. 68:2024-2032; herein incorporated by reference in its entirety), which in turn causes mortality from prostate cancer. Right) Genistein treatment and low motility phenotype. When genistein is present, it binds to and inhibits MEK4 kinase activity. Genistein-mediated decreases in MEK4 kinase activity in turn blocks activation of p38 MAPK (Huang et al. (2005) Cancer Res. 65:3470-3478; herein incorporated by reference in its entirety), MAPKAPK2 (Xu et al. (2006) Oncogene 25:2987-2998; herein incorporated by reference in its entirety), and HSP27 (Xu et al. (2006) Oncogene 25:2987-2998; herein incorporated by reference in its entirety), all of which block TGFβ-mediated increases in MMP-2 and cell invasion. In addition, genistein activates the antimotility action of Smad1, in a manner that is dependent on ALK-2 kinase activity (Craft et al. (2008) Mol. Pharmacol. 73:235-242; herein incorporated by reference in its entirety). Genistein's action serves to inhibit pro-invasion MEK4 and Smad3 signaling, and to enhance anti-invasion Smad1 signaling, resulting in cells with a low motility phenotype characterized by low invasion and metastatic potential (Lakshman et al. (2008) Cancer Res. 68:2024-2032; herein incorporated by reference in its entirety), which in decreases mortality from prostate cancer (Severson et al. (1989) Cancer Res. 49:1857-1860; Adlercreutz (1990) Scand. J. Clin. Lab. Invest. 50 (suppl 201):3-203; each herein incorporated by reference in its entirety). −=inhibitory activity of genistein on a molecular pathway; +=stimulatory activity of genistein on a molecular pathway; ↓=inhibition of individual cellular and systemic processes by genistein; ↑=stimulation of individual cellular and systemic processes by genistein; TGFβ=transforming growth factor β; MEK4=mitogen-activated protein kinase kinase 4; p38 MAPK=p38 mitogen-activated protein kinase; MAPKAPK2=mitogen-activated protein kinase-activated protein kinase 2; HSP27=heat shock protein 27; MMP-2=matrix metalloproteinase type 2; TGFβRI and TGFβRII=type I and II TGFβ receptor; ALK=activin-like kinase receptor; ENG=endoglin.

In one aspect, the present invention provides methods for inhibiting and/or treating prostate cancer. In experiments described herein, MEK4 is shown to be a proinvasion protein in human prostate cancer, and inhibition of MEK4 is shown to inhibit expression of proinvasion genes (e.g., matrix metalloprotease 2 (MMP-2)) and cell invasion (FIG. 27) (Xu et al. (2009) J. Natl. Cancer Inst. 101:1141-1155; herein incorporated by reference in its entirety). Further, in experiments described herein, endoglin and members of the endoglin/ALK-2/Smad1 pathway were found to suppress human prostate cancer metastasis (e.g., Example 14) such that increased activation of this pathway is correlated with anti-invasive effects.

Methods of MEK4 inhibition include administering a therapeutically effective amount of an isolated MEK4 inhibitor to a subject suffering from metastatic prostate cancer or at risk for metastatic prostate cancer. Isolated MEK4 inhibitors are MEK4 inhibitors that have either been purified in some way from a natural source or have been produced synthetically. MEK4 inhibitors suitable for use in the present methods include compounds which bind directly to MEK4 and, e.g., interfere with or inhibit MEK4 activity such as the phosphorylation of p38 MAP kinase. Other MEK4 inhibitors suitable for use in the present methods include compounds that reduce expression of MEK4. For example, MEK4 inhibitors that may be employed in the present methods include antibodies, isoflavones such as genistein, isoflavanols, isoflavanes, and molecules that interfere with MEK4 expression, such as siRNA and antisense oligonucleotides. In some embodiments the MEK4 inhibitor is not genistein.

The present invention provides therapeutic agents for treating prostate cancer. In particular embodiments, the therapeutic agents are small molecules, antibodies, or nucleic acid molecules (e.g., anti-sense or siRNA molecules) that inhibit a MEK4 pathway protein or MEK4 pathway nucleic acid. In particular embodiments, the MEK4 pathway protein or nucleic acid is MEK4. In other embodiments, the MEK4 protein is selected from the group consisting of: MEK4 (MAP2K4; MKK4), p38 MAPK (MAPK14), MAPKAPK2 (MK2), HSP27 (HSB1), and MMP-2 (Matrix metallopeptidase 2).

1. Small Molecules MEK4 Pathway Inhibitors

There are provided herein compounds for use in methods of treating or inhibiting metastasis of prostate cancer including compounds of Formula I. Formula I is

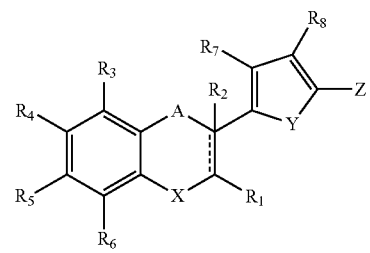

and stereoisomers, or pharmaceutically acceptable salts thereof, wherein,
A is C=O, CHOH, C=NR, or $CH_2$;
X is O or NH;
Y is O, NH, $CR_9$=$CR_{10}$, or CH=N;
Z is OH, $OCH_3$, halogen (F, Cl, Br, I), or may be H provided that one of $R_7$ or $R_8$ is OH or $OCH_3$; or may form a heterocyclic ring with the carbon associated with $R_{10}$, for example where $Z/R_{10}$ is OCO;
the dashed line represents an optional double bond;
R is H or a substituted or unsubstituted alkyl group;
$R_1$ is selected from the group consisting of H and substituted or unsubstituted alkyl groups;
$R_2$ is selected from the group consisting of H, OH, F and Cl; or is absent when the optional double bond is present;
$R_3$, $R_4$, $R_5$, $R_6$, $R_7$, $R_8$, $R_9$ and $R_{10}$ are each independently selected from the group consisting of OH, F, Cl, Br, I, CN, $NO_2$, COOR, $CONH_2$, and substituted and unsubstituted alkyl and alkoxy groups; and
R is, at each occurrence, independently a substituted or unsubstituted alkyl or alkoxy group.

In some embodiments, the compound of Formula I is not genistein (i.e., $R_3$ is not —OH, or $R_4$ is not —H, or $R_5$ is not —OH, or $R_6$ is not —H, or A is not C=O, or X is not O, or $R_1$ is not —H, or $R_2$ is not —H, or Y is not $CR_9$=$CR_{10}$ where $R_9$ and $R_{10}$ are —H, or Z is not —OH, or $R_7$ is not H, or $R_8$ is not H). For example, in some embodiments, the compound of Formula I lacks an —OH group at one or more of position $R_3$, $R_5$ or Z. For example, in some embodiments, $R_3$ and $R_5$ each independently are H, halogen, $NO_2$, COOR, $CONH_2$, or substituted and unsubstituted alkyl and alkoxy groups (e.g., $R_3$ and $R_5$ are each H; e.g., $R_3$, $R_4$, $R_5$, and $R_6$ are each H). Likewise, in some embodiments, Z is $OCH_3$, halogen, or H. In some embodiments, $R_9$ or $R_{10}$ is halogen.

In some embodiments of compounds of Formula I, the double bond represented by the dashed line is present. Alternatively, in certain compounds of Formula I, the double bond represented by the dashed line is absent.

In compounds of Formula I, A can be C=O or CHOH. A may also be CH$_2$. In other embodiments, Y can be CR$_9$=CR$_{10}$. For example, Y can be CH=CH. In still other embodiments, Z can be OH. Compounds of Formula I also include compounds wherein A is C=O, the double bond represented by the dashed line is absent, and Y is CR$_9$=CR$_{10}$.

There are further provided herein compounds for use in methods of treating or inhibiting metastasis of prostate cancer include compounds of Formula II. Formula II is:

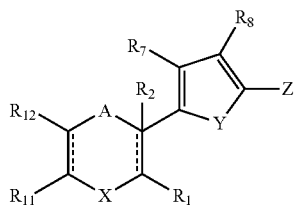

and stereoisomers, or pharmaceutically acceptable salts thereof, wherein,

A is O, C=O, CHOH, C=NR, or CH$_2$;

X is C=O, O or NH;

Y is O, NH, CR$_9$=CR$_{10}$, or CH=N;

Z is OH, OCH$_3$, halogen (F, Cl, Br, I), or may be H provided that one of R$_7$ or R$_8$ is OH or OCH$_3$; or may form a heterocyclic ring with the carbon associated with R$_{10}$, for example where Z/R$_{10}$ is OCO;

the dashed lines represent optional double bonds;

R is H or a substituted or unsubstituted alkyl group;

R$_1$ is selected from the group consisting of H and substituted or unsubstituted alkyl groups;

R$_6$, R$_7$, R$_8$, R$_9$, R$_{10}$, R$_{11}$, and R$_{12}$ are each independently selected from the group consisting of OH, F, Cl, Br, I, CN, NO$_2$, COOR, CONH$_2$, and substituted and unsubstituted alkyl and alkoxy groups; and R is, at each occurrence, independently a substituted or unsubstituted alkyl or alkoxy group.

In some embodiments, the heterocyclic ring attached at the 2-position of the naphthalene scaffold (i.e., the ring attached at the carbon attached to the R$_2$ group in Formula II, above) is instead provided at the 3 position (i.e., the carbon attached to the R$_1$ group in Formula I, above). In some such embodiments, A is C=O and X is O.

In some embodiments, R$_{11}$ and R$_{12}$ are present in a heterocyclic ring, which includes, but is not limited to, structures shown in Formula I. The heterocyclic ring containing R$_{11}$, and R$_{12}$ may comprise a 5, 6, or greater atom ring and, in some embodiments, may comprise C, N, O, or S in the ring. Thus, in some embodiments, a heterocyclic ring containing R$_{11}$, and R$_{12}$ is a pyridine, pryimidine, pyrane, thiine, diazine, thiazine, or dioxine ring.

In some embodiments of compounds of Formula II, one or both of the double bonds represented by the dashed lines are present. Alternatively, in certain compounds of Formula II, one or both of the double bonds represented by the dashed line are absent.

In compounds of Formula II, A can be C=O or CHOH. A may also be CH$_2$. In other embodiments, Y can be CR$_9$=CR$_{10}$. For example, Y can be CH=CH. In still other embodiments, Z can be OH. Compounds of Formula II also include compounds wherein A is C=O, the double bond represented by the dashed line is absent, and Y is CR$_9$=CR$_{10}$.

In some embodiments, the compound of Formula II is not genistein (e.g., R$_{11}$, and R$_{12}$ are not contained in a heterocyclic ring).

Existing therapies for the treatment of prostate cancer may be used in combination with the present methods. Thus methods of treating or inhibiting metastatic prostate cancer may further include administering the MEK4 inhibitor in conjunction with a second therapy for the treatment of prostate cancer. The second therapy may be another MEK4 inhibitor but typically is a different therapy. Suitable different therapies include one or more therapies selected from the group consisting of radiation treatment and prostatectomy. Another second therapy that may be used is anti-androgen therapy. The anti-androgen therapy may include administering to the subject one or more agents selected from the group consisting of leuprolide and goserelin. Another second therapy that may be employed is chemotherapy such as administering one or more hormonal or chemotherapeutic agents that include but are not limited to ketoconazole, bicalutamide (Casodex), mitoxantrone (Novantrone), estramustine phosphate (Emcyt), etoposide (Vepsid), paclitaxel (Taxol), docetaxel (Taxotere), doxorubicin (Adriamycin), or vinblastine (Velban).

In another aspect, the invention provides methods of screening for compounds that inhibit prostate cancer metastasis comprising contacting MEK4 with one or more compounds in vitro and determining whether the compound inhibits MEK4. In some embodiments, MEK4 is in a cell, e.g., in a cell culture system. In other embodiments, MEK4 is an isolated enzyme. In some embodiments, the compounds are selected from the group consisting of isoflavones, isoflavanols, and isoflavanes.

The following abbreviations and terms are used throughout as defined below.

MEK4 is a kinase that phosphorylates p38 MAP kinase among other substrates and regulates prostate cancer cell motility and invasion.

PCa stands for prostate cancer.

SDS-PAGE stands for sodium dodecyl-sulfate polyacrylamide gel electrophoresis.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sufides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitriles (i.e. CN); and the like.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched alkyl groups having from 1 to about 20 carbon atoms, and typically from 1 to 12 carbons or, in some embodiments, from 1 to 8, 1 to 6, or 1 to 4 carbon atoms. Alkyl groups further include cycloalkyl groups as defined below. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, tert-butyl, neopentyl, isopentyl, and 2,2-dimethylpropyl groups. Representative substituted alkyl groups may be substituted one or more times with substituents such as those listed above.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 10 or 3 to 8 ring members, whereas in other embodiments the number of ring carbon atoms range from 3 to 5, 3 to 6, or 3 to 7. Cycloalkyl groups further include mono-, bicyclic and polycyclic ring systems, such as, for example bridged cycloalkyl groups as described below, and fused rings, such as, but not limited to, decalinyl, and the like. In some embodiments, polycyclic cycloalkyl groups have three rings. Substituted cycloalkyl groups may be substituted one or more times with non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-, 2,5- or 2,6-disubstituted cyclohexyl groups, which may be substituted with substituents such as those listed above.

Bridged cycloalkyl groups are cycloalkyl groups in which two or more hydrogen atoms are replaced by an alkylene bridge, wherein the bridge can contain 2 to 6 carbon atoms if two hydrogen atoms are located on the same carbon atom, or 1 to 5 carbon atoms if the two hydrogen atoms are located on adjacent carbon atoms, or 2 to 4 carbon atoms if the two hydrogen atoms are located on carbon atoms separated by 1 or 2 carbon atoms. Bridged cycloalkyl groups can be bicyclic, such as, for example bicyclo[2.1.1]hexane, or tricyclic, such as, for example, adamantyl. Representative bridged cycloalkyl groups include bicyclo[2.1.1]hexyl, bicyclo[2.2.1]heptyl, bicyclo[3.2.1]octyl, bicyclo[2.2.2]octyl, bicyclo[3.2.2]nonyl, bicyclo[3.3.1]nonyl, bicyclo[3.3.2]decanyl, adamantyl, noradamantyl, bornyl, or norbornyl groups. Substituted bridged cycloalkyl groups may be substituted one or more times with non-hydrogen and non-carbon groups as defined above. Representative substituted bridged cycloalkyl groups may be mono-substituted or substituted more than once, such as, but not limited to, mono-, di- or tri-substituted adamantyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 20 carbon atoms, 4 to 16 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain and cycloalkyl groups as defined above, except that at least one double bond exists between two carbon atoms. Thus, alkenyl groups have from 2 to about 20 carbon atoms, and typically from 2 to 12 carbons or, in some embodiments, from 2 to 8, 2 to 6, or 2 to 4 carbon atoms. In some embodiments, alkenyl groups include cycloalkenyl groups having from 4 to 20 carbon atoms, 5 to 20 carbon atoms, 5 to 10 carbon atoms, or even 5, 6, 7 or 8 carbon atoms. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl, among others. Representative substituted alkenyl groups may be mono-substituted or substituted more than once, such as, but not limited to, mono-, di- or tri-substituted with substituents such as those listed above.

Cycloalkenylalkyl groups are alkyl groups as defined above in which a hydrogen or carbon bond of the alkyl group is replaced with a bond to a cycloalkenyl group as defined above. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8, 2 to 6, or 2 to 4 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$), among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6 to 10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 20 carbon atoms, 7 to 14 carbon atoms or 7 to 10 carbon atoms. Substituted aralkyl groups may be substituted at the alkyl, the aryl, or both the alkyl and the aryl portions of the group. Representative aralkyl groups include but are not limited to benzyl and phenethyl groups and fused (cycloalkylaryl)alkyl groups such as 4-ethylindanyl. Representative substituted aralkyl groups may be substituted one or more times with substituents such as those listed above.

Heterocyclyl groups are non-aromatic rings containing 3 or more ring members, of which one or more is a heteroatom such as, but not limited to, N, O, and S. In some embodiments, heterocyclyl groups include 3 to 20 ring members, whereas other such groups have 3 to 6, 3 to 10, 3 to 12, or 3 to 15 ring members. Heterocyclyl groups encompass partially unsaturated and saturated ring systems, such as, for example, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups." Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, pyrrolinyl, imidazolinyl, pyrazolinyl, thiazolinyl, piperidyl, piperazinyl, morpholinyl, thiomorpholinyl, tetrahydropyranyl, tetrahydrothiopyranyl, dihydropyridyl, dihydrodithiinyl, dihydrodithionyl, homopiperazinyl, quinuclidyl, indolinyl, indolizinyl. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups include at least one aromatic ring containing 5 or more ring members, of which one or more is a heteroatom such as N, O, and S. Heteroaryl groups include fused ring systems in which one or more rings are aryl or heterocyclyl such as indolyl, benzimidazolyl, and 5,6,7,8-tetrahydroquinolinyl. In some embodiments the heteroaryl group is a 5- or 6-member ring, a fused bicyclic ring having from 8-10 members, or a fused tricyclic ring having from 11 to 14 members. In other embodiments the heteroaryl group has 1, 2, 3, or 4 heteroatoms as ring members. Heteroaryl groups thus include, but are not limited to, groups such as pyrrolyl, pyrazolyl, imidazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups may be substituted at the alkyl, the heterocyclyl or both the alkyl and heterocyclyl portions of the group. Representative heterocyclyl alkyl groups include, but are not limited to, 4-ethyl-morpholinyl, 4-propylmorpholinyl, furan-2-yl methyl, furan-3-yl methyl, pyridine-3-yl methyl, tetrahydrofuran-2-yl ethyl, and indol-2-yl propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Substituted heteroaralkyl groups may be substituted at the alkyl, the heteroaryl, or both the alkyl and heteroaryl portions of the group. Representative substituted heteroaralkyl groups may be substituted one or more times with substituents such as those listed above.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

Alkyl, alkenyl, and alkynyl groups maybe divalent as well as monovalent. The valency of an alkyl, alkenyl, or alkynyl group will be readily apparent from the context to those of skill in the art. For example, the alkyl group in an aralkyl group is divalent. In some embodiments, divalency is expressly indicated by appending the suffix "ene" or "ylene" to terms defined herein. Thus, for example, "alkylene" refers to divalent alkyl groups and alkenylene refers to divalent alkene groups.

The term "carboxylate" as used herein refers to a —COOH group.

The term "carboxylic ester" as used herein refers to —COOR$^{30}$ groups. R$^{30}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., —C(O)NR$^{31}$R$^{32}$, and —NR$^{31}$C(O)R$^{32}$ groups, respectively. R$^{31}$ and R$^{32}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H).

Urethane groups include N- and O-urethane groups, i.e., —NR$^{33}$C(O)OR$^{34}$ and —OC(O)NR$^{33}$R$^{34}$ groups, respectively. R$^{33}$ and R$^{34}$ are independently hydrogen, or a substituted or unsubstituted alkyl, alkenyl, alkynyl, cycloalkyl, aryl, aralkyl, heterocyclylalkyl, or heterocyclyl group as defined herein.

The term "amine" (or "amino") as used herein refers to —NHR$^{35}$ and —NR$^{36}$R$^{37}$ groups, wherein R$^{35}$, R$^{36}$ and R$^{37}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is $NH_2$, methylamino, dimethylamino, ethylamino, diethylamino, propylamino, isopropylamino, phenylamino, or benzylamino.

The term "sulfonamido" includes S- and N-sulfonamide groups, i.e., $—SO_2NR^{38}R^{39}$ and $—NR^{38}SO_2R^{39}$ groups, respectively. $R^{38}$ and $R^{39}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include, but are not limited to, sulfamoyl groups ($—SO_2NH_2$).

The term "thiol" refers to —SH groups, while sulfides include —$SR^{40}$ groups, sulfoxides include —$S(O)R^{41}$ groups, sulfones include —$SO_2R^{42}$ groups, and sulfonyls include $SO_2OR^{43}$. $R^{40}$, $R^{41}$, $R^{42}$, and $R^{43}$ are each independently a substituted or unsubstituted alkyl, cycloalkyl, alkenyl, alkynyl, aryl aralkyl, heterocyclyl or heterocyclylalkyl group as defined herein.

The term "urea" refers to $—NR^{44}—C(O)—NR^{45}R^{46}$ groups. $R^{44}$, $R^{45}$, and $R^{46}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to $—C(NR^{47})NR^{48}R^{49}$, and $—NR^{47}C(NR^{48})R^{49}$, wherein $R^{47}$, $R^{48}$, and $R^{49}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to $—NR^{50}C(NR^{51})NR^{52}R^{53}$, wherein $R^{50}$, $R^{51}$, $R^{52}$ and $R^{53}$ are each independently hydrogen, or a substituted or unsubstituted alkyl, cycloalkyl, alkenyl, alkynyl, aryl aralkyl, heterocyclyl or heterocyclylalkyl group as defined herein.)

The term "enamine" refers to $—C(R^{54})=C(R^{55})NR^{56}R^{57}$ and $—NR^{54}C(R^{55})=C(R^{56})R^{57}$, wherein $R^{54}$, $R^{55}$, $R^{56}$ and $R^{57}$ are each independently hydrogen, a substituted or unsubstituted alkyl, cycloalkyl, alkenyl, alkynyl, aryl aralkyl, heterocyclyl or heterocyclylalkyl group as defined herein.

The term "imide" refers to $—C(O)NR^{58}C(O)R^{59}$, wherein $R^{58}$ and $R^{59}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to $—CR^{60}(NR^{61})$ and $—N(CR^{60}R^{61})$ groups, wherein $R^{60}$ and $R^{61}$ are each independently hydrogen or a substituted or unsubstituted alkyl, cycloalkyl, alkenyl, alkynyl, aryl aralkyl, heterocyclyl or heterocyclylalkyl group as defined herein, with the proviso that $R^{60}$ and $R^{61}$ are not both simultaneously hydrogen.

Those of skill in the art will appreciate that compounds of the invention may exhibit the phenomena of tautomerism, conformational isomerism, geometric isomerism and/or optical isomerism. As the formula drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the compounds having one or more of the utilities described herein, as well as mixtures of these various different forms.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, triazoles may exhibit the following isomeric forms, which are referred to as tautomers of each other:

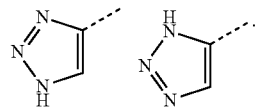

As readily understood by one skilled in the art, a wide variety of functional groups and other structures may exhibit tautomerism, and all tautomers of compounds as described herein are within the scope of the present invention.

Stereoisomers of compounds (also known as optical isomers) include all chiral, diastereomeric, and racemic forms of a structure, unless the specific stereochemistry is expressly indicated. Thus, compounds used in the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these are all within the scope of the invention.

As used herein, a solvate is an aggregation of a molecule and one or more molecules of solvent. Some compounds have a tendency to associate with a fixed molar ratio of solvent molecules in the solid state. The solvent molecules may interact with the non-solvent molecule by dipole-dipole interactions, ion-dipole interactions, coordinate bonds, and the like. When the solvent is water, the solvate is referred to as a hydrate. Many organic solvents can also form solvates, including, e.g., ethers such as diethyl ether and tetrahydrofuran, alcohols such as methanol and ethanol, ketones such as acetone, DMF, DMSO and others. Solvates may be identified by various methods known in the art. For example, solvates in which the solvent molecules contain hydrogen may be observable by $^1$H NMR. Additional methods useful in identifying solvates include thermogravimetric analysis, differential scanning calorimetry, X-ray analysis and elemental analysis. Solvates are readily formed simply by dissolving a compound in a solvent and removing the unassociated solvent by suitable techniques, e.g., evaporation, freeze drying or crystallization techniques. It is therefore well within the skill in the art to produce such solvates. Indeed, it is often the case that careful drying of a compound is necessary to remove the residual solvent that is part of a solvate. Compounds described herein may form solvates and all such solvates are within the scope of the invention.

Pharmaceutically acceptable salts of the invention compounds are considered within the scope of the present invention. When the compound of the invention has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., formic acid, acetic acid, fumaric acid, oxalic acid, tartaric acid, lactic acid, maleic acid, citric acid, succinic acid, malic acid, methanesulfonic acid, benzenesulfonic acid, and p-toluenesulfonic acid) or acidic amino acids (such as aspartic acid and glutamic acid). When the compound of the invention has an acidic group, such as for example, a carboxylic acid group, it can form salts with metals, such as alkali and earth alkali metals (e.g., $Na^+$, $Li^+$, $K^+$, $Ca_2^+$, $Mg_2^+$, $Zn_2^+$), ammonia, organic amines (e.g., trimethylamine, triethylamine, pyridine, picoline, ethanolamine, diethanolamine, triethanolamine), or basic amino acids (e.g., arginine, lysine and ornithine).

Compounds of Formula I may be synthesized by a variety of techniques known in the art. For example, Scheme 1 shows that aryl and heteroaryl boronic acids may be cross-coupled to 3-halo chromones (e.g., 3-bromochromone) via Suzuki coupling. Typical palladium catalysts, such as Pd(OAch)$_2$, and bases, such as potassium carbonate maybe used in this transformation. Additional methods for the synthesis of compounds of Formula I include one carbon homologations of deoxybenzoins (Wahala, et al., *J. Chem. Soc.-Perkin Trans.* 3005-3008 (1991); Balasubamanian, S, and Nair, M. G., *Synth. Comm.* 30:469-84 (2000); Chang, et al., *J. Agric. Food Chem.*, 42:1869-71 (1994); hereby incorporated by reference in their entireties) and oxidative aryl isomerizations of chalcones induced by thallium(III) (McKillop, et al., *Tet. Lett.*, 5281 (1970); Susse et al., *Helv. Chim. Acta*, 75:457-70 (199)) or hypervalent iodide (Prakash, et al., Synlett, 337-38 (1990); Kawamura et al., *Synthesis*, 2490-96 (2002)).

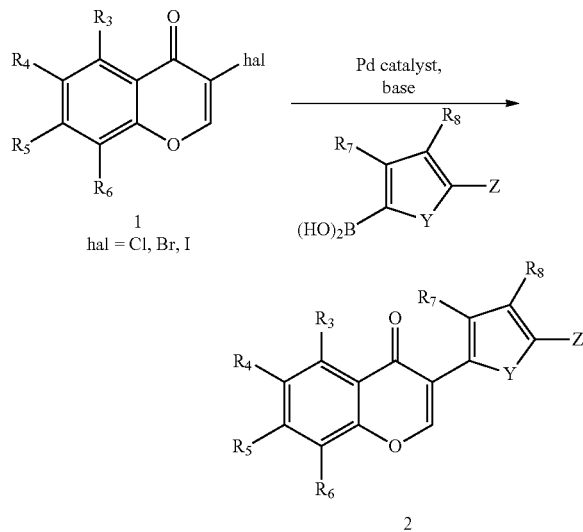

Scheme 1

The resulting compound (2) may be further transformed by, e.g., conjugate addition of cuprates ((R$_1$)$_2$CuLi) to the unsaturated pyranone; imine formation at the ketone with armines (NHR), selective reduction of the ketone to either enantiomer by, e.g., diphenylpyrrolidinemethanol and 9-BBN (Kanth, J. V. B. and Brown, H. C. Tetrahedron, 58:1069-74 (2002)). Quinolone derivatives where X is N rather than O may be made by known methods similar to isoflavones. Traxler, et al., *J. Med. Chem.*, 42:1018-26 (1999); Huang, et al., *Biorg. Med. Chem.*, 6: 1657-62 (1998); Joseph, et al., *Synlett*, 1542-44 (2003).

2. Anti-MEK4 Pathway Antibodies

Described below are exemplary methods of generating anti-MEK4 pathway antibodies for use with the methods and systems of the present invention. The amino acid (and encoding nucleic acid) sequences of targeted human MEK4 pathway proteins, which are useful for generating antibodies, are as follows: MEK4 (NM_003010), p38 MAPK (NM_139013), MAPKAPK2 (NM_004759), HSP27 (NM_001540), and MMP-2 (NM_004530).

(i) Polyclonal Antibodies

The present invention provides polyclonal antibodies directed toward MEK4 pathway proteins for use in the systems and methods of the present invention. Polyclonal antibodies are preferably raised in animals by multiple subcutaneous (sc) or intraperitoneal (ip) injections of the relevant antigen and an adjuvant. It may be useful to conjugate the MEK4 pathway protein or portion thereof to a protein that is immunogenic in the species to be immunized (e.g. keyhole limpet hemocyanin, serum albumin, bovine thyroglobulin, or soybean tyrpsin inhibitor) using a bifunctional or derivitizing agent (e.g. maleimidobenzoyl sulfosuccinimide ester for conjugation through cystein residues, N-hydroxysuccinimide for conjugation through lysine residues, glutaraldehyde, succinic anhydride, SOCl$_2$, or R1N=C=NR, where R and R1 are different alkyl groups.

Examples of a general immunization protocol for a rabbit and mouse are as follows. Animals are immunized against a MEK4 pathway protein, MEK4 pathway protein-conjugates, or derivatives by combining, for example, 100 µg or 5 µg of the protein or conjugate (e.g. for a rabbit or mouse respectively) with 3 volumes of Freund's complete adjuvant and injecting the solution intradermally at multiple sites. One month later the animals are boosted with ⅕ or ⅒ the original amount of peptide or conjugate in Freund's complete adjuvant by subcutaneous injection at multiple sites. Seven to fourteen days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. In addition, aggregating agents such as alum are suitably used to enhance the immune response.

(ii) Monoclonal Antibodies

The present invention provides monoclonal antibodies that are specifically directed to MEK4 pathway proteins for use in the systems and methods of the present invention. Monoclonal antibodies may be made in a number of ways, including using the hybridoma method (e.g. as described by Kohler et al., Nature, 256: 495, 1975, herein incorporated by reference), or by recombinant DNA methods (e.g., U.S. Pat. No. 4,816,567, herein incorporated by reference).

In the hybridoma method, a mouse or other appropriate host animal, such as a hamster or macaque monkey, is immunized to elicit lymphocytes that produce or are capable of producing antibodies that will specifically bind to a MEK4 pathway protein. Alternatively, lymphocytes may be immunized in vitro. Lymphocytes then are fused with myeloma cells using a suitable fusing agent, such as polyethylene glycol, to form a hybridoma cell. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (e.g., Kozbor, J. Immunol., 133: 3001 (1984), herein incorporated by reference).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). After hybridoma cells are identified that produce antibodies of the desired specificity, affinity, and/or activity, the clones may be subcloned by limiting dilution procedures and grown by standard methods. Suitable culture media for this purpose include, for example, D-MEM or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies is described in more detail below.

In some embodiments, antibodies or antibody fragments are isolated from antibody phage libraries generated using the techniques described in, for example, McCafferty et al., Nature, 348: 552554 (1990). Clackson et al., Nature, 352: 624-628 (1991) and Marks et al., J. Mol. Biol., 222: 581-597 (1991) describe the isolation of murine and human antibodies, respectively, using phage libraries. Subsequent publications describe the production of high affinity (nM range) human antibodies by chain shuffling (Marks et. al., BioTechnology, 10: 779-783 (1992)), as well as combinatorial infection and in vivo recombination as a strategy for constructing very large phage libraries (e.g., Waterhouse et al., Nuc. Acids. Res., 21: 2265-2266 (1993)). Thus, these techniques, and similar techniques, are viable alternatives to traditional monoclonal antibody hybridoma techniques for isolation of monoclonal antibodies.

Also, the DNA may be modified, for example, by substituting the coding sequence for human heavy- and light-chain constant domains in place of the homologous murine sequences (e.g., U.S. Pat. No. 4,816,567, and Morrison, et al., Proc. Nat. Acad. Sci. USA, 81: 6851 (1984), both of which are hereby incorporated by reference), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized and Human Antibodies

The present invention provides humanized and human antibodies directed toward a MEK4 pathway protein for use in the methods and systems of the present invention. In certain embodiments, a humanized antibody comprises human antibody amino acid sequences together with amino acid residues that are not from a human antibody. In some embodiments, the human sequences in a humanized antibody comprise the framework regions (FRs) and the sequences or residues that are not from a human antibody comprise one or more complementarity-determining regions (CDRs).

The residues in a humanized antibody that are not from a human antibody may be residues or sequences imported from or derived from another species (including but not limited to mouse), or these sequences may be random amino acid sequences (e.g. generated from randomized nucleic acid sequences), which are inserted into the humanized antibody sequence. As noted above, the human amino acid sequences in a humanized antibody are preferably the framework regions, while the residues which are not from a human antibody (whether derived from another species or random amino acid sequences) preferably correspond to the CDRs. However, in some embodiments, one or more framework regions may contain one or more non-human amino acid residues. In cases of alterations or modifications (e.g. by introduction of a non-human residue) to an otherwise human framework, it is possible for the altered or modified framework region to be adjacent to a modified CDR from another species or a random CDR sequence, while in other embodiments, an altered framework region is not adjacent to an altered CDR sequence from another species or a random CDR sequence. In preferred embodiments, the framework sequences of a humanized antibody are entirely human (i.e. no framework changes are made to the human framework).

Non-human amino acid residues from another species, or a random sequence, are often referred to as "import" residues, which are typically taken from an "import" variable domain. Humanization can be essentially performed following the method of Winter and co-workers (e.g., Jones et al., Nature, 321: 522-525 (1986); Riechmann et al., Nature, 332: 323-327 (1988); Verhoeyen et al., Science, 239: 1534-1536 (1988), all of which are hereby incorporated by reference), by substituting rodent (or other mammal) CDRs or CDR sequences for the corresponding sequences of a human antibody. Also, antibodies wherein substantially less than an intact human variable domain has been substituted by the corresponding sequence from a non-human species may also be generated (e.g. U.S. Pat. No. 4,816,567, hereby incorporated by reference). In practice, humanized antibodies are typically human antibodies in which some CDR residues and possibly some FR residues are substituted by residues from analogous sites in rodent antibodies, or, as noted above, in which CDR sequences have been substituted by random sequences. By way of non-limiting example only, methods for conferring donor CDR binding affinity onto an antibody acceptor variable region framework are described in WO 01/27160 A1, herein incorporated by reference.

3. Nucleic Acid Based Agents

In certain embodiments, the present invention provides nucleic acid based agents (e.g., oligonucleotides) that target MEK4 pathway nucleic acids. In certain embodiments, the agents are siRNA molecules. In other embodiments, the agents are antisense molecules. The nucleic acid sequences of targeted human MEK4 pathway proteins, which are useful for generating antibodies, are as follows: MEK4 (NM_003010), p38 MAPK (NM_139013), MAPKAPK2 (NM_004759), HSP27 (NM_001540), and MMP-2 (NM_004530). These sequences can be employed (e.g., using various software packages) to design RNAi and anti-sense sequences that target these genes or other genes of the MEK4 pathway.

i. RNA Interference (RNAi)

In some embodiments, RNAi is utilized to inhibit MEK4 pathway protein function by targeting MEK4 pathway nucleic acid. RNAi represents an evolutionary conserved cellular defense for controlling the expression of foreign genes in most eukaryotes, including humans. RNAi is typically triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC(RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments. In some embodiments, RNAi oligonucleotides are designed to target the junction region of fusion proteins.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl and Borkhardt, Molecular Intervent. 2002; 2(3):158-67, herein incorporated by reference).

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:494-8; Elbashir et al., Genes Dev. 2001; 15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing (Brummelkamp et al, Science 2002; 296:550-3; and Holen et al, Nucleic Acids Res. 2002; 30:1757-66, both of which are herein incorporated by reference).

An important factor in the design of siRNAs is the presence of accessible sites for siRNA binding. Bohula et al., (J. Biol. Chem., 2003; 278: 15991-15997; herein incorporated by reference) describe the use of a type of DNA array called a scanning array to find accessible sites in mRNAs for designing effective siRNAs. These arrays comprise oligonucleotides ranging in size from monomers to a certain maximum, usually synthesized using a physical barrier (mask) by stepwise addition of each base in the sequence. Thus, the arrays represent a full oligonucleotide complement of a region of the target gene. Hybridization of the target mRNA (e.g., MEK4 pathway nucleic acid) to these arrays provides an exhaustive accessibility profile of this region of the target mRNA. Such data are useful in the design of antisense oligonucleotides (ranging from 7mers to 25mers), where it is important to achieve a compromise between oligonucleotide length and binding affinity, to retain efficacy and target specificity (Sohail et al, Nucleic Acids Res., 2001; 29(10): 2041-2045). Additional methods and concerns for selecting siRNAs are described for example, in WO 05054270, WO05038054A1, WO03070966A2, J Mol Biol. 2005 May 13; 348(4):883-93, J Mol. Biol. 2005 May 13; 348(4):871-81, and Nucleic Acids Res. 2003 Aug. 1; 31(15):4417-24, each of which is herein incorporated by reference in its entirety. In addition, software (e.g., the MWG online siMAX siRNA design tool) is commercially or publicly available for use in the selection of siRNAs.

ii. Antisense

In other embodiments, MEK4 pathway protein expression is modulated using antisense compounds that specifically hybridize with one or more MEK4 pathway nucleic acids encoding MEK4 pathway proteins. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA.

It is preferred to target specific nucleic acids for antisense. "Targeting" an antisense compound to a particular nucleic acid (e.g., a MEK4 pathway nucleic acid), in the context of the present invention, is a multistep process. The process usually begins with the identification of a nucleic acid sequence whose function is to be modulated. This may be, for example, a gene (or mRNA transcribed from the gene) in the MEK4 pathway whose expression is associated with a particular disorder or disease state, or a nucleic acid molecule from an infectious agent. In the present invention, the target is a MEK4 pathway nucleic acid molecule encoding a MEK4 peptide or other gene in the p38 MAPK pathway. The targeting process also includes determination of a site or sites within this gene for the antisense interaction to occur such that the desired effect, e.g., detection or modulation of expression of the protein, will result.

Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a tumor antigen of the present invention, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

In some embodiments, target sites for antisense inhibition are identified using commercially available software programs (e.g., Biognostik, Gottingen, Germany; SysArris Software, Bangalore, India; Antisense Research Group, University of Liverpool, Liverpool, England; GeneTrove, Carlsbad, Calif.). In other embodiments, target sites for antisense inhibition are identified using the accessible site method described in PCT Publ. No. WO0198537A2, herein incorporated by reference.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e., from about 8 to about 30 linked bases), although both longer and shorter sequences may find use with the present invention. Particularly preferred antisense compounds are antisense oligonucleotides, even more preferably those comprising from about 12 to about 25 nucleobases.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleotides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science 254:1497 (1991).

Most preferred embodiments of the invention are oligonucleotides with phosphorothioate backbones and oligonucleosides with heteroatom backbones, and in particular —$CH_2$—, —NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$—, and —O—N($CH_3$)—$CH_2$—$CH_2$— (wherein the native phosphodiester backbone is represented as —O—P—O—$CH_2$—) of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, S$CH_3$, OCN, Cl, Br, CN, $CF_3$, O$CF_3$, SO$CH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethyl (2'-O—$CH_2CH_2OCH_3$, also known as 2'-O-(2-methoxyethyl) or 2'-MOE) (Martin et al., Helv. Chim. Acta 78:486 [1995]) i.e., an alkoxyalkoxy group. A further preferred modification includes 2'-dimethylaminooxyethoxy (i.e., a O($CH_2$)$_2$ON($CH_3$)$_2$ group), also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$.

Other preferred modifications include 2'-methoxy(2'-O—$CH_3$), 2'-aminopropoxy(2'-O$CH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2. ° C. and are presently preferred base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-S-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisense oligonucleotides described above. Any suitable modification or substitution may be utilized.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above. The present invention also includes pharmaceutical compositions and formulations that include the antisense compounds of the present invention as described below.

In certain embodiments, the antisense sequences employed in the methods, compositions, and systems of the present invention are selected from the following:

```
5'-TTCCTCCTTTGTCTCCCAGC-3';     (SEQ ID NO: 1)

5'-ATTCCTCCTTTGTCTCCCAG-3';     (SEQ ID NO: 2)

5'-ATTCCTCCTTTGTCTCCCA-3';      (SEQ ID NO: 3)

5'-GCCTCTTTATCACCTACCACA-3';    (SEQ ID NO: 4)

5'-AAUUCCTCCTTTGTCUCCCA-3';     (SEQ ID NO: 5)

5'-GUCUCTCTATGTGTGGGUUU-3';     (SEQ ID NO: 6)

5'-UGUGUGTTCTCAGTCUCUCU-3';     (SEQ ID NO: 7)

5'-CUCCUCGTCCAATTTCUCCA-3';     (SEQ ID NO: 8)
and

5'-GGCUUGCTGTGGTCGAAGGC-3'.     (SEQ ID NO: 9)
```

Another use of oligonucleotides of the present invention involves direct contact between at least one oligonucleotide and at least one protein to form an aptameric interaction. Such an interaction may inhibit or otherwise affect the activity of a desired protein or proteins, such as MEK4 or MEK4 pathway members (see e.g., U.S. Pat. Nos. 5,998,596; 5,270,163; 5,567,588; 5,595,877; 5,660,985; 5,696,249; 5,763,177; 5,817,785; 6,001,577; 6,184,364; 6,344,318; 6,376,190; 6,482,594; Bergan et at (1994) Nucleic Acids Res. 22:2150-54; Bergan et at (1995) Antisense Res. Dev. 5:33-8; Tuerk and Gold (1990) Science 249:505-10; Burke and Gold (1997) Nucleic Acids Res 25:2020-4; Brody et at (1999) Mol. Diagn. 4:381-88; Brody and Gold (2000) Rev. Mol. Biotechnol. 74:5-13; each herein incorporated by reference in their entireties).

4. Therapeutic Formulations and Uses

In some embodiments, the present invention provides therapeutic formulations comprising anti-MEK4 pathway agents (e.g., anti-MEK4 pathway antibodies, MEK4 pathway small molecules, and MEK4 pathway RNAi or antisense). It is not intended that the present invention be limited by the particular nature of the therapeutic composition. For example, such compositions can include an anti-MEK4 pathway agent, provided together with physiologically tolerable liquids, gels, solid carriers, diluents, adjuvants and excipients, and combinations thereof (See, e.g, Remington's Pharmaceutical Sciences 16th edition, Osol, A. Ed. (1980), herein incorporated by reference).

In addition, anti-MEK4 pathway agents may be used together with other therapeutic agents, including, but not limited to, salicylates, steroids, immunosuppressants, antibodies or antibiotics. Particular therapeutic agents which may be used with the anti-MEK4 pathway agents of the present invention include, but are not limited to, the following agents: azobenzene compounds (U.S. Pat. No. 4,312,806, incorporated herein by reference), benzyl-substituted rhodamine derivatives (U.S. Pat. No. 5,216,002, incorporated herein by reference), zinc L-carnosine salts (U.S. Pat. No. 5,238,931, incorporated herein by reference), 3-phenyl-5-carboxypyrazoles and isothiazoles (U.S. Pat. No. 5,294,630, incorporated herein by reference), IL-10 (U.S. Pat. No. 5,368,854, incorporated herein by reference), quinoline leukotriene synthesis inhibitors (U.S. Pat. No. 5,391,555, incorporated herein by reference), 2'-halo-2'deoxy adenosine (U.S. Pat. No. 5,506, 213, incorporated herein by reference), phenol and benzamide compounds (U.S. Pat. No. 5,552,439, incorporated herein by reference), tributyrin (U.S. Pat. No. 5,569,680, incorporated herein by reference), certain peptides (U.S. Pat. No. 5,756,449, incorporated herein by reference), omega-3 polyunsaturated acids (U.S. Pat. No. 5,792,795, incorporated herein by reference), VLA-4 blockers (U.S. Pat. No. 5,932, 214, incorporated herein by reference), prednisolone meta-sulphobenzoate (U.S. Pat. No. 5,834,021, incorporated herein by reference), cytokine restraining agents (U.S. Pat. No. 5,888,969, incorporated herein by reference), p38 inhibitors (Herberich et at (2008) J. Med. Chem. 10.1021/jm8005417; Cuenda et at (1995) FEBS Lett. 364:229-33; Jackson et al (1998) J. Pharmacol. Exper. Therapeutics 284: 687-92; Young et at (1997) J Biol Chem 272:12116-21; Goedert et at (1997) EMBO J 16:3563-71; Buo et at (2005) Bioorg. Medicinal Chem. Lett. 16:64-8; WO/2007/126871; Xu et at (2008) FEBS Lett 8:1276-82; each incorporated herein by reference) and nicotine (U.S. Pat. No. 5,889,028, incorporated herein by reference).

Anti-MEK4 pathway agents may be used together with agents which reduce the viability or proliferative potential of a cell. Agents which reduce the viability or proliferative potential of a cell can function in a variety of ways including, for example, inhibiting DNA synthesis, inhibiting cell division, inducing apoptosis, or inducing non-apoptotic cell killing. Specific examples of cytotoxic and cytostatic agents include but are not limited to, pokeweed antiviral protein, abrin, ricin, and each of their A chains, doxorubicin, cisplastin, iodine-131, yttrium-90, rhenium-188, bismuth-212, taxol, 5-fluorouracil VP-16, bleomycin, methotrexate, vindesine, adriamycin, vincristine, vinblastine, BCNU, mitomycin and cyclophosphamide and certain cytokines such as TNF-α and TNF-β. Thus, cytotoxic or cytostatic agents can include, for example, radionuclides, chemotherapeutic drugs, proteins, and lectins.

"Treating" within the context of the instant invention, means an alleviation, in whole or in part, of symptoms associated with a disorder or disease, or slowing, inhibiting or halting of further progression or worsening of those symptoms, or prevention or prophylaxis of the disease or disorder in a subject at risk for developing the disease or disorder. Thus, e.g., treating metastatic prostate cancer may include inhibiting or preventing the metastasis of the cancer, a reduction in the speed and/or number of the metastasis, a reduction in tumor volume of the metastasized prostate cancer, a complete or partial remission of the metastasized prostate cancer or any other therapeutic benefit. As used herein, a "therapeutically effective amount" of a compound of the invention refers to an amount of the compound that alleviates, in whole or in part, symptoms associated with a disorder or disease, or slows, inhibits or halts further progression or worsening of those symptoms, or prevents or provides prophylaxis for the disease or disorder in a subject at risk for developing the disease or disorder.

A subject is any animal that can benefit from the administration of a compound as described herein. In some embodiments, the subject is a mammal, for example, a human, a primate, a dog, a cat, a horse, a cow, a pig, a rodent, such as for example a rat or mouse. Typically, the subject is a human.

A therapeutically effective amount of a compound as described herein used in the present invention may vary depending upon the route of administration and dosage form. Effective amounts of invention compounds typically fall in the range of about 0.001 up to 100 mg/kg/day, and more typically in the range of about 0.05 up to 10 mg/kg/day. Typically, the compound or compounds used in the instant invention are selected to provide a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

Treatment may also include administering the compounds or pharmaceutical formulations of the present invention in combination with other therapies. Combinations of the invention may be administered simultaneously, separately or sequentially. For example, the compounds and pharmaceutical formulations of the present invention may be administered before, during, or after surgical procedure and/or radiation therapy. Alternatively, the compounds of the invention can also be administered in conjunction with other anticancer agents described herein. The specific amount of the additional active agent will depend on the specific agent used, the type of condition being treated or managed, the severity and stage of the condition, and the amount(s) of compounds and any optional additional active agents concurrently administered to the subject.

In certain embodiments, the present invention provides methods, systems, and compositions for both inhibiting a MEK4 pathway protein or nucleic acid and activating the endoglin-ALK2-Smad1 pathway so as to cause increased expression and/or activation of endoglin, ALK2, and/or Smad1. In certain embodiments, only one pathway is targeted (e.g., only the MEK4 pathway is targeted for inhibition; only the endoglin-ALK2-Smad1 pathway is targeted for activation). While the present invention is not limited to any particular mechanism, it is believed that inhibiting MEK4 signaling pathway and activating the endoglin-ALK2-Smad1 signaling pathway are both related to reducing cancer cell motility, particularly prostate cancer motility. As such, in certain embodiments, the MEK4 pathway inhibition described above is combined with compositions and methods for increasing the expression of endoglin, ALK2, and Smad1 in order to prevent cancer cell metastasis. In certain embodiments, small molecules are employed to increase the expression of proteins in the endoglin-ALK2-Smad1 pathway, such as genistein and genistein analogues (e.g., compounds described herein; e.g., compound 46). In other embodiments, expression vectors encoding endoglin, ALK2, or Smad1 are employed in gene therapy type methods to caused increased expression of the genes encoding these proteins. The nucleic acid sequences encoding endoglin and Smad1 are as follows: endoglin (NM_000118), and Smad1 (NM_001003688). These sequences can be employed to design appropriate expression vectors for causing increased expression of endoglin, ALK2, and Smad1.

In some embodiments of the invention, one or more compounds of the invention and an additional active agent are administered to a subject, more typically a human, in a sequence and within a time interval such that the compound can act together with the other agent to provide an enhanced benefit relative to the benefits obtained if they were administered otherwise. For example, the additional active agents can be co-administered by co-formulation, administered at the same time or administered sequentially in any order at different points in time; however, if not administered at the same time, they should be administered sufficiently close in time so as to provide the desired therapeutic or prophylactic effect. In some embodiments, the compound and the additional active agents exert their effects at times which overlap. Each additional active agent can be administered separately, in any appropriate form and by any suitable route. In other embodiments, the compound is administered before, concurrently or after administration of the additional active agents.

In various examples, the compound and the additional active agents are administered less than about 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In other examples, the compound and the additional active agents are administered concurrently. In yet other examples, the compound and the additional active agents are administered concurrently by co-formulation.

In other examples, the compound and the additional active agents are administered at about 2 to 4 days apart, at about 4 to 6 days apart, at about 1 week part, at about 1 to 2 weeks apart, or more than 2 weeks apart.

In certain examples, the inventive compound and optionally the additional active agents are cyclically administered to a subject. Cycling therapy involves the administration of a first agent for a period of time, followed by the administration of a second agent and/or third agent for a period of time and repeating this sequential administration. Cycling therapy can provide a variety of benefits, e.g., reduce the development of resistance to one or more of the therapies, avoid or reduce the side effects of one or more of the therapies, and/or improve the efficacy of the treatment.

In other examples, the inventive compound and optionally the additional active agent are administered in a cycle of less than about 3 weeks, about once every two weeks, about once every 10 days or about once every week. One cycle can comprise the administration of an inventive compound and optionally the second active agent by infusion over about 90 minutes every cycle, about 1 hour every cycle, about 45 minutes every cycle, about 30 minutes every cycle or about 15 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

Courses of treatment can be administered concurrently to a subject, i.e., individual doses of the additional active agents are administered separately yet within a time interval such that the inventive compound can work together with the additional active agents. For example, one component can be administered once per week in combination with the other components that can be administered once every two weeks or once every three weeks. In other words, the dosing regimens are carried out concurrently even if the therapeutics are not administered simultaneously or during the same day.

The additional active agents can act additively or, more typically, synergistically with the inventive compound. In one example, the inventive compound is administered concurrently with one or more second active agents in the same pharmaceutical composition. In another example, the inventive compound is administered concurrently with one or more second active agents in separate pharmaceutical compositions. In still another example, the inventive compound is administered prior to or subsequent to administration of a second active agent. The invention contemplates administration of an inventive compound and a second active agent by the same or different routes of administration, e.g., oral and parenteral. In certain embodiments, when the inventive compound is administered concurrently with a second active agent that potentially produces adverse side effects including, but not limited to, toxicity, the second active agent can advantageously be administered at a dose that falls below the threshold that the adverse side effect is elicited.

The instant invention also provides for pharmaceutical compositions and medicaments which may be prepared by combining one or more compounds described herein, pharmaceutically acceptable salts thereof, stereoisomers thereof, tautomers thereof, or solvates thereof, with pharmaceutically acceptable carriers, excipients, binders, diluents or the like to inhibit or treat primary and/or metastatic prostate cancers. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, or via implanted reservoir. Parenteral or systemic administration includes, but is not limited to, subcutaneous, intravenous, intraperitoneal, and intramuscular injections. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or antioxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is nonvolatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

For rectal administration, the pharmaceutical formulations and medicaments may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Compounds of the invention may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. Formulations for inhalation administration contain as excipients, for example, lactose, polyoxyethylene-9-lauryl ether, glycocholate and deoxycholate. Aqueous and nonaqueous aerosols are typically used for delivery of inventive compounds by inhalation.

Ordinarily, an aqueous aerosol is made by formulating an aqueous solution or suspension of the compound together with conventional pharmaceutically acceptable carriers and stabilizers. The carriers and stabilizers vary with the requirements of the particular compound, but typically include non-ionic surfactants (TWEENs, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions. A nonaqueous suspension (e.g., in a fluorocarbon propellant) can also be used to deliver compounds of the invention.

Aerosols containing compounds for use according to the present invention are conveniently delivered using an inhaler, atomizer, pressurized pack or a nebulizer and a suitable propellant, e.g., without limitation, pressurized dichlorodifluoromethane, trichlorofluoromethane, dichlorotetrafluoroethane, nitrogen, air, or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch. Delivery of aerosols of the present invention using sonic nebulizers is advantageous because nebulizers minimize exposure of the agent to shear, which can result in degradation of the compound.

For nasal administration, the pharmaceutical formulations and medicaments may be a spray, nasal drops or aerosol containing an appropriate solvent(s) and optionally other compounds such as, but not limited to, stabilizers, antimicrobial agents, antioxidants, pH modifiers, surfactants, bioavailability modifiers and combinations of these. For administration in the form of nasal drops, the compounds maybe formulated in oily solutions or as a gel. For administration of nasal aerosol, any suitable propellant may be used including compressed air, nitrogen, carbon dioxide, or a hydrocarbon based low boiling solvent.

Dosage forms for the topical (including buccal and sublingual) or transdermal administration of compounds of the invention include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Transdermal patches have the added advantage of providing controlled delivery of a compound of the invention to the body. Such dosage forms can be made by dissolving or dispersing the agent in the proper medium. Absorption enhancers can also be used to increase the flux of the inventive compound across the skin. The rate of such flux can be controlled by either providing a rate controlling membrane or dispersing the compound in a polymer matrix or gel.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

The formulations of the invention may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present invention, thus generally described, will be understood more readily by reference to the following examples, which are provided by way of illustration and are not intended to be limiting of the present invention.

EXAMPLES

Example 1

MEK expression was examined in six human prostate cancer (PCa) cell lines: PC3 and PC3-M metastatic PCa cells, 1532CPTX and 1542 CPTX immortalized localized PCa cells, and 1532 NPTX and 1542 NPTX immortalized normal epithelial cells. The last four cell lines are primary cells, are HPV transformed, and thus represent early stages of prostate carcinogenesis. They provide representative members of the metastatic phenotype, as well as members of early state phenotypes. (Liu et. al., "Prostate cancer chemoprevention agents exhibit selective activity against early stage prostate cancer cells," *Prostate Cancer Prostatic Dis.* 2001, 4: 81-91, herein incorporated by reference in its entirety). All six cell lines also secrete as well as respond to TGFβ, a regulator of cell motility that plays a role in PCa cell invasiveness.

A Western blot analysis of the six cell lines was performed. MEK Western blot analyses used identical amounts of protein and were exposed at the same time, allowing for comparison.

Results are shown in FIG. 1. MEK4 expression is high in all six cell lines, while MEK3 and MEK6 expression is low and variable.

Example 2

The invasiveness of the PCa cell lines used in Example 1 was assessed in the absence and in the presence of genistein. Assays were conducted using methods as described in Craft et al. (2008, Mol. Pharmacol., 73(1):235-242; herein incorporated by reference in its entirety).

The results of this assay are presented in FIGS. 2A and 2B. FIG. 2A shows that early stage PCa cells are less invasive than metastatic PC3-M cells. FIG. 2B shows that genistein inhibits invasion of both early and late stage PCa cells.

Example 3

Figure 3:
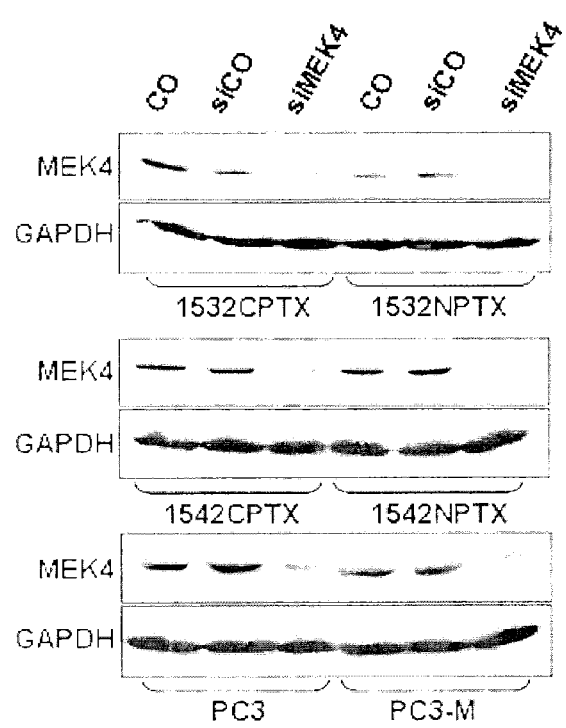
FIGS. 3A, 3B, 3C and 3D show results of experiments assessing the pharmacological relevance of MEK4 as a target for prostate cancer therapy.
Figure 3:
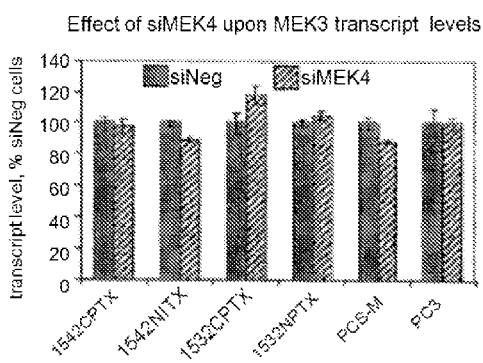
Figure 3:
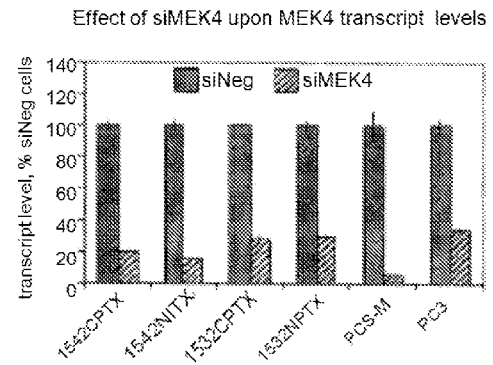

To show that MEK4 is a pharmacologically relevant target of genistein, a MEK4 knockdown experiment with MEK4 siRNA (siMEK4) was conducted using standard techniques. Results shown in FIG. 3A demonstrate that siMEK4 suppresses expression of MEK4 protein relative to non-targeting siRNA and untransfected controls. As a further control, the same human PCa cell lines were transfected with siMEK4 or non-targeting siNeg, and MEK3 and MEK4 transcript levels were measured using quantitative RT/PCR (values normalized to GAPDH). FIG. 3B shows that siMEK4 had no effect on MEK3 transcript levels, while FIG. 3C shows that siMEK4 significantly reduced MEK4 transcript levels in the same cells. Thus, the results show that siMEK4 is specific for MEK4 and does not suppress the homologous MEK3. (MEK6 is not expressed in most of these cell lines and was not examined).

Figure 3D:
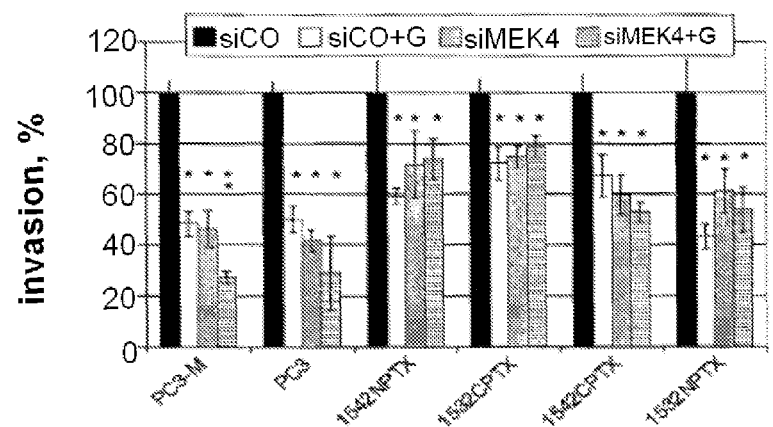

The invasiveness of PCa cells in the presence genistein and siMEK4 was examined. FIG. 3D shows that when MEK4 expression was suppressed by siMEK4, the effect of genistein was abrogated.

Example 4

Figure 7:
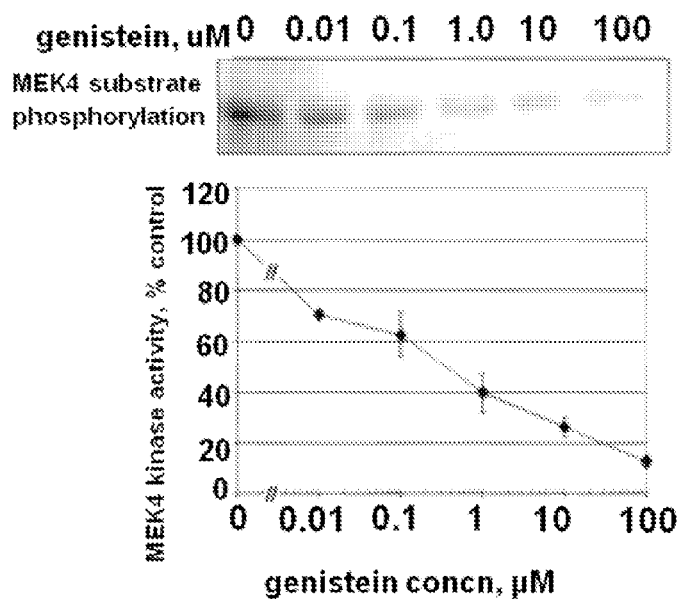
FIG. 7 shows the inhibition of MEK4 kinase activity by genistein in vitro.

Phosphorylation by MEK4 (FIG. 4A) and phosphorylation of MEK4 (FIG. 7) was assayed. The Upstate Biotechnology MEK4 assay system was used to measure inhibition of MEK4 activity. Phosphorylation of MEK4 in vivo was assayed using standard techniques. The $IC_{50}$ of genistein with regard to inhibition of phosphorylation under these conditions is estimated to be less than 0.1 µM.

FIG. 4A shows that genistein inhibits phosphorylation of JNK3 by MEK4 in vitro. FIG. 4B demonstrates that TGFβ increases MEK4 phosphorylation in vivo but that genistein does not block such phosphorylation.

Example 5

The ability of genistein to inhibit human PCa metastasis was examined using the following procedure. Inbred four-week old male athymic mice (Charles River Laboratories), were fed soy-free Harlan Teklad 20168 chow containing 0, 100, or 250 mg genistein/kg chow, beginning one week prior to implantation of $10^6$ human PC3-M PCa cells into the dorsal lobe of the prostate. Mice were necropsied four weeks later. There were 5 mice in each of the three dosing cohorts per experiment, X2 separate experiments which gave essentially identical outcomes, for a total of 30 mice. The resultant blood concentrations of total genistein were measured as described (Takimoto, et al. "Phase I pharmacokinetic and pharmacodynamic analysis of unconjugated soy isoflavones administered to individuals with cancer," Cancer Epidemiol. Biomarkers Prevo 12:1213-21 (2003); herein incorporated by reference in its entirety), and were below the limits of quantitation (for controls), 290±72 nM (100 mg cohort), and 1307±507 nM (250 mg cohort). Knowing that free genistein is about a tenth of the total gives estimated free concentrations of 29 nM and 131 nM. Such concentrations approximate the mean free concentrations reported in the blood of soy consuming Japanese men (Adlercreutz, et al., "Plasma concentrations of phyto-oestrogens in Japanese men," Lancet, 342:1209-10 (1993); herein incorporated by reference in its entirety) and in men after prospective dosing with supradietary amounts of genistein (Takimoto, et al., Cancer Epidemiol. Biomarkers Prevo 12:1213-21 (2003); herein incorporated by reference in its entirety).

As shown in FIG. 5A, genistein decreased metastasis but not tumor volume in a dose dependent fashion. There was no difference in the weight of mice between cohorts. Western blot analysis of fresh frozen primary tumor tissue revealed that genistein increased the level of total p38 MAP kinase protein, but decreased its phosphorylation, as shown in FIG. 5B. The increase in "promotility" proteins likely represents a compensatory response by inherently metastatic cells to therapy which inhibits their motility. These findings demonstrate that genistein inhibits human PCa metastasis in a dose-responsive fashion in vivo at concentrations attained in the blood of men. Importantly, genistein still blocked the activation of p38 MAP kinase, even in the face of up-regulation. Finally, both in vivo and in vitro studies support dose escalation as a viable strategy for inhibiting metastasis of human prostate cancer.

Example 6

Change in cell morphology is a generally recognized measure of change in cell adhesion. Compounds which increase cell adhesion of prostate cancer cells in vivo may inhibit prostate cancer metastasis. This is because an increase in cell adhesion represents a decrease in cell detachment, and in order to metastasize, cells must first detach. The effect of genistein on cell detachment was investigated in vivo. Quantitative image analysis according to established methods was used to measure in vivo changes in nuclear morphology in the prostate. (Bartels, et al., Prostate, 48:144-55, (2001); Boone, et al., Urology, 57:129-31 (2001); Bartels, et al., Anal. Quant. Cytol. Histol. 20:397-406 (1998); Bartels et al., Anal. Quant. Cytol. Histol. 20:389-96; Veltri, et al., J. Cell Biochem. Suppl., 151-57 (2000); herein incorporated by reference in their entireties).

Mouse:

From the mouse experiment of Example 5, primary (prostate gland) and metastatic (local lymph nodes) tissue was Feulgen-stained, and the nuclear morphology of PC3M cells was quantitated on a ChromaVision ACIS® II Image Analysis System. Over 500 cells for each tissue type from mice treated with 250 mg genistein (N=5) or controls (N=5) were scored in a blinded fashion. Genistein was thereby shown to increase nuclear flattening in vivo. Specifically, for lymph node: cell area increased by 19.5±2.1%, cell length by 9.1±1.1%, and cell width by 9.5±1.1% (p:S 0.01 for all). For primary tumor: cell length increased by 3.0±1.1% (p:S 0.05). Thus, genistein induces nuclear flattening in vivo, a marker indicative of decreased cell detachment.

Humans:

Genistein was administered to men with prostate cancer in a phase 1 pharmacokinetic/pharmacodynamic study of genistein, (Takimoto, et al. Cancer Epidemiol. Biomarkers Prev., 12:1213-21 (2003) herein incorporated by reference in its entirety), and a phase 2 study biomarker based study.

Phase 1 study: Doses from 2 to 8 mg genistein/kg (i.e., 2-32× dietary doses; considering that estimates of average daily genistein consumption by soy consumers ranges from 0.3 to 1 mg/kg) were administered to men with prostate cancer. Key findings include that: genistein was well tolerated, peak concentrations of total and free genistein ranged from 4.3-16.3 nM and 66-170 nM, respectively (i.e., >90% of blood genistein was conjugated, and thus inactive), halflife was 15-22 hrs, and clearance was not altered by body mass. These findings demonstrate that administration of genistein to a cohort of older men gives blood concentrations of free genistein associated with anti-metastatic efficacy in preclinical models.

Figure 8:
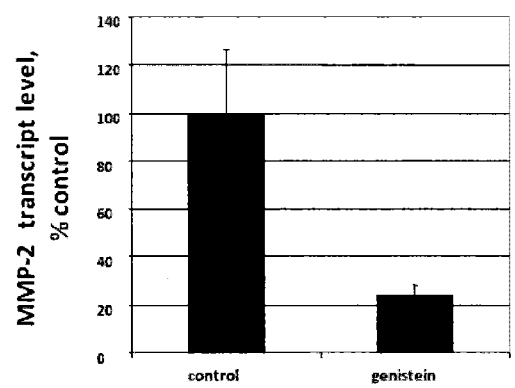
FIG. 8 shows Matrix Metalloprotein-2 (MMP-2) transcript levels in normal prostate epithelial cells from human patients treated or untreated with genistein. Transcript levels were determined using quantitative RT-PCR.

Phase 2 study: A Phase 2 trial of genistein in men with localized prostate cancer was conducted. Men were randomized (1:1) to treatment, or not, with 2 mg genistein/kg/day prior to radical prostatectomy (i.e., ~2-8× average dietary dose). Genistein was given as a single pill/day for 1 month prior to surgery, using the same formulation used in the Phase 1 study (90% genistein; ~0% daidzein, and thus no equol produced in people; Takimoto, C. H., et al, Cancer Epidemiol Biomarkers Prev, 2003, 12(11 Pt 1): p. 1213-21; herein incorporated by reference in its entirety). The mean±SEM trough concentration of free genistein for genistein treated and control subjects in the Phase 2 study was 26.6±6.6 nM and below detection, respectively. Of 38 subjects completing the study, MMP-2 expression was analyzed in tissue from 12 genistein-treated subjects and 12 controls. Patient characteristics did not differ between treatment and control cohorts (Table 1). MMP-2 expression was measured by removing normal prostate epithelial cells from intact fresh frozen prostate tissue by laser capture microdissection (LCM), isolating RNA, treating with DNase, assessing RNA quality by capillary electrophoresis, and measuring MMP-2 transcript levels by qRT/PCR (normalizing to GAPDH), using exon spanning primers. Genistein decreased MMP-2 to 24±4.1% of controls (mean±SEM; 2 sided t test p value=0.045) (FIG. 8).

TABLE 1

Study subject characteristics

| | treatment | | control | | p value* |
|---|---|---|---|---|---|
| subjects, number | 12 | | 12 | | |
| age, mean (range) | 57 | (44-67) | 58 | (48-73) | NS |
| race | | | | | |
| caucasian, number (%) | 9 | 75 | 9 | 75 | NS |
| African American, number (%) | 2 | 17 | 2 | 17 | NS |
| other, number (%) | 1 | 8 | 1 | 8 | NS |
| clinical stage | | | | | |
| T1, number (%) | 7 | 58 | 6 | 50 | NS |
| T2, number (%) | 4 | 33 | 4 | 33 | NS |
| unknown, number (%) | 1 | 8 | 2 | 17 | NS |
| PSA, mean (SEM) | 6 | 0.57 | 6 | 0.61 | NS |

TABLE 1-continued

Study subject characteristics

| | treatment | | control | | p value* |
|---|---|---|---|---|---|
| Gleason score | | | | | |
| 6, number (%) | 7 | 58 | 7 | 58 | NS |
| 7, number (%) | 5 | 42 | 5 | 42 | NS |
| pre-surgery treatment time, mean wks (SEM) | 4 | 0.6 | N/A** | N/A | |
| serious adverse events¶, number | | 0 | | 0 | NS |

*2 sided t test p values > 0.05 are considered not significant (NS) for differences between treatment and control cohorts
**N/A not applicable
¶grade >/= 2 clinical toxicity according to the NCI Common Toxicity Criteria v 2.0

The effect of genistein upon the nuclear morphology of prostate epithelial cells was investigated similarly as for the mouse cells. Genistein induces flattening of "normal" prostate epithelial cells in man. Though morphologically "normal," these cells are present within organs with PCa, have pre-cancer molecular changes, and represent an appropriate target cell type for therapy that inhibits a process associated with PCa progression, in this case, development of the metastatic phenotype. Quantitative image analysis of nuclear morphology of >1000 cells per treatment cohort were scored from 6 genistein treated men, and 5 controls. Genistein increased: length by 1.5±0.7% (p<0.01), width by 2.7±0.7% (p<0.01), and area by 2.0±1.0% (this was only a trend; p=0.15). These studies indicate that genistein is inhibiting the detachment of prostate epithelial cells in man. These findings are consistent with its effects in vitro and in mice. They demonstrate that genistein is therapeutically inhibiting in a man a cellular process, in a relevant target cell type, linked to the development of metastasis.

The effects of genistein on genes which regulate cell motility were investigated using known techniques in gene array technology. (Jovanovic, et al., Am. J. Pharmacogenomics, 1: 145-52 (2001); Jovanovic, et al., Cancer Treat. Res., 113:91-111 (2002); Ding, et al., Prostate Cancer Prostatic Dis., 9:379-91 (2006); herein incorporated by reference in its entirety). In particular, methodology was employed wherein prostate epithelial cells are selectively removed from human prostate tissue by laser capture microdissection (LCM), the resultant RNA linear amplified, and custom manufactured 12K gene arrays are probed. Ding, et al., Id. This methodology was applied to 14 control and 10 genistein-treated subjects on the phase 2 trial, using statistical methods previously described (Jovanovic, et al., J. Probability, Statistics, and Quant. Management, 1:51-60 (2004), Ding, et al., Id.; herein incorporated by reference in their entireties), 6 genes were found to be altered by genistein in a statistically significant fashion (see Table 2). Of these 6 genes, 3 (or ½) have direct links to cell motility in other cell types. Specifically, heparin cofactor II (HCF2) induces formation of filamentous-actin and promotes cell migration (Hoffman, et al., Biochim. Biophys. Acta, 1095:78-82 (1995)), brain acid soluble protein 1 (BASP1) binds to the actin cytoskeleton and regulates its dynamic function (Frey et al., J. Cell Biol., 149:1443-54 (2000); Laux et al., J. Cell Biol., 149:1455-72 (2000); Wiederkehr et al., Exp. Cell Res., 236:103-16 (1997); herein incorporated by reference in its entirety), and MALAT1 (metastasis associated in lung adenocarcinoma transcript) is uniquely over expressed in metastatic lung cancer (Ji, et al., Oncogene 22:8031-41 (2003); herein incorporated by reference in its entirety). Further studies therefore focused upon the 3 motility-associated genes.

TABLE 2

Expression Levels of Genistein Responsive Genes

| gene¶ | gene array data | | | qRT/PCR confirmation** | |
|---|---|---|---|---|---|
| | mean (SE) | | ratio | | ratio |
| | genistein | control | gem/co | p value | geni/co |
| sorbitol dehydrogenase | 5.33 (0.59) | 1.45 (0.34) | 3.68 | — | — |
| prostate acid phosphatase | 6.85 (0.49) | 3.38 (0.45) | 2.03 | — | — |
| brain acid-soluble protein 1 | 13.3 (0.34) | 6.4 (0.69) | 2.08 | 0.0003 | 2.38 |
| heat shock protein 90 | 8.51 (0.5) | 4.25 (0.78) | 2 | — | — |
| MALAT1* | 8.22 (0.87) | 3.88 (0.77) | 2.12 | 0.001 | 2.7 |
| hepatin cofactor II | 2.19 (0.21) | 6.74 (1.06) | 0.32 | 0.006 | 0.22 |

Figure 6:
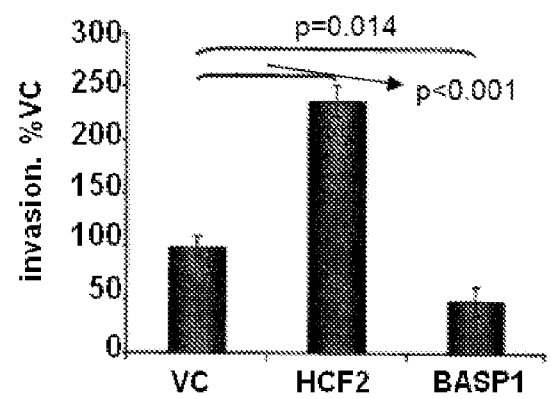
FIG. 6 is a graph showing that genes affected by genistein in man regulate cell motility in human prostate epithelial cells. Expression of HCF2 was decreased and expression of BASP1 was increased by genistein in man. In vitro, they lead to differences in invasion.

*metastasis associated in lung adenocarcinoma transcript
**prostate tissue was re-micro dissected by LCM, RNA isolated, and used directly for qRT/PCR analysis; gene expression was normalized to that of GAPDH.
¶underlined genes have been reported to regulate cell motility Gene array findings were first confirmed: all frozen tissues were re-cut from 24 subjects, LCM re-performed and scaled up to increase RNA yield, and qRT/PCR performed for each gene (and GAPDH for normalization) on each subject (Table 2). Functional studies were next performed, and focused upon HCF2 and BASP1. Over expression of HCF2 and BASP1 in PC3-M cells led to increased and decreased invasion, respectively, as shown in FIG. 6. Expression was confirmed by Western (not shown). It would be expected that an effective antimetastatic drug would decrease HCF2, and increase BASP1, and this is exactly what genistein does in man. Thus, this non-biased screening method selectively identified motility-associated genes provides a rigorous second independent measure of genistein's antimotility action in humans.

Example 7

Using procedures set forth in the Detailed Description and using the appropriate starting materials, the following compounds were made or purchased commercially (compounds 8, 9, 10, and 11). Exemplary synthesis of compounds 5, 12, and 14-16 is as described herein.

| Compound | Structure | $R_5$ | $R_3$ | Z | $R_{10}$ | $R_9$ | Dbl |
|---|---|---|---|---|---|---|---|
| 1 | 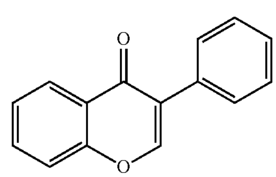 | H | H | H | H | H | + |
| 2 | 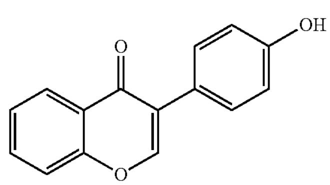 | H | H | OH | H | H | + |
| 3 | 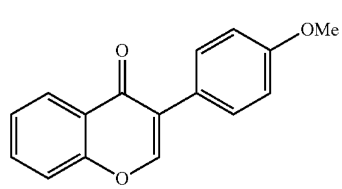 | H | H | OMe | H | H | + |

-continued
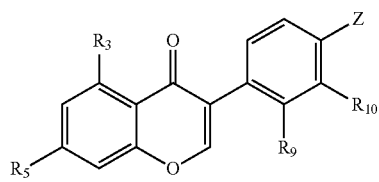
| Compound | Structure | $R_5$ | $R_3$ | Z | $R_{10}$ | $R_9$ | Dbl |
|---|---|---|---|---|---|---|---|
| 4 | 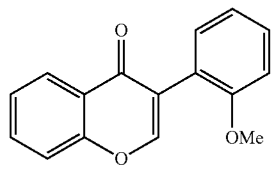 | H | H | H | H | OMe | + |
| 5 | 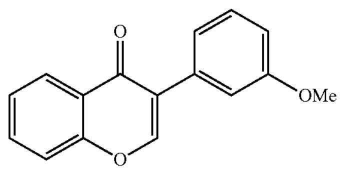 | H | H | H | OMe | H | + |
| 6 | 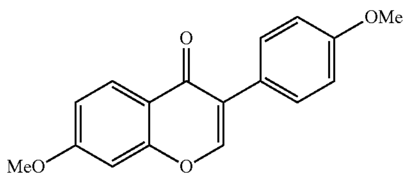 | OMe | OMe | H | OMe | H | + |
| 7 | 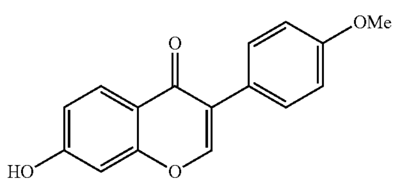 | OH | OMe | H | OMe | H | + |
| 8 | 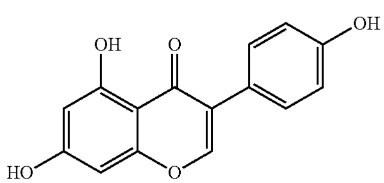 | OH | OH | OH | OH | H | + |
| 9 | 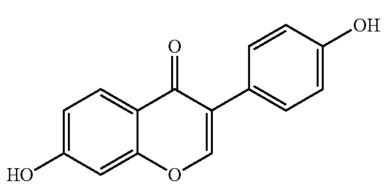 | OH | OH | H | OH | H | + |
| 10 | 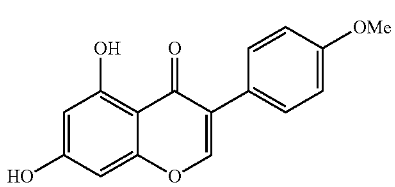 | OH | OMe | OH | OMe | H | + |

-continued

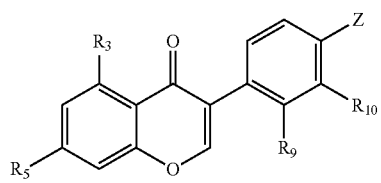

| Compound | Structure | R₅ | R₃ | Z | R₁₀ | R₉ | Dbl |
|---|---|---|---|---|---|---|---|
| 11 | 5,7-dihydroxy-2-(4-hydroxyphenyl)chromone structure | OH | OH | OH | H | H | + |
| 12 | 7-methoxy-3-(4-hydroxyphenyl)chromone structure | OMe | H | OH | H | H | + |
| 13 | 5-methoxy-3-(4-methoxyphenyl)chromone structure | H | OMe | OMe | H | H | + |
| 14 | 5,7-dimethoxy-3-(4-methoxyphenyl)chromone structure | OMe | OMe | OMe | H | H | + |
| 15 | 5-hydroxy-7-methoxy-3-(4-hydroxyphenyl)chromone structure | OH | OMe | OH | H | H | + |
| 16 | 5-hydroxy-7-methoxy-3-(4-methoxyphenyl)chromone structure | OMe | OMe | OMe | H | H | + |
| 21 | 5,7-dimethoxy-3-(4-methoxyphenyl)chromanone structure | OMe | OMe | OMe | H | H | − |

-continued
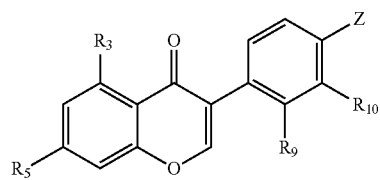
| Compound | Structure | $R_5$ | $R_3$ | Z | $R_{10}$ | $R_9$ | Dbl |
|---|---|---|---|---|---|---|---|
| 22 | 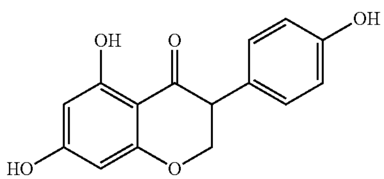 | OH | OH | OH | H | H | − |
| 23 | 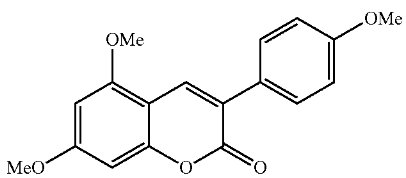 | OMe | OMe | OMe | H | H | − |
| 24 | 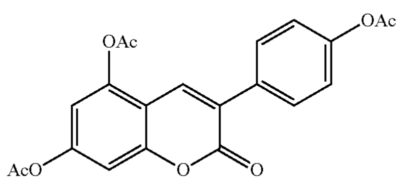 | OAc | OAc | OAc | H | H | − |
| 25 | 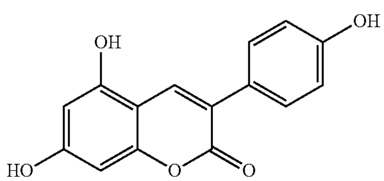 | OH | OH | OH | H | H | −? |
| 26 | 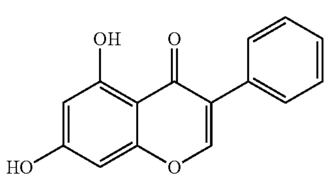 | OH | OH | H | H | H | +? |
| 31 | 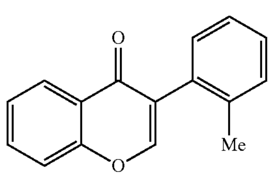 | H | H | H | H | Me | + |
| 32 | 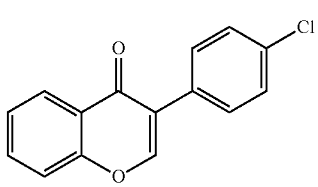 | H | H | Cl | H | H | + |

-continued
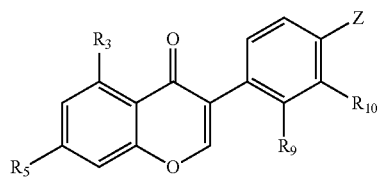
| Compound | Structure | $R_5$ | $R_3$ | Z | $R_{10}$ | $R_9$ | Dbl |
|---|---|---|---|---|---|---|---|
| 33 | 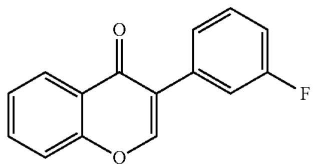 | H | H | H | F | H | + |
| 34 | 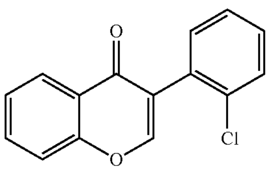 | H | H | H | H | Cl | + |
| 35 | 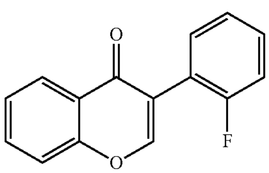 | H | H | H | H | F | + |
| 36 | 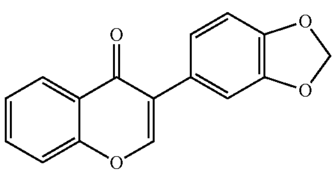 | H | H | OC | O | H | + |
| 37 | 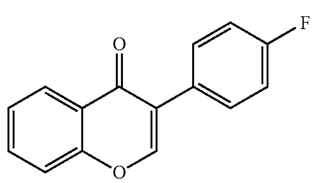 | H | H | F | H | H | + |
| 38 | 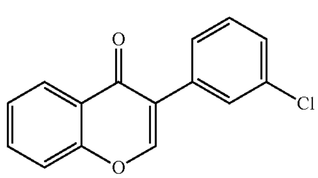 | H | H | H | Cl | H | + |
| 41 | 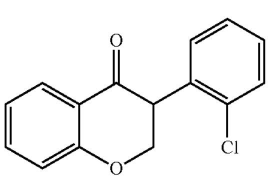 | H | H | H | H | Cl | − |

-continued
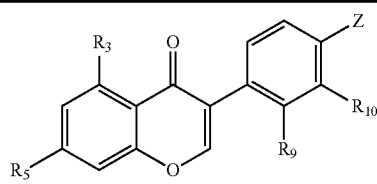
| Compound | Structure | R5 | R3 | Z | R10 | R9 | Dbl |
|---|---|---|---|---|---|---|---|
| 42 | 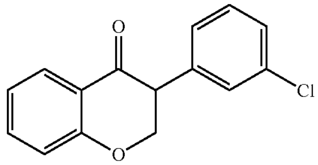 | H | H | H | Cl | H | — |
| 43 | 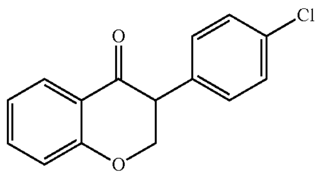 | H | H | Cl | H | H | — |
| 44 | 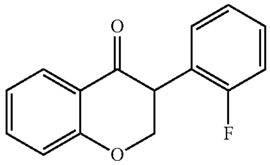 | H | H | H | H | F | — |
| 45 | 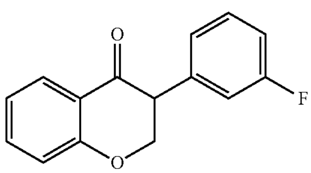 | H | H | H | F | H | — |
| 46 | | H | H | F | H | H | — |
| 47 | | H | H | H | OMe | H | — |
| 48 | | H | H | OC | O | H | — |
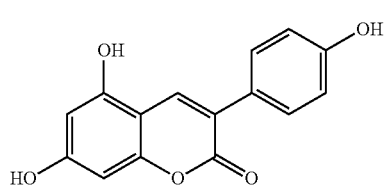
17
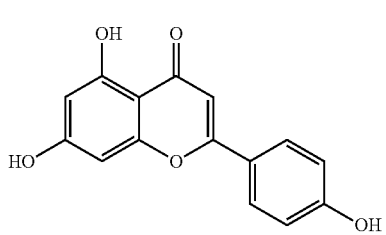
11
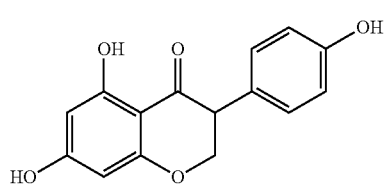
18
-continued
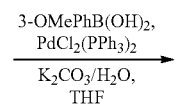
3-OMePhB(OH)₂,
PdCl₂(PPh₃)₂
K₂CO₃/H₂O,
THF

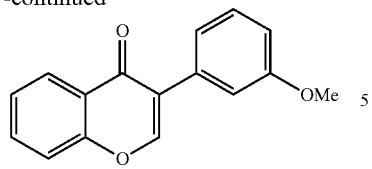

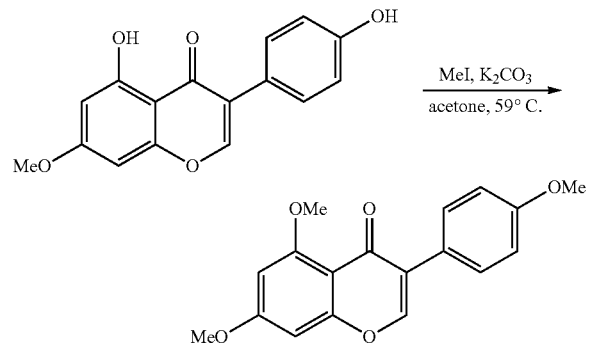

3'-methoxyisoflavone (5).

Prepared using a modified procedure of Hoshino et al. (*Bulletin of the Chemical Society of Japan* 1988, 61, (8), 3008-3010; herein incorporated by reference in its entirety). To a 10 mL round bottom flask was added 3-bromochromone (Gammill, R. B. *Synthesis-Stuttgart* 1979, (11), 901-903; herein incorporated by reference in its entirety) (225 mg, 1 mmol), $K_2CO_3$ (415 mg, 3 mmol), 3-methoxyphenylboronic acid (167 mg, 1.1 mmol), and $PdCl_2(PPh_3)_2$ (21 mg, 0.03 mmol). The flask was equipped with a reflux condenser and purged with $N_2$, followed by addition of $THF/H_2O$ (2.5 mL/0.5 mL). The reaction was stirred at 80° C. for 4 hr. The reaction was then run through a plug of Celite and rinsed with EtOAc. The organic phase was washed with brine and dried over anhydrous $Na_2SO_4$. Purified by flash column chromatography ($SiO_2$, 15% EtOAc/Hex) and recrystallized from $CH_2Cl_2$/Hex to afford 5 (128 mg, 51%) as an off-white solid. Analytical data for isoflavone 5: $^1$H NMR (500 MHz, $CDCl_3$) δ 8.34 (d, J=9.5 Hz, 1H), 8.06 (s, 1H), 7.70 (app t, J=8.5 Hz, 1H), 7.50 (d, J=8.5 Hz, 1H), 7.45 (app t, J=7.5 Hz, 1H), 7.37 (app t, J=8 Hz, 1H), 7.19 (s, 1H), 7.15 (d, J=7 Hz, 1H), 6.96 (d, J=8.5 Hz, 1H), 3.87 (s, 3H); $^{13}$C NMR (125 MHz, $CDCl_3$) δ 176.4, 159.8, 156.4, 153.4, 133.9, 133.4, 129.8, 126.7, 125.5, 124.8, 121.5, 118.3, 114.7, 114.4, 55.6; LCMS: Mass calculated for $C_{16}H_{12}O_3$, [M+H]$^+$, 253. Found 253.

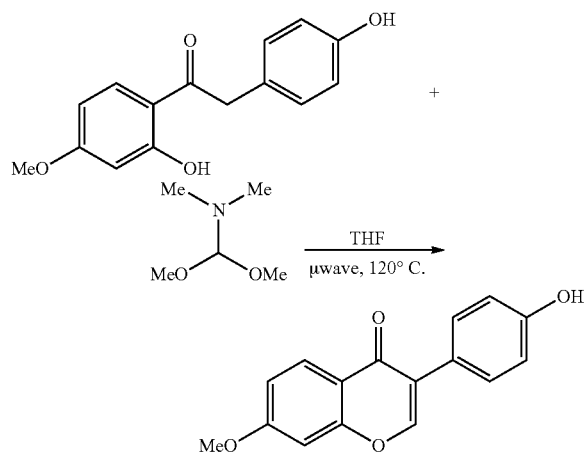

7-methoxydiadzein (12).

To an oven-dried microwave vial was added 4-methoxydeoxybenzoin (73 mg, 2.83 mmol), dimethyl formamide dimethyl acetal (0.188 mL, 1.41 mmol) and THF (0.100 mL). The reaction was heated to 120° C. for 2 min. The product was recrystallized from methanol and a few drops of water to afford 12 (50 mg, 66%) as a pink powder. Analytical data for isoflavone 12: $^1$H NMR (500 MHz, DMSO) δ 9.56 (s, 1H), 8.38 (s, 1H), 8.03 (d, J=9 Hz, 1H), 7.40 (d, J=9 Hz, 2H), 7.16 (s, 1H), 7.08 (d, J=9 Hz, 1H), 6.81 (d, J=9 Hz, 2H), 3.91 (s, 3H); $^{13}$C NMR (125 MHz, DMSO) δ 175.4, 164.3, 158.1, 157.9, 153.9, 130.8, 127.6, 124.4, 123.0, 118.3, 115.7, 115.4, 101.2, 56.8; LCMS: Mass calculated for $C_{16}H_{12}O_4$, [M+H]$^+$, 269. Found 269.

5,7,4'-trimethoxygenistein (14).

To a 100 mL round bottom flask was added genistein (500 mg, 1.85 mmol) and $K_2CO_3$ (1.02 g, 7.4 mmol). The flask was equipped with a reflux condenser and purged with $N_2$. To the flask was added acetone (15 mL) and MeI (0.277 mL), and the reaction was heated to 59° C. Additional $K_2CO_3$ and MeI were added as needed to push the reaction. Upon completion, the reaction was allowed to cool to room temperature and was filtered to remove KI. Purified by flash column chromatography ($SiO_2$, 2% MeOH/$CH_2Cl_2$) to afford 14 (260 mg, 45%) as an off-white solid. Analytical data for isoflavone 14: $^1$H NMR (500 MHz, $CDCl_3$) δ 7.77 (s, 1H), 7.49 (d, J=9 Hz, 2H), 6.94 (d, J=9 Hz, 2H), 6.45 (s, 1H), 6.38 (s, 1H), 3.95 (s, 3H), 3.90 (s, 3H), 3.84 (s, 3H); $^{13}$C NMR (125 MHz, $CDCl_3$) δ 175.7, 164.1, 161.7, 160.2, 159.6, 150.2, 130.6, 126.2, 124.6, 113.9, 110.2, 96.4, 92.7, 56.6, 56.0, 55.5; LCMS: Mass calculated for $C_{18}H_{16}O_5$, [M+H]$^+$, 313. Found 313.

7-methoxygenistein (15).

Prepared according to the general procedure using genistein (300 mg, 1.11 mmol), $K_2CO_3$ (307 mg, 2.22 mmol), acetone and MeI (0.139 mL). Purified by flash column chromatography ($SiO_2$, 1% MeOH/$CH_2Cl_2$) to afford 15 (70 mg, 22%) as an off-white solid. Analytical data for isoflavone 15: $^1$H NMR (500 MHz, DMSO) δ 12.96 (s, 1H), 9.62 (s, 1H), 8.41 (s, 1H), 7.39 (d, J=8.5 Hz, 2H), 6.82 (d, J=8.5 Hz, 2H), 6.65 (s, 1H), 6.41 (s, 1H), 3.86 (s, 3H); $^{13}$C NMR (125 MHz, DMSO) δ 181.1, 165.9, 162.4, 158.2, 158.1, 155.1, 130.9, 123.2, 121.7, 115.8, 106.1, 98.7, 93.1, 56.8; LCMS: Mass calculated for $C_{16}H_{12}O_5$, [M+H]$^+$, 285. Found 285.

7,4'-dimethoxygenistein (16).

Prepared according to the general procedure using genistein (500 mg, 1.85 mmol), $K_2CO_3$ (1.02 g, 7.4 mmol), acetone (15 mL) and MeI (0.277 mL). Purified by flash column chromatography ($SiO_2$, 10% EtOAc/Hex) to afford 16 (270 mg, 49%) as an off-white solid. Analytical data for isoflavone 16: $^1$H NMR (500 MHz, $CDCl_3$) δ 12.88 (s, 1H), 7.88 (s, 1H), 7.48 (d, J=8.5 Hz, 2H), 7.00 (d, J=9 Hz, 2H), 6.41 (d, J=8.5 Hz, 2H), 3.89 (s, 3H), 3.86 (s, 3H); $^{13}$C NMR (125 MHz, $CDCl_3$) δ 181.1, 165.8, 163.0, 160.0, 158.2, 152.9, 130.4, 123.9, 123.2, 114.3, 106.5, 98.4, 92.7, 56.1, 55.6; LCMS: Mass calculated for $C_{17}H_{14}O_5$, [M+H]$^+$, 299. Found 299.

Example 8

Figure 9:
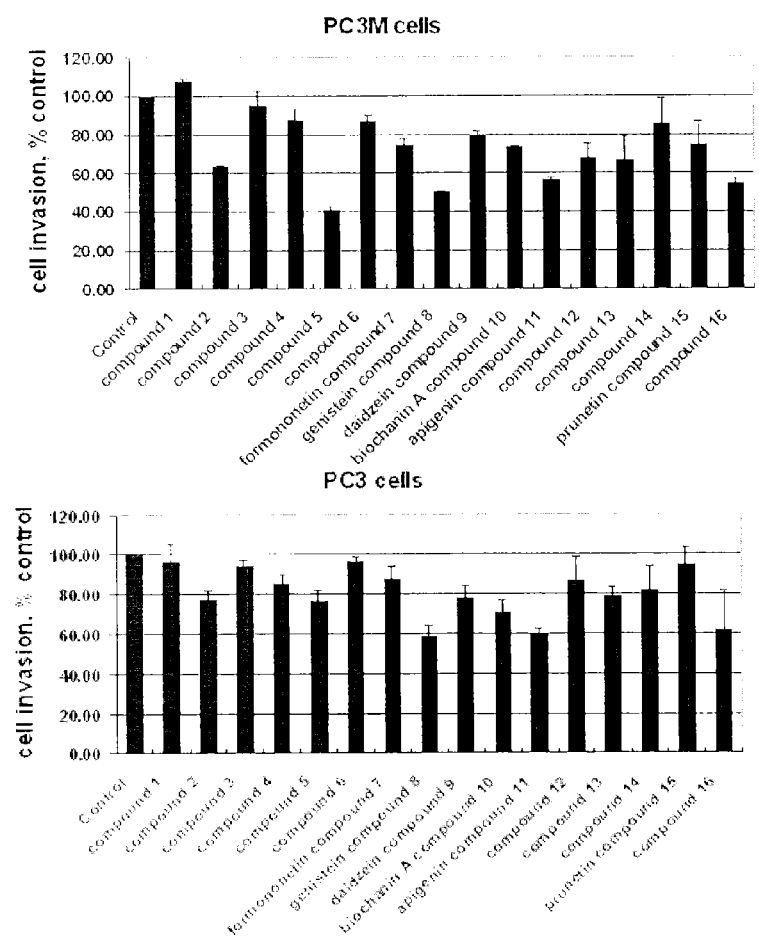
FIG. 9 shows the results of cell invasion assays conducted with Compounds 1-16 using PC3M or PC3 cells according to the method of Example 2.
Figure 10:
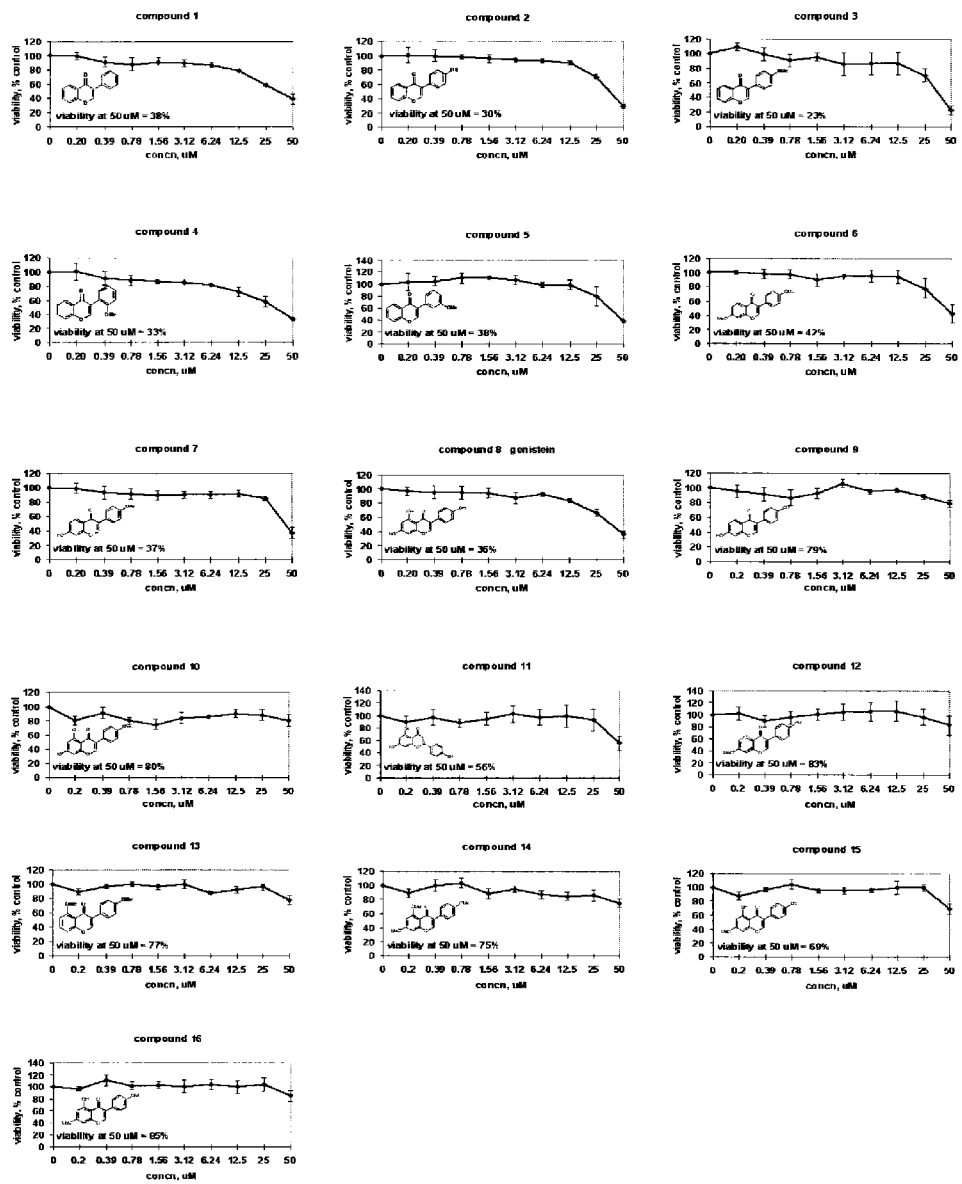
FIG. 10 shows the results of 3-day growth inhibition dimethylthiazol-diphenyltetrazolium bromide (MTT) assays conducted with Compounds 1-16. PC3-M human prostate cancer cells were treated with different concentrations of the indicated compound, and then MTT reduction as an indicator of cell viability was measured according to the method of Example 9.

The anti-metastatic activity of the compounds of Example 7 was tested using the procedure of Example 2. Specifically, PC3-M or PC3 cells were treated with 10 µM of compound (for invasion, FIG. 9) or a range of concentrations (for growth inhibition, FIG. 10). For invasion, values are the mean±SD number of invading cells, as a percent of untreated controls, from N=3 separate assays run at different times (each assay was in replicates of N=4). Cell viability was determined by MTT assay as recited in Kyle et al., *Mol. Pharmacol,* 51(2): 193-200 (1997); herein incorporated in its entirety. Values are the mean±SD of N=2 separate assays run at different times (N=3 for each assay), and are the percent of untreated controls.

Compounds 1, 8 and 17 did not show any significant inhibition of cell invasion whereas the remaining compounds showed varying levels of anti-metastatic activity.

Example 9

Using procedures set forth in the Detailed Description and using the appropriate starting materials, the following compounds were made or purchased commercially (compounds 21-26). The synthesis of compound 22 is as described herein.

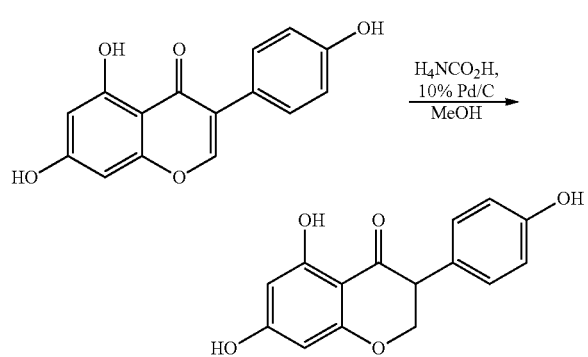

5,7,4'-trihydroxyisoflavanone (22).

Compound 22 was prepared following the general procedure described by Wähälä K. and Hase T. A., *Heterocycles* 28:183-86 (1989), herein incorporated by reference in its entirety. To a 50 mL round bottom flask was added genistein (270 mg, 1 mmol) and ammonium formate (1.08 g, 4 mmol). The flask was purged with $N_2$, followed by addition of methanol (20 mL) and 10% Pd/C (255 mg). Upon consumption of the starting material (measured by reverse phase HPLC), the reaction mixture was passed through a pad of silica gel with EtOAc/Hex as the eluent. The solvent was concentrated in vacuo to afford crude 22. Purified by recrystallization from $CHCl_3$/MeOH to afford 22 (144 mg, 53%) as brown crystals. Analytical data for isoflavanone 22: $^1$H NMR (500 MHz, DMSO) δ 12.19 (s, 1H), 10.84 (br s, 1H), 9.42 (br s, 1H), 7.08 (d, J=8.5 Hz, 2H), 6.73 (d, J=8.5 Hz, 2H), 5.91-5.90 (s, 2H), 4.53 (d, J=6.5 Hz, 2H), 4.00 (t, J=6.5 Hz, 1H); $^{13}$C NMR (125 MHz, DMSO) δ 197.6, 167.4, 164.6, 163.6, 157.4, 130.4, 126.3, 116.0, 102.5, 96.9, 95.5, 49.9; LCMS: Mass calculated for $C_{15}H_{12}O_5$, [M+H]$^+$, 273. Found 273.

Figure 11:
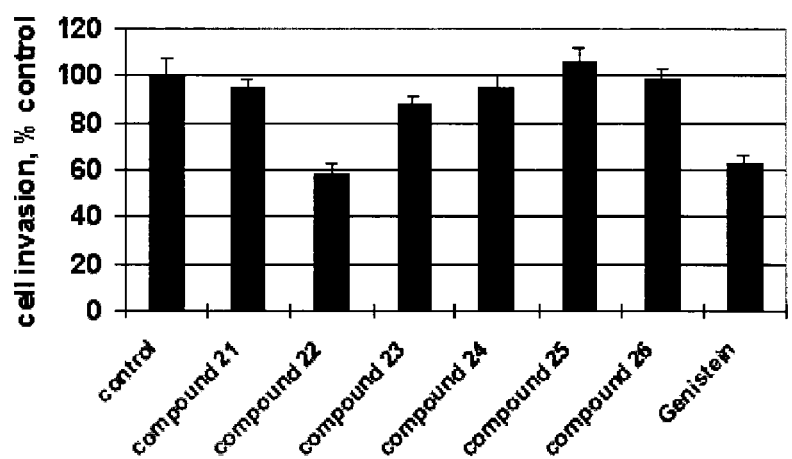
FIG. 11 shows the results of cell invasion assays conducted with Compounds 21-26 using PC3-M cells according to the method of Example 2.
Figure 12:
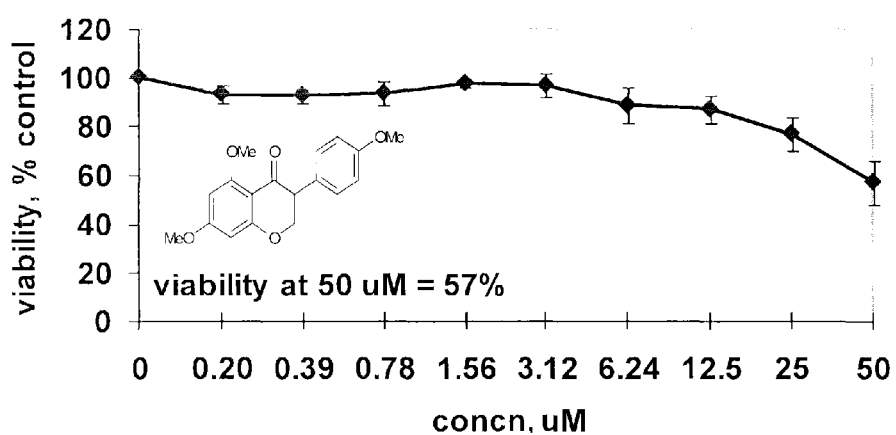
FIG. 12 shows the results of 3-day growth inhibition MTT assays conducted with Compounds 21-26. PC3-M human prostate cancer cells were treated with different concentrations of the indicated compound, and then MTT reduction was measured according to the method of Example 9.
Figure 12:
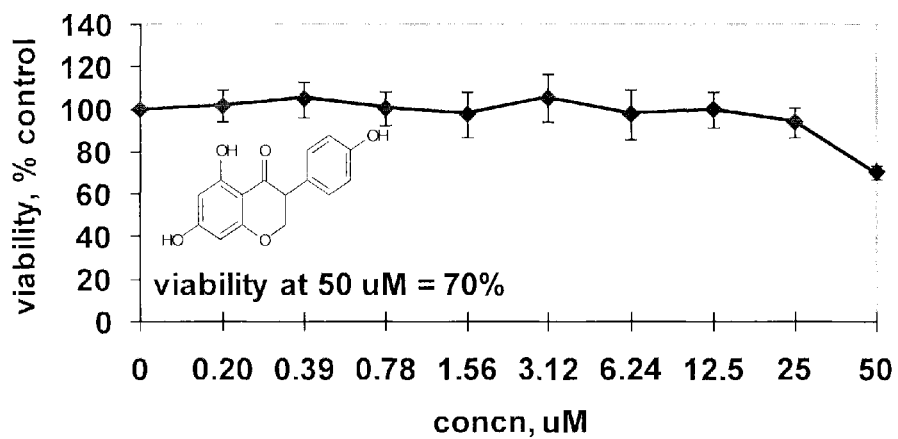
Figure 12:
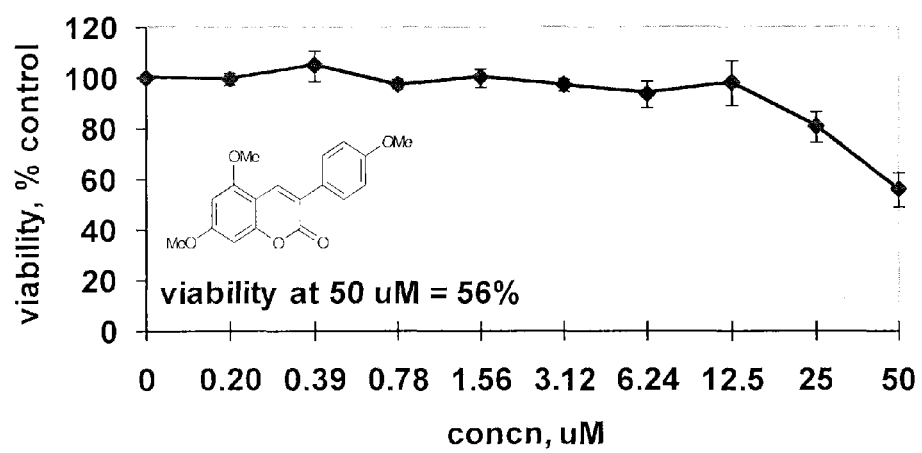
Figure 12:
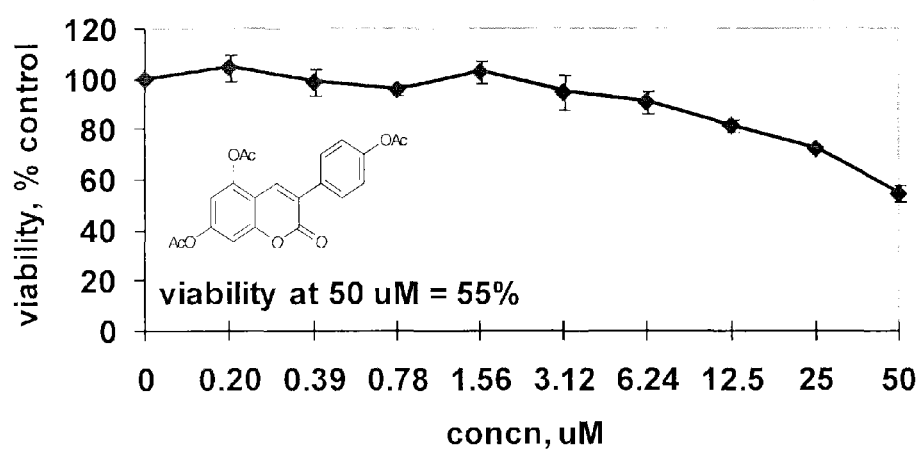
Figure 12:
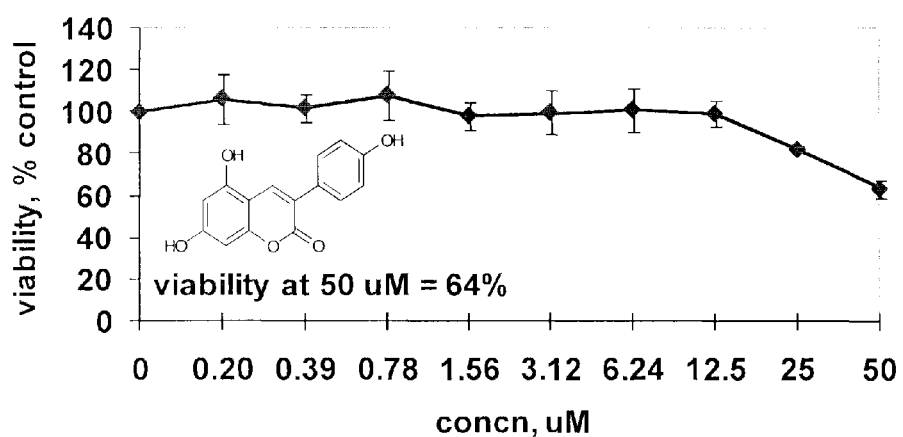
Figure 12:
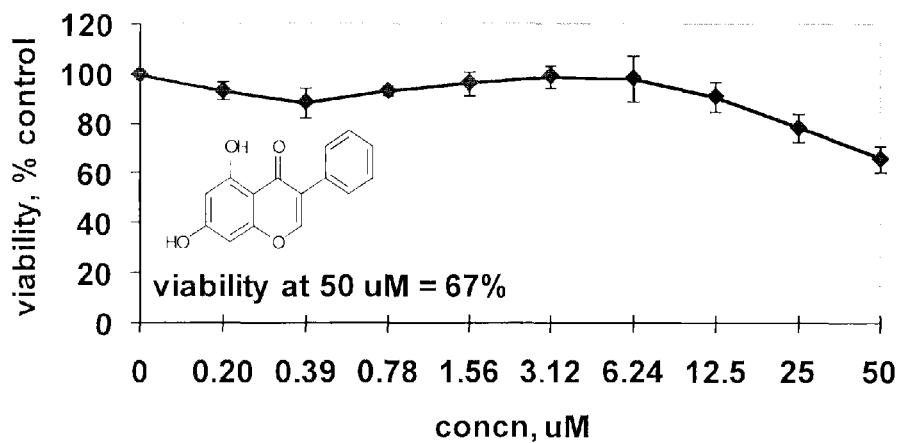

The anti-metastatic activity of compounds 21-26 was tested using the procedure of Example 2. Specifically, PC3-M cells were treated with 10 μM of compound (for invasion, FIG. 11) or a range of concentrations (for growth inhibition, FIG. 12). For invasion, values are the mean±SD number of invading cells, as a percent of untreated controls, from N=3 separate assays run at different times (each assay was in replicates of N=4). Cell viability was determined by MTT assay as recited in Kyle et al., *Mol. Pharmacol,* 51(2):193-200 (1997); herein incorporated by reference in its entirety. Values are the mean±SD of N=2 separate assays run at different times (N=3 for each assay), and are the percent of untreated controls.

A consideration of findings for compounds 21-26 leads to the following conclusions: 1) it is possible to retain anti-invasion efficacy while having little-to-no effect upon cell growth inhibition, for example compound 22; 2) reduction of the ring B double bond does not confer loss of activity; 2) moving the ring B carbonyl group to generate the coumarin core confers loss of activity, for example compounds 23, 24 and 25.

Example 10

Using procedures set forth in the Detailed Description and using the appropriate starting materials, the following compounds were made or purchased commercially (compounds 31-38). The synthesis of compounds 34, 37, and 38 is as described herein.

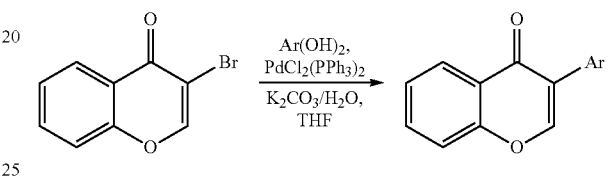

2'-chloroisoflavone (34).

Compound 34 was prepared according to a procedure modified from that described by Hoshino, Y., Miyaura, N. and Suzuki, A.; *Bull. Chem. Soc. Jpn.* 61:3008-3010 (1998), herein incorporated by reference in its entirety. To a 10 mL round bottom flask was added 3-bromochromone$^2$ (338 mg, 1.5 mmol), 2-chlorophenylboronic acid (258 mg, 1.65 mmol), $K_2CO_3$ (622 mg, 4.5 mmol), and $PdCl_2(PPh_3)_2$ (45 mg, 0.045 mmol). The flask was equipped with a reflux condenser and purged with $N_2$. To the flask was added THF (3 mL) and water (1.5 mL), and the reaction was heated to reflux. After 16 hours, the reaction was stopped and allowed to cool to room temperature. The reaction mixture was passed through a short pad of silica gel using EtOAc as the eluent and the resulting mixture concentrated in vacuo. Purified by flash column chromatography ($SiO_2$, 10% EtOAc/Hex) to afford 34 (246 mg, 64%) as an off-white solid. Analytical data for isoflavone 34: $^1$H NMR (500 MHz, $CDCl_3$) δ 8.33 (d, J=9 Hz, 1H), 7.99 (s, 1H), 7.74 (app t, J=10.5 Hz, 1H), 7.54-7.51 (m, 2H), 7.47 (app t, J=7 Hz, 1H), 7.39-7.35 (m, 3H); $^{13}$C NMR (125 MHz, $CDCl_3$) δ 175.9, 156.6, 154.7, 134.8, 134.0, 132.5, 131.1, 130.1, 127.0, 126.7, 125.6, 124.7, 124.4, 118.4, 100.0; LCMS: Mass calculated for $C_{15}H_9ClO_2$, [M+H]$^+$, 257. Found 257.

4'-fluoroisoflavone (37).

Prepared according to general procedure using 3-bromochromone (338 mg, 1.5 mmol), 4-fluorophenylboronic acid (231 mg, 1.65 mmol), $K_2CO_3$ (622 mg, 4.5 mmol), $PdCl_2(PPh_3)_2$ (45 mg, 0.045 mmol), THF (3 mL) and water (1.5 mL). Purified by flash column chromatography ($SiO_2$, 10% EtOAc/Hex) to afford afford 37 (81 mg, 23%) as a white solid. Analytical data for isoflavone 37: $^1$H NMR (500 MHz, $CDCl_3$) δ 8.34 (d, J=9 Hz, 1H), 8.04 (s, 1H), 7.72 (app t, J=9 Hz, 1H), 7.58-7.56 (m, 2H), 7.52 (d, J=8.5 Hz, 1H), 7.47 (app t, J=8 Hz, 1H), 7.16 (app t, J=9 Hz, 2H); $^{13}$C NMR (125 MHz, $CDCl_3$) δ 176.5, 164.0, 162.0, 156.5, 153.2, 134.0, 131.0, 128.0, 126.7, 125.6, 124.8, 118.3, 115.8; LCMS: Mass calculated for $C_{15}H_9FO_2$, [M+H]$^+$, 241. Found 241.

3'-chloroisoflavone (38).

Prepared according to general procedure using 3-bromochromone (338 mg, 1.5 mmol), 3-chlorophenylboronic acid (256 mg, 1.65 mmol), K$_2$CO$_3$ (622 mg, 4.5 mmol), PdCl$_2$(PPh$_3$)$_2$ (45 mg, 0.045 mmol), THF (3 mL) and water (1.5 mL). Purified by flash column chromatography (SiO$_2$, 10% EtOAc/Hex) to afford 38 (193 mg, 50%) as a white solid. Analytical data for isoflavone 38: $^1$H NMR (500 MHz, CDCl$_3$) δ 8.33 (d, J=9.5 Hz, 1H), 8.06 (s, 1H), 7.73 (app t, J=8.5 Hz, 1H), 7.60 (s, 1H), 7.59-7.45 (m, 3H), 7.39 (d, J=7 Hz, 2H); $^{13}$C NMR (125 MHz, CDCl$_3$) δ 176.1, 156.4, 153.6, 134.6, 134.1, 133.9, 130.0, 129.2, 128.6, 127.4, 126.7, 125.7, 124.7, 124.5, 118.4; LCMS: Mass calculated for C$_{15}$H$_9$ClO$_2$, [M+H]$^+$, 257. Found 257.

Figure 13:
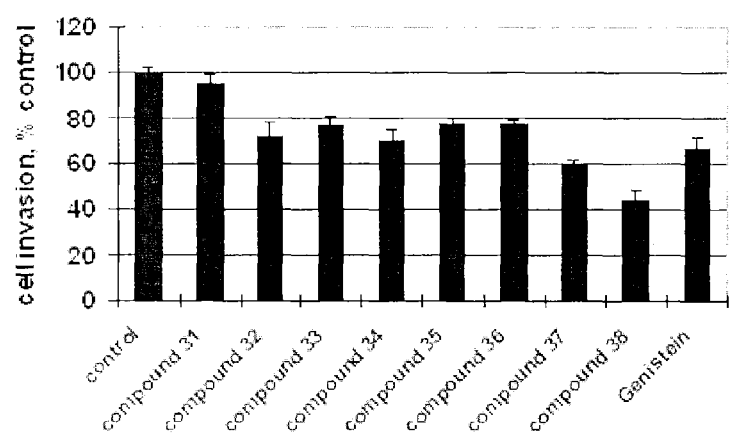
FIG. 13 shows the results of cell invasion assays conducted with Compounds 31-38 using PC3-M cells according to the method of Example 2.
Figure 14:
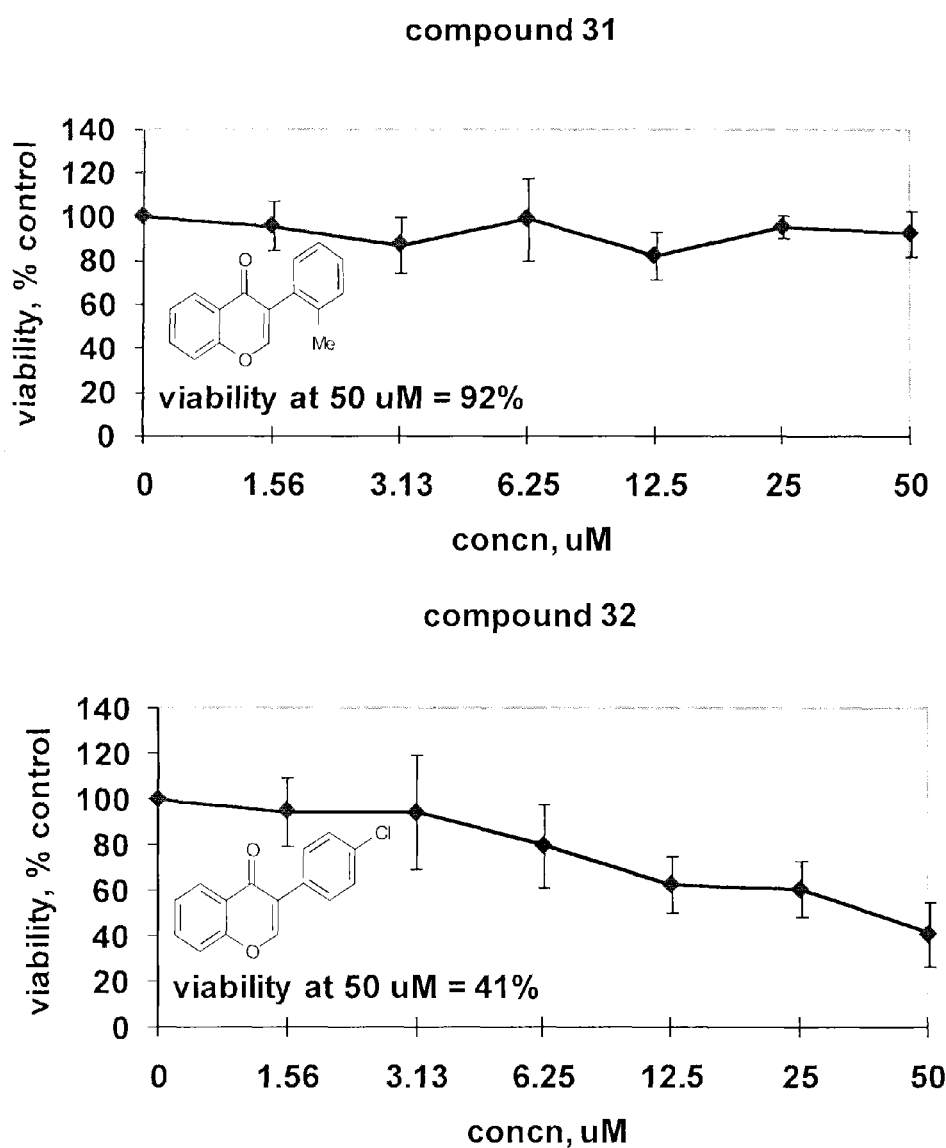
FIG. 14 shows the results of 3-day growth inhibition MTT assays conducted with Compounds 31-38. PC3-M human prostate cancer cells were treated with different concentrations of the indicated compound, and then MTT reduction was measured according to the method of Example 9.
Figure 14:
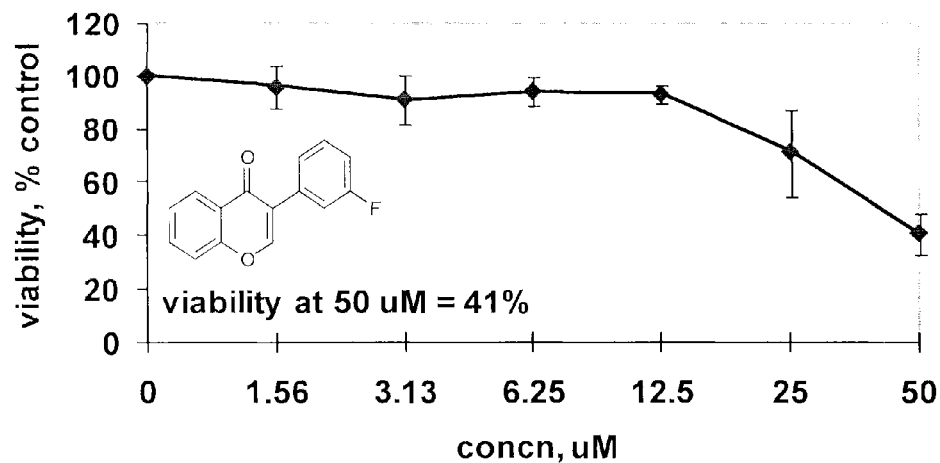
Figure 14:
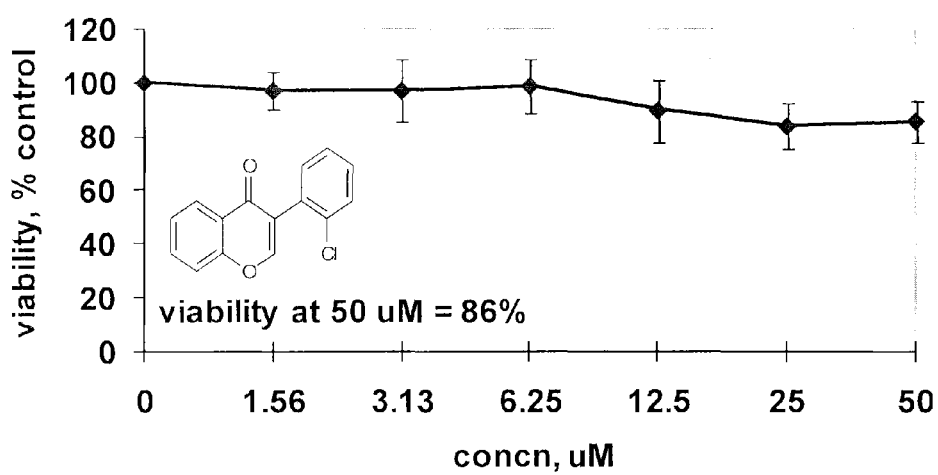
Figure 14:
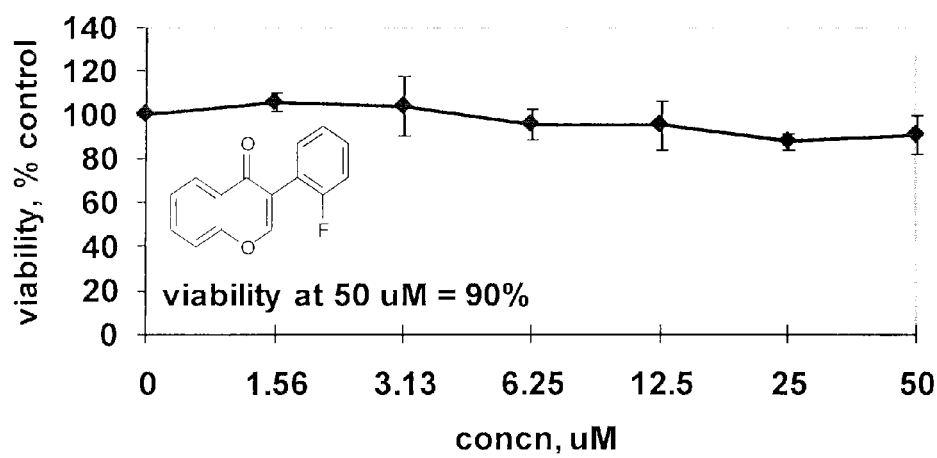
Figure 14:
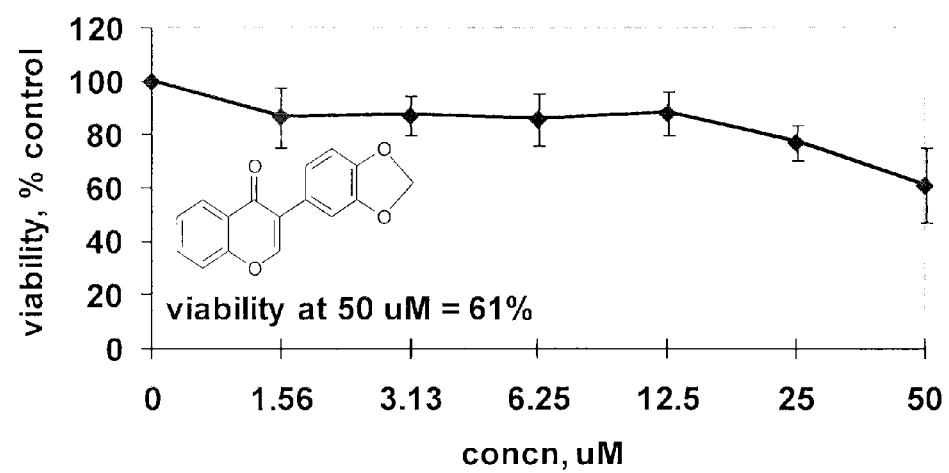
Figure 14:
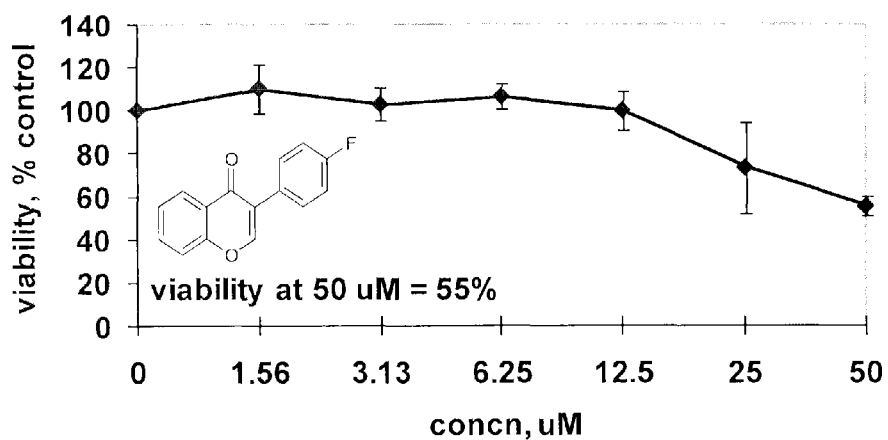
Figure 14:
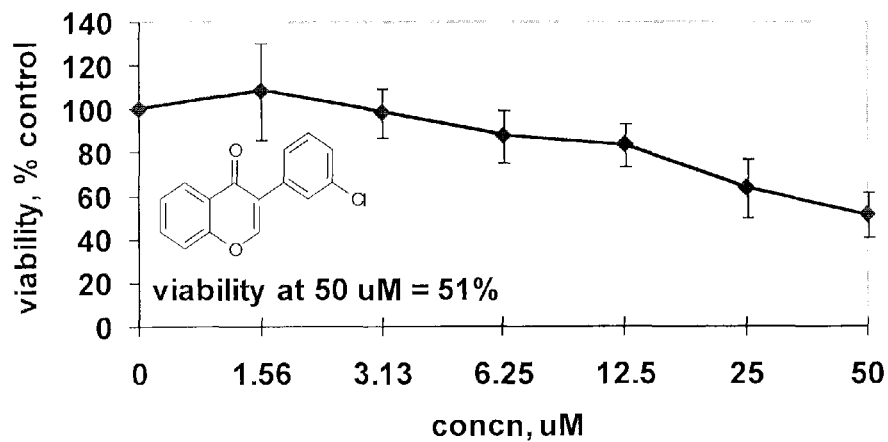

The anti-metastatic activity of compounds 31-38 was tested using the procedure of Example 2. Specifically, PC3-M cells were treated with 10 μM of compound (for invasion, FIG. 13) or a range of concentrations (for growth inhibition, FIG. 14). For invasion, values are the mean±SD number of invading cells, as a percent of untreated controls, from N=3 separate assays run at different times (each assay was in replicates of N=4). Cell viability was determined by MTT assay as recited in Kyle et al., *Mol. Pharmacol,* 51(2):193-200 (1997); herein incorporated by reference in its entirety. Values are the mean±SD of N=2 separate assays run at different times (N=3 for each assay), and are the percent of untreated controls.

A consideration of findings for compounds 31-38 leads to the conclusion that new chemical entities have been identified with anti-invasive and growth inhibitory effects, for example compound 38.

Example 11

Using procedures set forth in the Detailed Description and using the appropriate starting materials, the following compounds were made or purchased commercially (compounds 41-48). The synthesis of compounds 41 and 46 is as described herein.

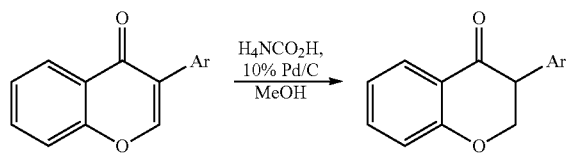

2'-chloroisoflavanone (41).

Compound 41 was prepared following the general procedure described by Wähälä and Hase, Heterocycles 1989, 28, (1), 183-186, herein incorporated by reference. To a 10 mL round bottom flask was added 2'-chloroisoflavone (152 mg, 0.592 mmol) and ammonium formate (149 mg, 2.37 mmol). The flask was purged with N$_2$, followed by addition of methanol (8 mL) and 10% Pd/C (151 mg). The reaction was allowed to stir at room temperature and monitored by reverse phase HPLC. Upon consumption of starting material, the reaction mixture was passed through a pad of silica gel using EtOAc as the eluent. The solvent was concentrated in vacuo to afford crude 41. Purified by flash column chromatography (SiO$_2$, 10% EtOAc/Hex) to afford 41 (21 mg, 14%) as an off-white solid. Analytical data for isoflavanone 41: $^1$H NMR (500 MHz, CDCl$_3$) δ 7.98 (d, J=9.5 Hz, 1H), 7.53 (app t, J=9 Hz, 1H), 7.39-7.28 (m, 4H), 7.09-7.03 (m, 2H), 4.71-4.66 (m, 2H), 4.04-4.01 (app t, J=6.5 Hz, 1H); $^{13}$C NMR (125 MHz, CDCl$_3$) δ 192.4, 161.8, 136.3, 133.2, 129.1, 128.9, 128.1, 128.0, 121.9, 121.3, 118.1, 71.7, 52.6; GCMS: Mass calculated for C$_{15}$H$_{11}$ClO$_2$, [M]$^+$, 259. Found 225.

4'-fluoroisoflavanone (46).

Prepared according to the general procedure using 4'-fluoroisoflavone (77 mg, 0.319 mmol), ammonium formate (81 mg, 1.28 mmol), methanol (6.4 mL) and 10% Pd/C (81 mg). Purified by flash column chromatography (SiO$_2$, 10% EtOAc/Hex) to afford 46 (18 mg, 23%) as an off-white solid. Analytical data for isoflavanone 46: $^1$H NMR (500 MHz, CDCl$_3$) δ 7.97 (d, J=9.5 Hz, 1H), 7.53 (app t, J=9 Hz, 1H), 7.29-7.26 (m, 2H), 7.09-7.03 (m, 3H), 4.70-4.62 (m, 2H), 4.02-3.99 (m, 1H); $^{13}$C NMR (125 MHz, CDCl$_3$) δ 205.8, 192.2, 191.9, 161.8, 136.4, 130.9, 130.5, 128.0, 122.0, 121.1, 118.1, 116.2, 116.0, 71.6, 51.8; LCMS: Mass calculated for C$_{15}$H$_{11}$FO$_2$, [M+H]$^+$, 243. Found 243.

Figure 15:
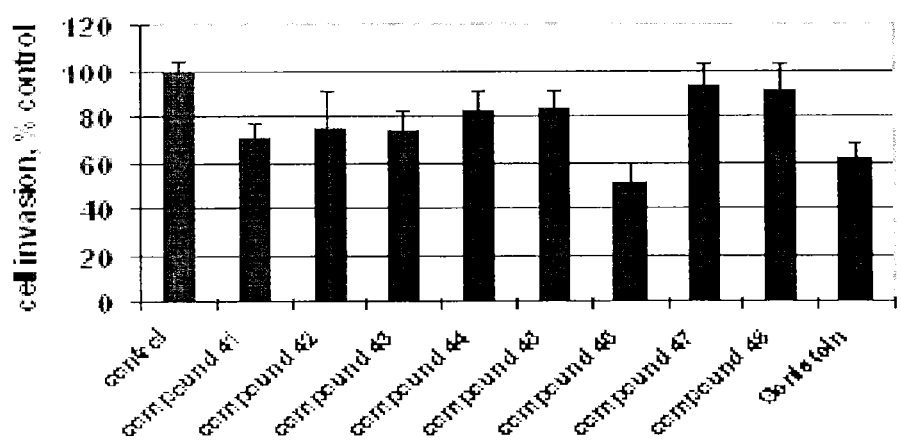
FIG. 15 shows the results of cell invasion assays conducted with Compounds 41-48 using PC3-M cells according to the method of Example 2.
Figure 16:
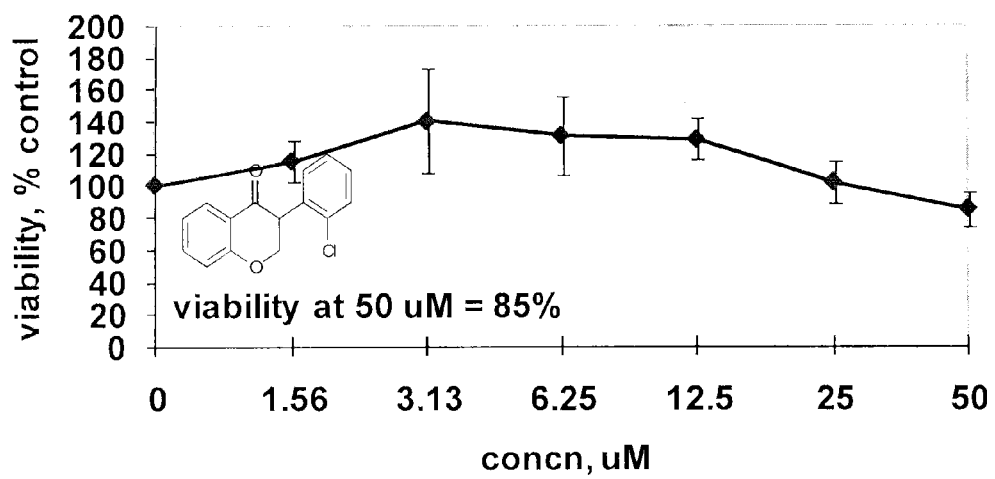
FIG. 16 shows the results of 3-day growth inhibition MTT assays conducted with Compounds 41-48. PC3-M human prostate cancer cells were treated with different concentrations of the indicated compound, and then MTT reduction was measured according to the method of Example 9.
Figure 16:
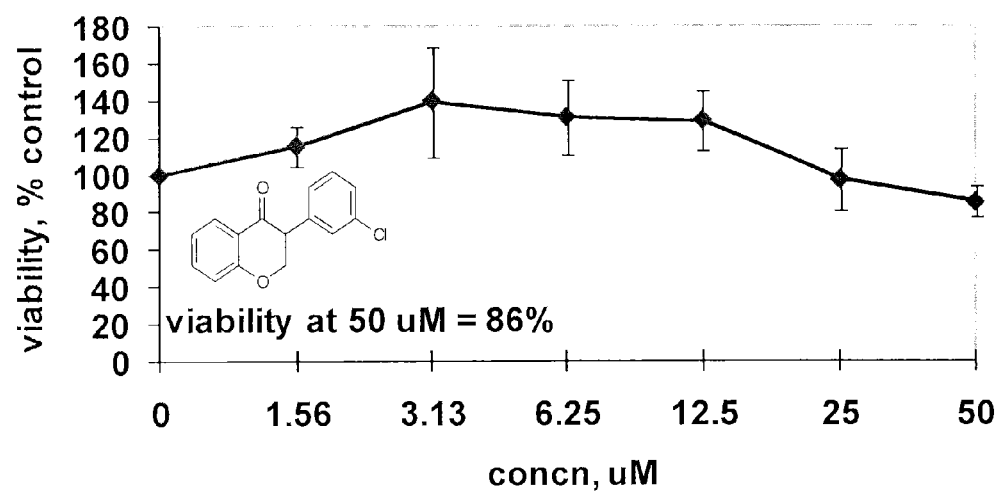
Figure 16:
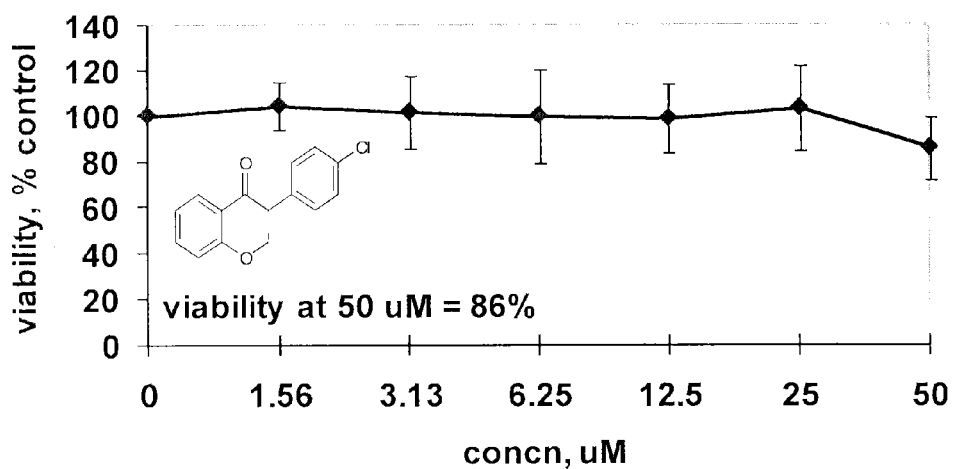
Figure 16:
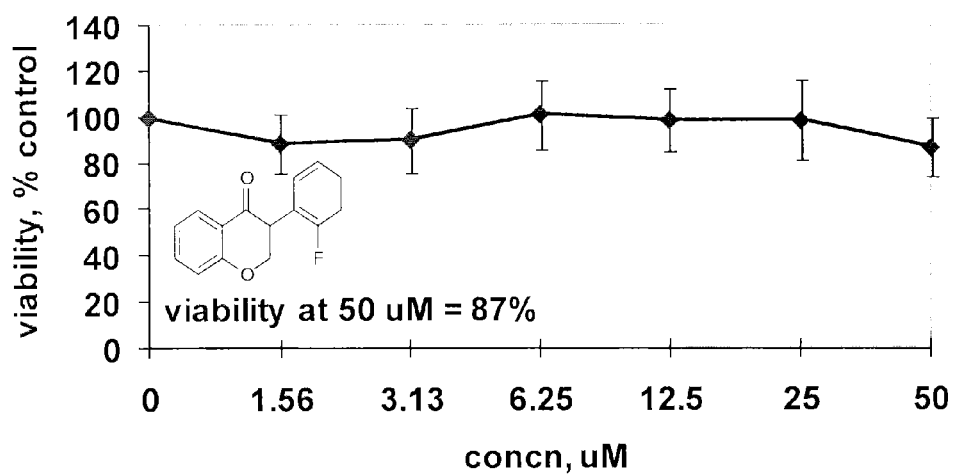
Figure 16:
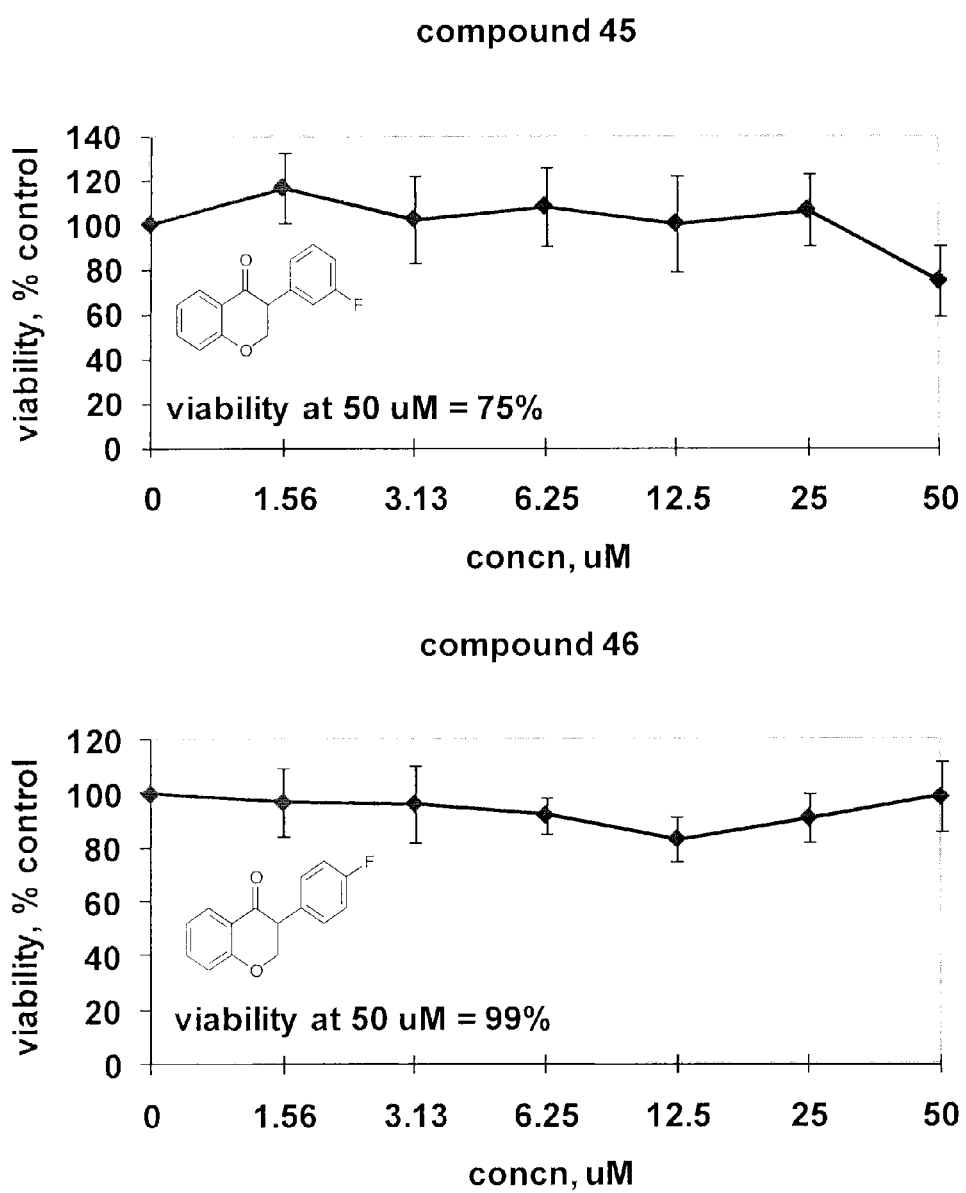
Figure 16:
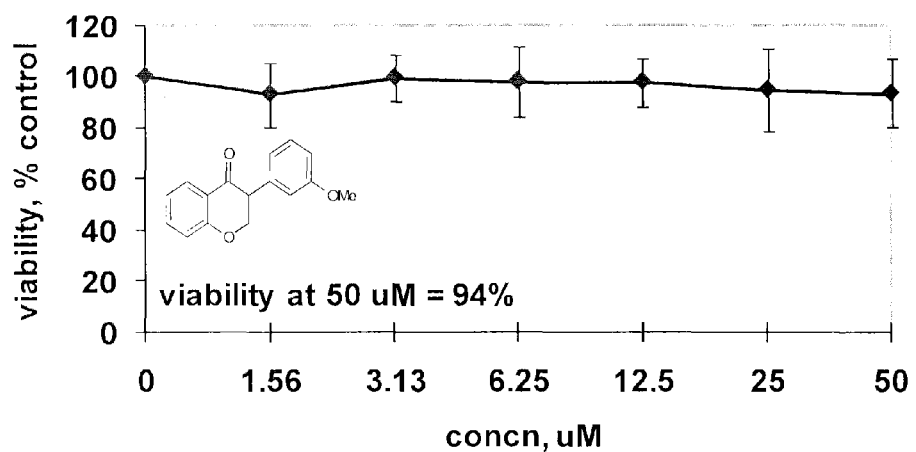
Figure 16:
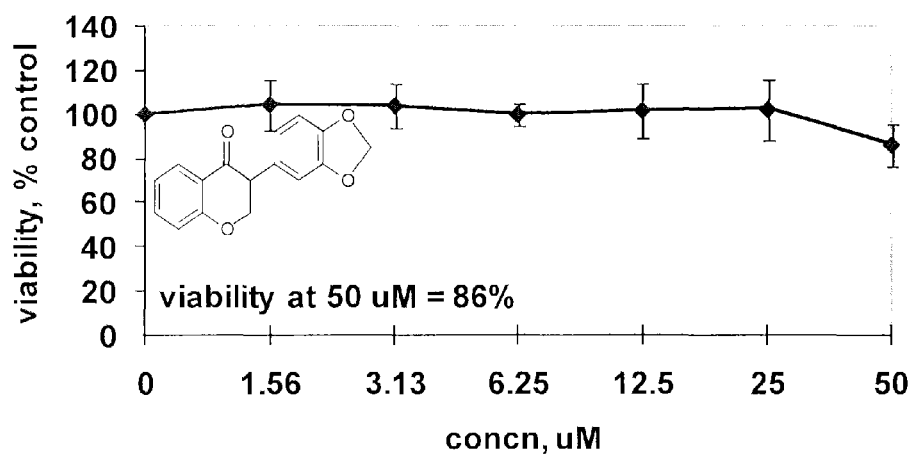

The anti-metastatic activity of compounds 41-48 was tested using the procedure of Example 2. Specifically, PC3-M cells were treated with 10 μM of compound (for invasion, FIG. 15) or a range of concentrations (for growth inhibition, FIG. 16). For invasion, values are the mean±SD number of invading cells, as a percent of untreated controls, from N=3 separate assays run at different times (each assay was in replicates of N=4). Cell viability was determined by MTT assay as recited in Kyle et al., *Mol. Pharmacol,* 51(2):193-200 (1997); herein incorporated by reference in its entirety. Values are the mean±SD of N=2 separate assays run at different times (N=3 for each assay), and are the percent of untreated controls.

A consideration of findings for compounds 41-48 leads to the conclusion that new chemical entities have been identified with anti-invasive efficacy at least equal to that of genistein, and that have no growth inhibitory effects.

Example 12

Figure 17:
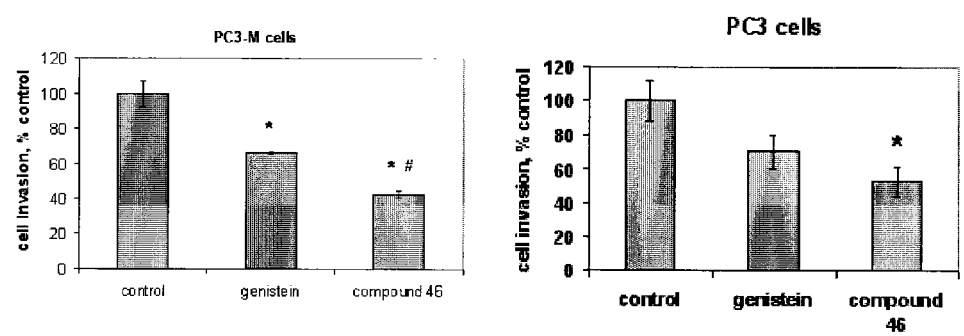
FIG. 17 shows the results of cell invasion assays conducted with control, genistein-treated, and compound 46-treated PC3-M and PC3 cells according to the method of Example 2 with an increase in invasion assay time to 16 hours.
Figure 28:
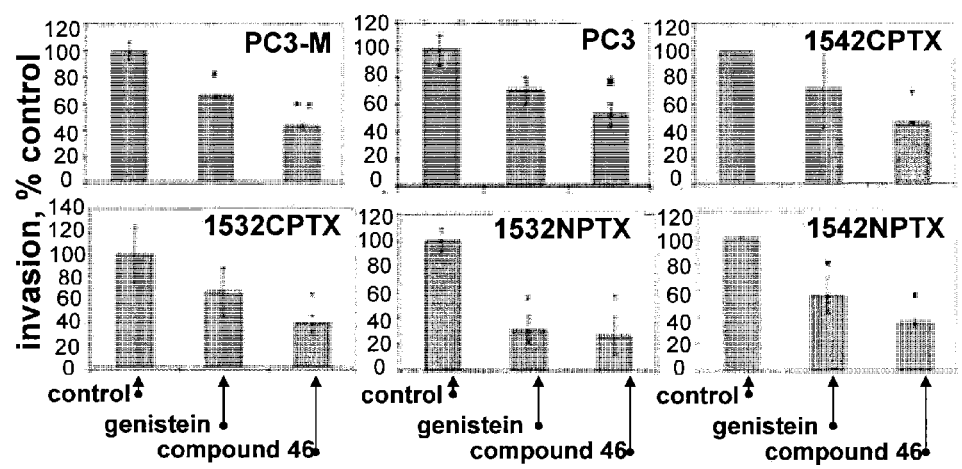
FIG. 28 shows the results of cell invasion assays conducted with control, genistein-treated, and compound 46-treated PC3-M, PC3, 1542CPTX, 1532CPTX, 1532NPTX, and 1542NPTX cells according to the method of Example 2 with an increase in invasion assay time to 16 hours.

Expanded studies were performed on compound 46. Cell invasion assays conducted using the procedure of Example 2 utilized control, genistein-treated, and compound 46-treated PC3-M, PC3, 1542CPTX, 1532CPTX, 1532NPTX, and 1542NPTX cells (FIG. 17, FIG. 28). This allowed assay conditions to be adjusted so as to optimize assessment of differences between these three treatment conditions. In particular, the invasion assay time was extended from 14 to 16 hours. Depicted data are the mean±SEM of a single experiment run in replicates of 4; * and # denote differences from control and genistein cells, respectively, as defined by a Student-s 2-sided t test with p value of ≤0.05. The result indicates that compound 46 has greater efficacy than genistein.

Figure 18:
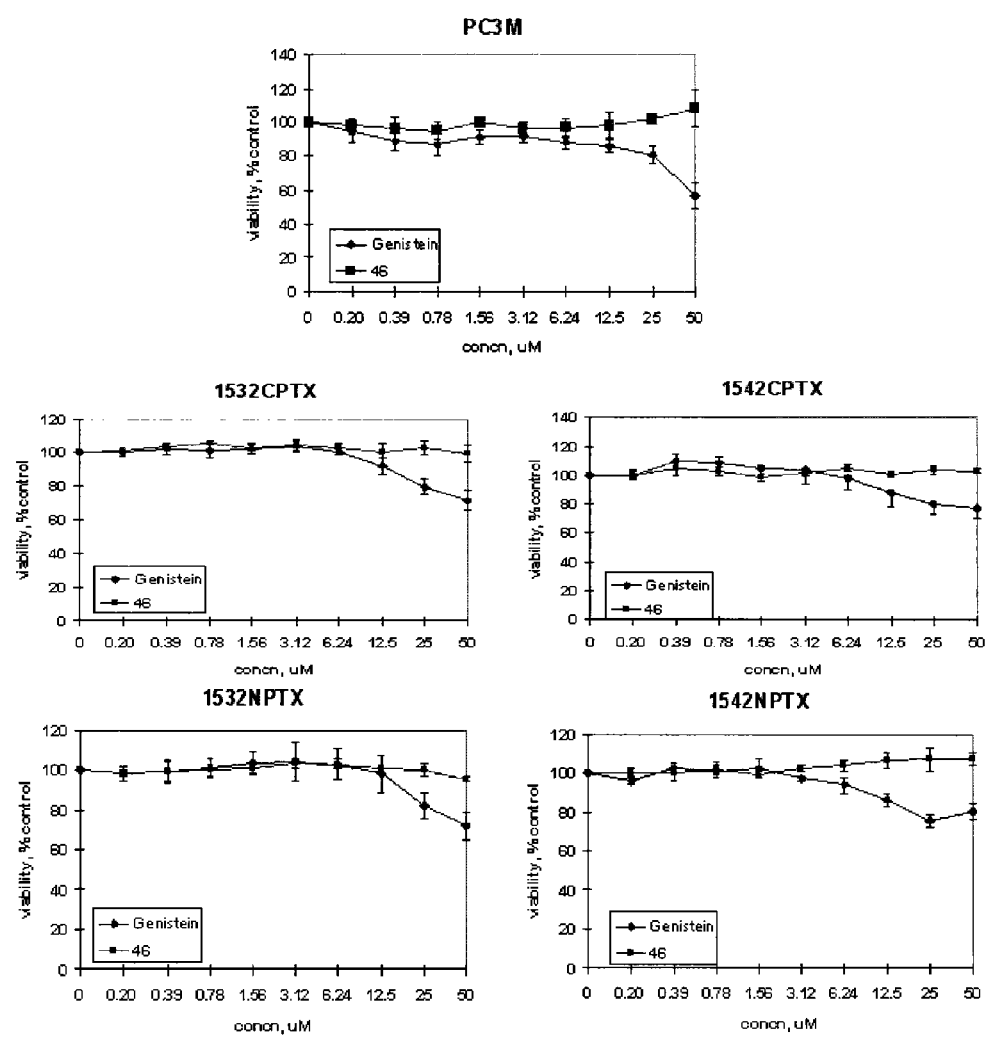
FIG. 18 shows the results of growth inhibition assays performed with different cell lines (PC3-M, 1532CPTX, 1542CPTX, 1532NPTX, and 1542NPTX) treated with a range of concentrations of compound 46.
Figure 29:
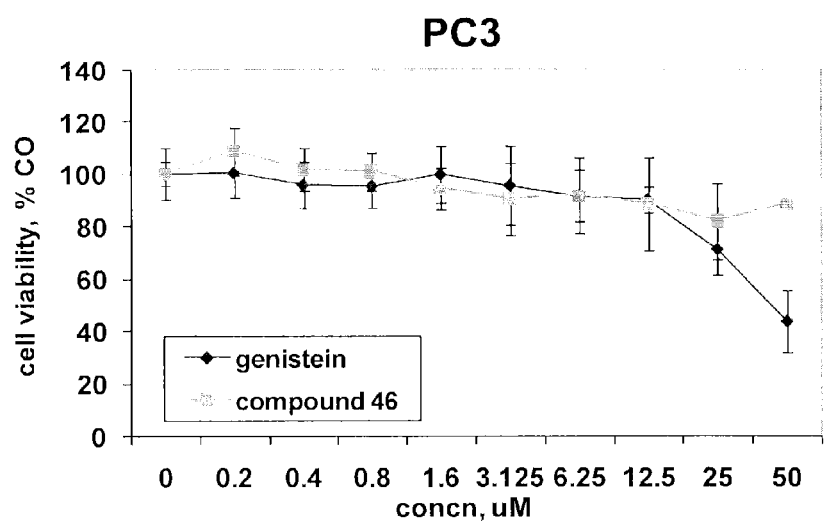
FIG. 29 shows the results of growth inhibition assays performed with PC3 cells treated with a range of concentrations of compound 46.

Growth inhibition assays were performed with different cell lines using the procedure of Example 2. Specifically, cell lines (PC3, PC3-M, 1532CPTX, 1542CPTX, 1532NPTX, and 1542NPTX) were treated with a range of concentrations of compound 46 (FIG. 18, FIG. 29). Cell viability was determined by MTT assay as recited in Kyle et al., *Mol. Pharmacol,* 51(2):193-200 (1997); herein incorporated by reference in its entirety. Data are the mean±SEM of a single experiment, performed in triplicate. As shown, under these conditions compound 46 is less toxic than genistein, and in fact shows no toxicity.

Example 13

Figure 19:
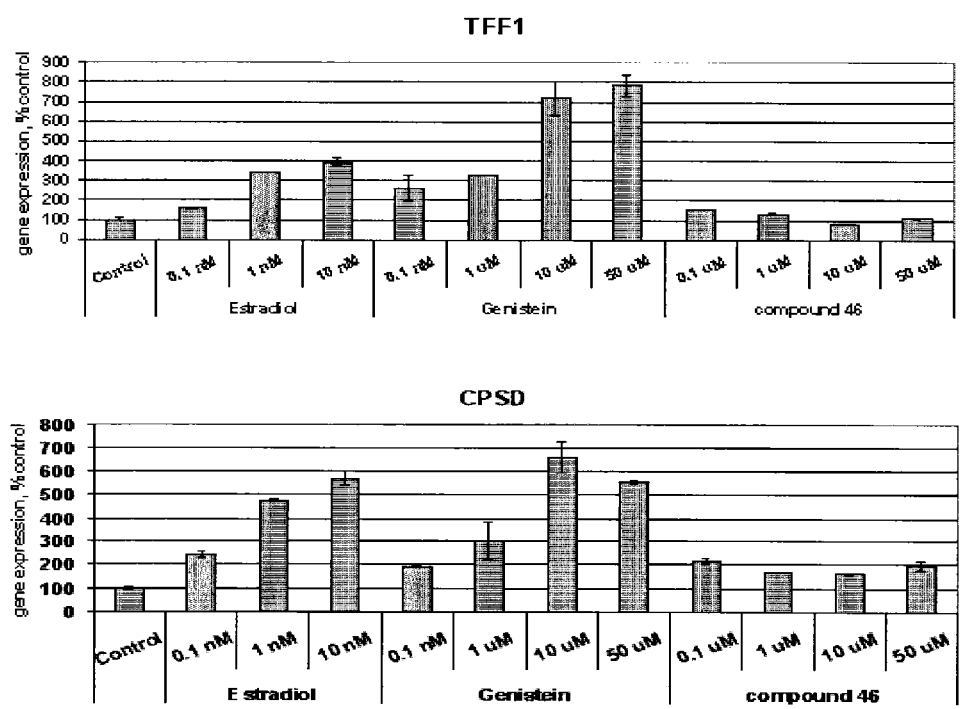
FIG. 19 shows the results of studies to assess the estrogenic activity of compound 46 compared to genistein. Estrogen receptor (ER) positive human MCF-7 breast cancer cells were treated with the compounds and the expression of estrogen responsive genes TFF1 and CPSD was measured.
Figure 30:
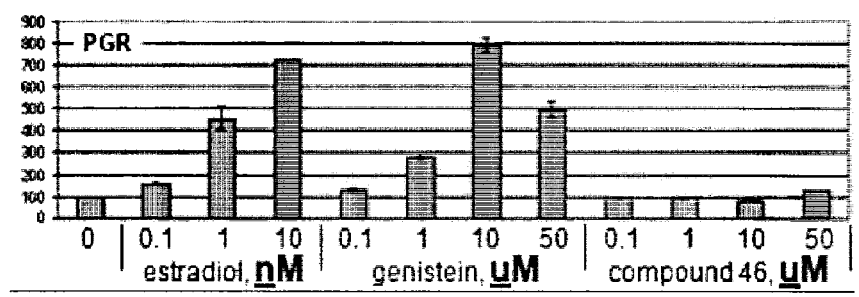
FIG. 30 shows the results of studies to assess the estrogenic activity of compound 46 compared to genistein. Estrogen receptor (ER) positive human MCF-7 breast cancer cells were treated with the compounds and the expression of the estrogen responsive gene PGR was measured.
Figure 31:
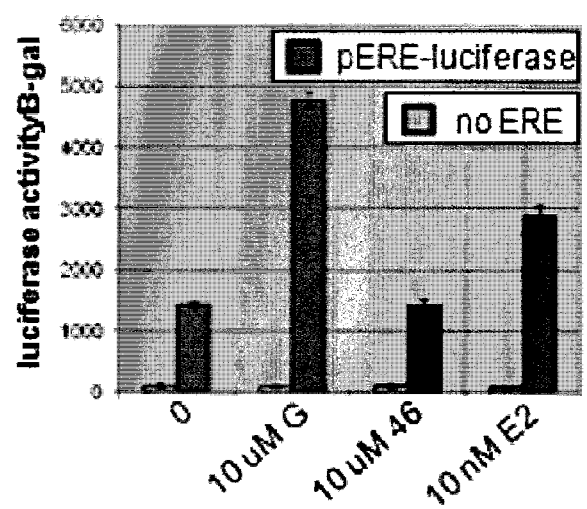
FIG. 31 shows the effect of treating MCF-7 ER-positive breast cancer cells bearing an ER promoter-luciferase reporter vector construct with 10 μM genestein, 10 μM compound 46, or nM estradiol (E2), as measured in units of luciferase activity.

Studies were performed to assess the estrogenic activity of compound 46 (also known as KBU2036) compared to genistein. Estrogen receptor (ER) positive human MCF-7 breast cancer cells were cultured under hormone-free conditions (using phenol red free culture media, and charcoal stripped fetal bovine serum), treated for 24 hours with 0.1-10 nM estradiol, 0.1-50 µM genistein, or 0.1-50 µM compound 46, as indicated, and the expression of estrogen responsive genes was measured (FIG. 19, FIG. 30). The genes were: TFF1 (trefoil factor 1; also known as pS2), PGR (progesterone receptor), and CPSD (cathepsin D). Gene expression was measured by isolating RNA, and performing real time quantitative reverse transcription/polymerase chain reaction (qRT/PCR), using exon spanning primers (purchased from Applied Biosystems). The expression of GAPDH was also measured, and used to normalize the expression of ER responsive genes. Data below are the mean±SD of a single experiment, performed in duplicate. These findings demonstrate that under the recited assay conditions, compound 46 has no estrogenic activity, in contrast to that of genistein and estradiol. Additionally, the ability of compound 46 to activate an ER promoter-luciferase reporter vector construct after transient transfection of the human ER positive breast cancer cell line, MCF-7, was evaluated (FIG. 31). FIG. 31 shows that 10 µM genistein and 10 nM estridiol (E2) each induced luciferase activity, while 10 µM compound 46 had no effect. "No associated control cells" were transfected with an identical vector construct that lacked the estrogen response element, i.e., noERE.

Thus, compound 46 constitutes a new chemical entity that has greater anti-invasion efficacy compared to genistein, but that has no cell toxicity and no estrogenic activity, under the recited experimental conditions.

Example 14

Endoglin Suppresses Human Prostate Cancer Metastasis

Materials and Methods
Cell Culture

The engineering and phenotypic characterization of endoglin variant cell lines, from parental PC3-M cells, has been described (Stetler-Stevenson et al. (2001) Semin. Cancer Biol. 11:143-152; herein incorporated by reference in its entirety). In some experiments, PC3-M cells stably transfected with green fluorescent protein (GFP) were used. The engineering and characterization of PC3-M-GFP cells has been described (Lakshman et al. (2008) Cancer Res. 68:2024-2032; herein incorporated by reference in its entirety). Cells were cultured in RPMI 1640 medium (Gibco, Grand Island, N.Y.) supplemented with 10% heat-inactivated fetal bovine serum (product SH30071-03, Fisher/Hyclone; Waltham, Mass.), 2 mM glutamine, and 10 mM Hepes (pH 7.2). All cells were maintained at 37° C. in a humidified atmosphere of 5% carbon dioxide and 95% air under subconfluent exponential growth conditions with biweekly changes of medium, and were routinely monitored for mycoplasma infection. When implanted into the prostates of mice, cells were suspended in 35 µl of RPMI 1640 (Gibco), as described (Lakshman et al. (2008) Cancer Res. 68:2024-2032; herein incorporated by reference in its entirety).

Cell Invasion Assays

Boyden chamber cell invasion assays were performed as described (Xu et al. (2006) Oncogene 25:2987-2998; herein incorporated by reference in its entirety). Briefly, $10^4$ cells in 52 µl of serum free culture media containing 0.1% bovine serum albumin were placed in the upper chamber of a 48-well Boyden chamber apparatus (catalog #AP48, Neuro Probe; Gaithersburg, Md.) and allowed to invade for 13 hr through a Nuclepore Track-Etch Membrane with 8 µm pores (catalog #: NC 983-1643; Whatman, Clifton, N.J.) pre-coated with denatured collagen (catalog #: 214340; Difco-Becton Dickinson, Sparks, Md.) towards serum-free NIH-3T3 conditioned medium in the lower chamber. The percentage of invading cells was counted under light microscopy. A total of two experiments were performed, with four replicate samples for each experimental condition. All assays were performed in replicates of 4, and repeated at a separate time, also in replicates of 4.

Animal Housing and Orthotopic Implantation

Inbred four week old male athymic BALB/C mice (Charles River Laboratories) were treated under a Northwestern University ACUC approved protocol. Mice were housed in a barrier facility with 12 hr light/dark cycles, and given food (Harlan Teklad 2016S® chow) and water ad libitum.

Orthotopic implantation of cells into the dorsal lobe of the prostate was performed as previously described (Lakshman et al. (2008) Cancer Res. 68:2024-2032; herein incorporated by reference in its entirety). Briefly, the dorsal lobes were exposed by delivering the prostate through a lower abdomen midline incision. Cells were injected under the capsule of the right lobe through a 30 gauge needle, thus forming a bleb that remained intact after needle withdrawal. The peritoneum was closed with 4-0 polyvinyl, and the skin was stapled. Mice not recovering from surgery, or dying (or moribund and thus euthanized) within the 48 hour postoperative period, were considered perioperative mortalities.

Examination of Organs and Quantification of Lung Metastasis

Necropsy was performed at four or five weeks after implantation, as indicated, and metastasis quantified, as previously described (Lakshman et al. (2008) Cancer Res. 68:2024-2032; herein incorporated by reference in its entirety). The prostate tumor volume was calculated as 0.52× (width)$^2$×(length) from measures taken in perpendicular dimensions. Lungs and prostate tumor were fixed in 10% formalin. A portion of prostate tumor samples were snap frozen. All major organs were examined for microscopic evidence of metastasis on 5 µm hematoxylin and eosin (H&E) stained sections. Lungs were step sectioned at 30 µm increments in the saggital plane to expose all lobes in one plane, and metastasis were identified by histomorphometry on H&E stained tissue, in a total of 15 sections per lung. Prostate tumor tissue was step sectioned at 1 mm increments. All necropsies and tissue analysis were performed by a single researcher.

Measurement of Viable Prostate Cancer Cells in the Blood

In all studies, a terminal blood draw was performed via cardiac puncture, and the resultant number of viable PCa cells was measured as previously described (Wyckoff et al. (2000) Cancer Res. 60:2504-2511; Xue et al. (2006) Cancer Res. 66:192-197; each herein incorporated by reference in its entirety). Briefly, blood was collected into a preservative free lithium heparin coated tube. After centrifugation, the resultant buffy coat and serum layers were plated into α-MEM (Gibco) with 5% fetal bovine serum. The following day, plates were rinsed twice with phosphate buffered saline (PBS), and cultured in RPMI 1640 (Gibco), 10% FBS, in the presence of G418. Ten days after plating, groups of ≥50 cells were scored as colonies, and counted. For animals from which 100 µl or more blood was harvested, the tumor blood burden per ml blood was taken as the number of colonies divided by the volume of blood taken.

Immunohistochemistry

Immunohistochemical staining was performed as previously described, with modifications (Lakshman et al. (2005) J. Cell Physiol. 203:583-588; Kelley et al. (2005) Cancer Epidemiol. Biomarkers Prev. 14:892-899; each herein incorporated by reference in its entirety). Primary tumor tissues were rehydrated, treated with hydrogen peroxide to quench endogenous peroxidase activity, and blocked with goat serum. Tissues were then stained with either anti-Ki67 (rabbit polyclonal; DAKO, Carpinteria, Calif.), diluted 1:200 in 5% goat serum, or with anti-GFP antibody (clone A11122, Molecular Probes), diluted 1:50. Signal was detected by using the EnVision™+System (DAKO), which employed a streptavidin-biotin polymer conjugated secondary antibody, along with 3,3'-diaminobenzidine tetrahydrochloride (Vector Laboratories, Burlingame, Calif.), both per manufacturer's instructions. Tissue was counterstained with hematoxylin (Zymed). Adjacent sections of primary tumor were stained for TUNEL using the Apoptag detection kit (Chemicon, Temecula, Calif.), per manufacturer's instructions.

Adjacent sections of immunostained tissue were read by a single pathologist in a blinded and batch fashion. Immunohistochemical scoring employed a semi-automated digital scanning system, designed to minimize reader bias. Slides were scanned at 20× on a ScanScope CS® (Aperio Technologies, CA). On resultant digitized H&E slides, 10 regions of interest (ROIs) were prospectively identified. Areas of infarction and necrosis were avoided. ROIs were imported onto adjacent slide sections, stained for Ki67 or TUNEL, as digital overlays. Ki67 was scored using the inbuilt 'positive pixel count algorithm', which computes the number of weak, moderate and strong staining pixels within the ROI, as well as the mean intensity within each of these categories. Settings were adjusted to exclude non-specific background staining TUNEL was scored using the 'CoLocalization' algorithm, which identifies co-localized brown and blue pixels—and thus 'nuclear' staining—and computes their staining index as above. For Ki67 and TUNEL, H-scores were calculated by determining the product of percent staining and average intensity, thus providing a measure of overall staining within the ROI.

In some experiments, PC3-M cells in culture were stained for cell surface endoglin, as described (Lin et al. (2002) Oncogene 21:8272-8281; herein incorporated by reference in its entirety), with modifications. Briefly, cells growing on glass cover slips for 24 hours were fixed in 3.7% paraformaldehyde at 37° C., treated with hydrogen peroxide, blocked in 1% fraction V bovine serum albumin (Sigma-Aldrich Corp, St. Louis, Mo.), incubated with anti-endoglin (clone 35; BD Biosciences) diluted 1:50, and signal detected with the EnVision™+System (DAKO), per manufacturer's instructions. All tissue was stained in a batch fashion, and all staining runs included antibody isotype negative controls.

Western Blots

Protein isolation from frozen tissue was performed as described, with modifications (Lakshman et al. (2005) J. Cell Physiol. 203:583-588; Lakshman et al. (2004) Exp. Mol. Pathol. 76:196-206; each herein incorporated by reference in its entirety). Briefly, snap frozen tumor tissue was extracted with RIPA buffer containing protease (aprotinin, leupeptin, pepstatin, and 1 mM EDTA) and phosphatase inhibitors (NaVO$_4$, NaF, and Phosphatase Inhibitor Cocktails #1 and #2; Sigma-Aldrich). Immunoblotting was performed as described (Craft et al. (2007) Oncogene 26:7240-7250; Lakshman et al. (2005) J. Cell Physiol. 203:583-588; Lakshman et al. (2004) Exp. Mol. Pathol. 76:196-206; Rohlff et al. (1998) Prostate 37:51-59; each herein incorporated by reference in its entirety), and used the following antibodies: anti-p21$^{waf1/cip1}$ (clone 19; Santa Cruz Biotechnology Inc.); anti-cleaved caspase 3 and anti-Smad3 (Cell Signaling Technology); and anti-Smad1 (Upstate Biotechnology, Lake Placid, N.Y., USA). In all instances, equal amounts of protein were loaded onto gels, and this was evaluated by probing blots for glyceraldehyde-3-phosphate dehydrogenase (GAPDH; Chemicon, Temecula, Calif.). All Western blots were repeated once, at a separate time.

RNA Isolation and Quantitative Reverse Transcription/Polymerase Chain Reaction (qRT/PCR)

RNA was isolated from snap frozen prostate tumor tissue using RNeasy RNA isolation kit from Qiagen (Valencia, Calif.), per manufacturer's instructions. RNA was treated with RNase free DNase, its quality and quantity assessed by optical density, and qRT/PCR performed on a dedicated ABI 7500 qPCR workstation, all as described (Ding et al. (2006) Prostate Cancer Prostatic Dis. 9:379-391; Ding et al. (2007) 18:321-330; each herein incorporated by reference in its entirety). Validated gene specific primer/probe sets for ID1, ID2, STAT1, JUNB, SOX4, MMP-2, MMP-9 and GAPDH were from Applied Biosystems. All primers were exon spanning, except for SOX4, which only contains 1 exon. RT minus control reactions were run as a negative control. Negative control reactions, in particular those for SOX4, were always negative under all reaction conditions. Assays were run in replicates of 2, and repeated a separate time, in replicates of 2.

Thymidine Uptake

Thymidine uptake was measured as previously described (Liu et al. (2001) Prostate Cancer Prostatic Dis. 4:81-92; herein incorporated by reference in its entirety). Briefly, 2,000 cells per 100 µl of cell culture media were plated into each well of a 96 well plate. Twenty-four hours later, cells were washed with and cultured in serum free media, and then treated with the indicated concentration of recombinant TGFβ1 (R&D Systems, Minneapolis, Minn.) for 24 hours. Thymidine uptake was measured by adding 0.5 mCi of [$^3$H] thymidine in 20 µl of cell culture media to each well, incubating for 6 hours at 37° C., harvesting cells onto glass fiber filters (Packard, Meriden, Conn.) with a Packard cell harvester and counted in a Matrix 9600 microplate counter (Packard). Assays were run in replicates of 3, and repeated at a separate time, in replicates of 3.

Statistical Analysis

Two or more treatment groups were compared by means of Chi-squared or Fisher's Exact test as appropriate for categorical outcomes, and by Student's t test or one way ANOVA as appropriate for continuous variables, as denoted. Statistical significance was considered present for p-values of ≤0.05. To evaluate the association between tumor weight and metastatic burden, the Spearman correlation coefficient was used. Statistical tests were performed with the statistical software package "R" version 2.8 and SAS, V9.1 (Cary, N.C.).

Characterization of Endoglin Variant Cell Lines

Figure 20:
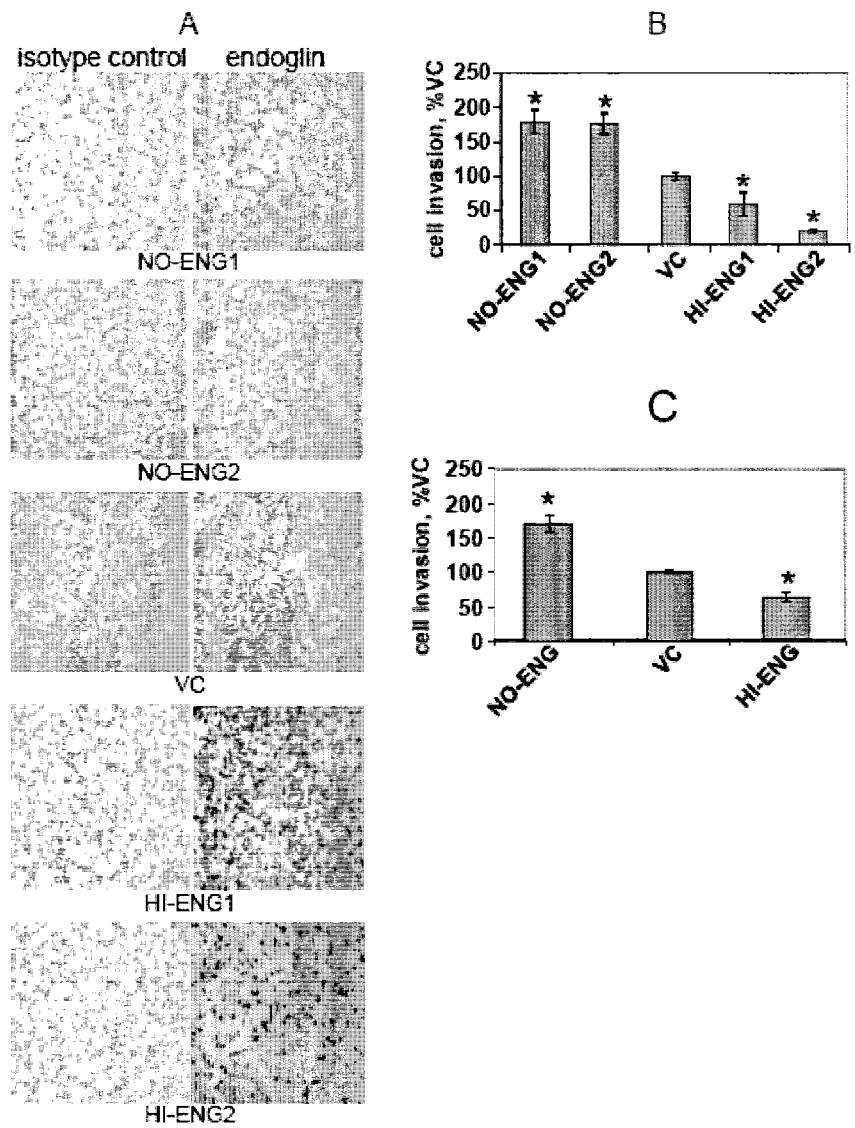
FIG. 20 shows suppression of human prostate cancer cell invasion by endoglin. A, Endoglin expression varies across endoglin variant clonal cell lines. Representative photomicrographs are depicted of endoglin clonal variant cells stained by immunohistochemistry, using endoglin or isotype control antibody (100× magnification). B, C, Endoglin suppresses cell invasion. A Boyden chamber assay was used to assess the invasive activity of cells. Data are the mean±S.E.M. percent of invading vector control (VC) cells for a single experiment, run in replicates of N=4. Similar results were seen in a separate experiment run at a separate time, also N=4. * denotes P≤0.05 compared to VC. In B, individual cell lines clones were evaluated. In C, equal numbers of NO-ENG1 and NO-ENG2 cells were combined to form NO-ENG cells, and equal numbers of HI-ENG1 and HI-ENG2 cells were combined to form HI-ENG cells.

Studies began with individual cell line clones, engineered to express different levels of endoglin (Liu et al. (2002) Oncogene 21:8272-8281; herein incorporated by reference in its entirety). Because endoglin is a cell surface protein, detection was sought on the surface of cells by immunohistochemical staining without cell permeabilization. HI-ENG1 and HI-ENG2 cells were thereby shown to express high levels of endoglin, VC cells low but detectable levels, while NO-ENG1 and NO-ENG2 cells expressed no detectable cell surface endoglin, and looked identical to isotype antibody stained negative control cells, FIG. 20.

Compared to VC cells, HI-ENG1 and HI-ENG2 cells both invaded significantly less, while NO-ENG1 and NO-ENG2 cells both invaded significantly more (Student's t test p≤0.05), FIG. 20B. Because testing a single clone may yield spurious results, and because multiple clones are seen in metastatic PCa lesions in man (Rubin et al. (2000) Clin. Cancer Res. 6:1038-1045; herein incorporated by reference in its entirety), for animal studies the two high endoglin cell lines were combined just before each experiment, as were the two no endoglin cell lines. VC cells were already polyclonal. The resultant HI-ENG and NO-ENG cells exhibited significantly lower and higher invasion, respectively, compared to VC cells (Student's t test p≤0.05), FIG. 20C.

Endoglin Suppresses Human Prostate Cancer Metastasis

Figure 21:
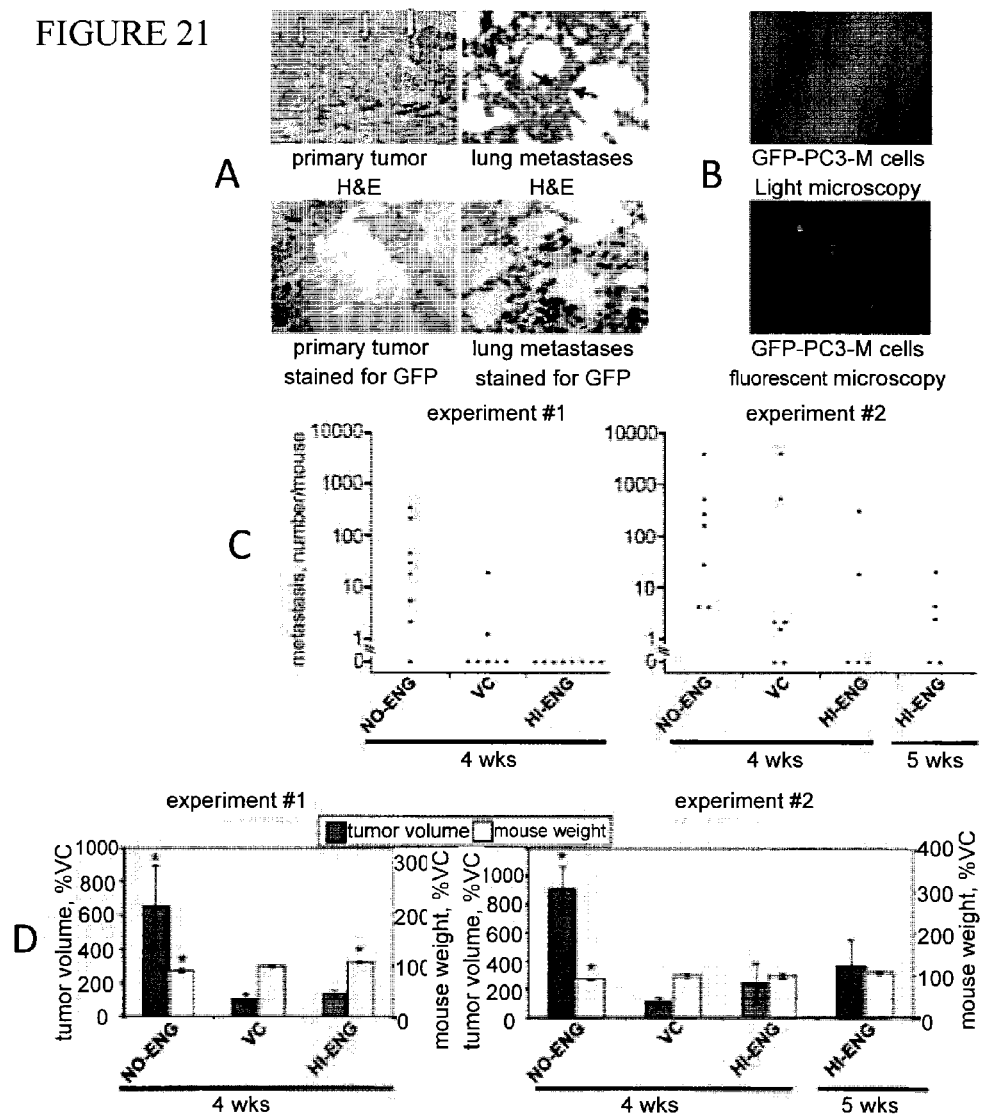
FIG. 21 shows suppression of human prostate cancer cell metastasis and tumor growth by endoglin. Mice were orthotopically implanted with the indicated endoglin variant cell line, and 4 to 5 weeks after implantation, tumor size and metastasis was assessed. A, Representative photomicrographs of H&E stained and immunostained (for GFP) primary tumor (white arrows) and metastatic human PCa cells in lung tissue (black arrows). B, Representative photomicrographs of PC3-M-GFP cells growing in cell culture, prior to implantation. C, Endoglin suppresses metastasis. Data represent the number of lung metastasis per mouse 4 to 5 weeks after implantation, as indicated. Each graph depicts results from a separate experiment, conducted at a separate time. D, Endoglin suppresses tumor growth. Data are the mean±S.E.M. tumor volume and mouse weight, as indicated. * denotes P≤0.05 compared to VC.

To determine whether endoglin could suppress human PCa metastasis, mice were orthotopically implanted with HI-ENG, NO-ENG, or with VC cells. Four weeks later, the number of lung metastases, tumor volume, and animal weight were measured. Representative photomicrographs of H&E stained primary tumor and metastatic lung deposits are depicted in FIG. 21A. The characteristically large PC3-M cells and nuclei (black arrow) allowed for easy detection by histomorphologic examination of H&E stained lung tissue. In separate studies mice were implanted with PC3-M-GFP cells, allowing their identity to be confirmed by immuno-staining for green fluorescent protein (GFP), FIGS. 21A and B. Metastases were quantified by histomorphologic examination of H&E stained tissue.

Eight mice per cohort were implanted with a given endoglin variant cell type. One VC implanted mouse died in the perioperative period. The number of mice developing lung metastasis and the number per mouse is depicted in FIG. 21C. Considering data from all three cohorts demonstrates that endoglin significantly suppressed the formation of metastases (Chi-squared p value<0.001). For NO-ENG, VC, and HI-ENG cohorts, the percentage of mice with metastasis was 88, 29, and 0%, respectively. Further, for mice with metastases, the mean number of metastases per mouse was 94, 9, and 0, respectively. Compared to the NO-ENG cohort, the decrease in metastases was significant for the HI-ENG cohort (Fisher's Exact Test p value=0.05), but not for the VC cohort (p value=0.46). Tumor volume did not differ significantly between VC and HI-ENG cohorts, but mean tumor volume was 6.5 fold higher in the NO-ENG as compared the VC cohort (Student's t test p=0.05), FIG. 21D. Body weight was 9% lower in the NO-ENG cohort, and 9% higher in the HI-ENG cohort, compared to the VC cohort (Student's t test p≤0.05 for both), FIG. 21D.

Therefore, experiments conducted during the course of developing some embodiments for the present invention show that endoglin can suppress metastasis. They also show that tumor growth is enhanced when endoglin is at very low levels. These findings were substantiated by conducting an expanded repeat experiment, wherein a forth cohort was included in which mice were implanted with HI-ENG cells, but were maintained for an additional week (e.g., for 5 weeks). It had previously been demonstrated that increased incubation time correlated with increased metastases in this model (Lakshman et al. (2008) Cancer Res. 68:2024-2032; herein incorporated by reference in its entirety). Thus, the HI-ENG×5 week cohort provided a measure of endoglin's ability to suppress metastasis under conditions that fostered increased metastasis. Only HI-ENG cell implanted mice were maintained for 5 weeks; beyond 4 weeks systemic cancer impacts animal health in other cohorts. In the additional experiment, 7 mice were implanted per cohort. Two mice each in the HI-ENG and HI-ENG×5 wks cohorts died in the perioperative period.

While more metastases were observed across all cohorts compared to experiment #1, FIGS. 21C and D, the findings of the additional experiment were similar. Specifically, a consideration of data from the NO-ENG, VC, and HI-ENG 4 week cohorts demonstrated that endoglin significantly suppressed the formation of metastasis (Chi-squared p value=0.02). For NO-ENG, VC, and HI-ENG cohorts, the percentage of mice with lung metastasis was 100, 71, and 40%, and for those with metastases, the mean number per mouse was 347, 402, and 193, respectively. Compared to the NO-ENG cohort, metastases were significantly decreased in HI-ENG and VC cohorts (Fisher's Exact Test p values<0.001 and 0.03, respectively). Tumor volume did not differ significantly between VC and HI-ENG cohorts, but was 9-fold higher in the NO-ENG as compared the VC cohort (t test p value=0.002), FIG. 21D. Body weight was significantly lower in the NO-ENG cohort by 8% (t test p value<0.05), and non-significantly higher in the HI-ENG as compared to the VC cohort, FIG. 21D.

Additional findings related to the HI-ENG×5 wks cohort. Tumor growth continued during the additional week of incubation, giving a mean tumor volume 1.5 fold greater than the HI-ENG X 4 wks cohort (not statistically significant). Despite the extended incubation time and tumor growth, only 60% of mice had metastasis, and for those with metastasis the mean number per mouse was only 15. These values did not differ significantly from the respective values of 40% and 193 observed in the HI-ENG X 4 wks cohort. Finally, the weight of the HI-ENG X 5 wks cohort did not differ from that of either VC or HI-ENG X 4 wks cohorts.

Endoglin Suppresses Viable Prostate Cancer Cells in the Blood

The number of viable PCa cells in the blood at 4 weeks was determined in both experiments. Considering data from all mice, endoglin significantly suppressed circulating viable PCa cells (Fisher's exact p-value=0.015), FIG. 22A. The difference between NO-ENG and HI-ENG mice was significant (p=0.01). Circulating viable PCa cells were present in 45, 22, and 0% of NO-ENG, VC, and HI-ENG mice, respectively. The mean number of colonies/mouse/cc blood, for those with circulating cells, was 124, 6, and N/A, respectively.

Figure 22:
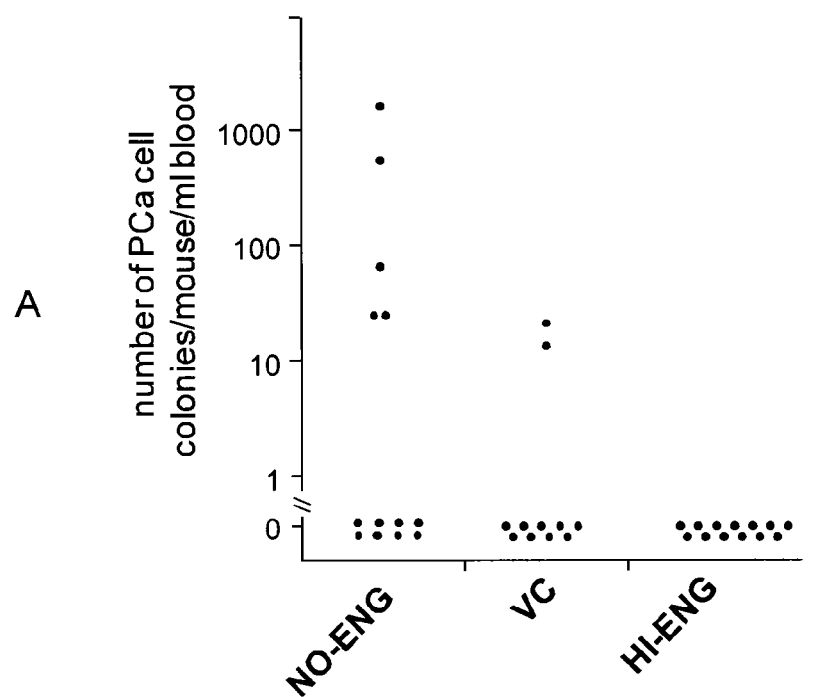
FIG. 22 shows that endoglin suppresses viable PCa cells in the blood. A, At 4 weeks after implantation of the indicated cell line, the number of viable PCa cells in the blood was measured. Data are the number of colonies per ml blood, for each mouse where at least 100 µl blood could be harvested. B, Colonies are of human origin. Representative photomicrographs of GFP positive and negative cell colonies are depicted.
Figure 22:
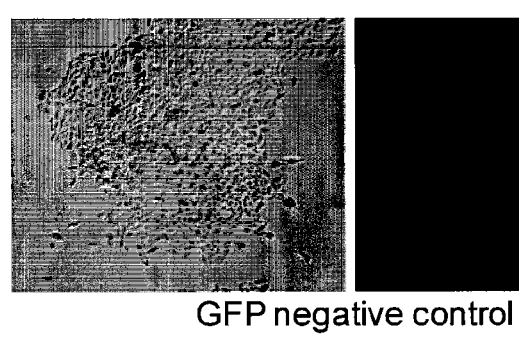

Colonies arising from the blood were of human cell origin. All emergent colonies contained GFP as assessed by fluorescent microscopy. FIG. 22B depicts a typical PC3-M-GFP cell colony. Cells lacking GFP do not fluoresce, FIG. 22B.

Loss of Endoglin Increases Cell Proliferation

Having shown that complete loss of endoglin increased tumor size, a series of studies were conducted to evaluate the underlying mechanism. Ki67 increases in proliferating human PCa cells, and increased Ki67 is a poor prognostic marker in men with PCa (Pollack et al. (2004) J. Clin. Oncol. 22:2133-2140; Inoue et al. (2005) Urology 66:332-337; Bubendorf et al. (1996) 178:437-441; each herein incorporated by reference in its entirety). Tumor tissue was stained for Ki67, FIG. 23A, and quantified, FIG. 23B. Ki67 was 2.3 fold higher in NO-ENG compared to VC mice (t-test p-value=0.008), but did not differ between VC and HI-ENG mice.

Figure 24:
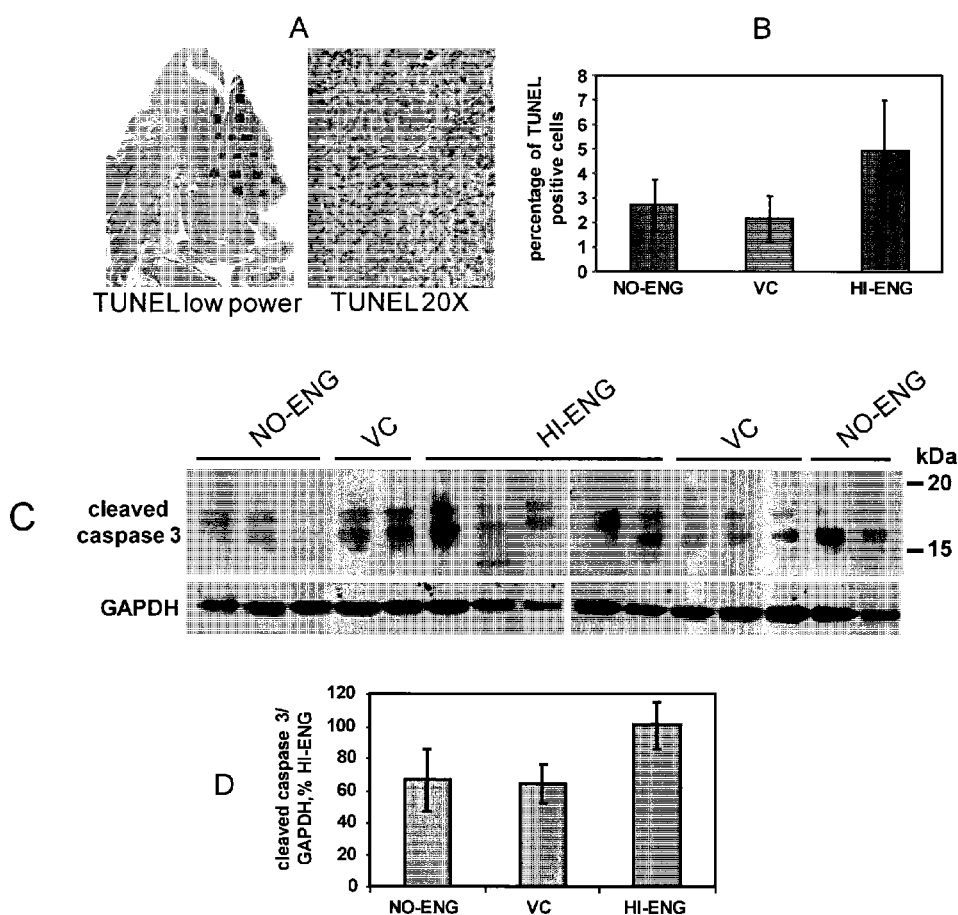
FIG. 24 shows that increased tumor growth is not associated with increased apoptosis. A, Representative photomicrographs of TUNEL stained tissue at low and high magnification, with ROIs denoted. B, TUNEL index is not increased in NO-ENG tumor bearing mice. Data are the mean±S.E.M. TUNEL index for all mice in the indicated cohorts. C, D, Cleaved caspase 3 is not increased in NO-ENG tumor bearing mice. Western blot of tumor tissue protein is depicted in C, and mean±S.E.M. of quantified bands is graphically depicted in D.

Ki67 findings indicate that complete loss of endoglin increases cell proliferation. It was next shown that this was not associated with decreased cell death. TUNEL staining of tumor tissue revealed no increase in staining in NO-ENG compared to VC tissue, FIGS. 24A and B. Interestingly, TUNEL staining was 2.3 fold higher in HI-ENG, compared to VC tissue. While this increase was not significant, and tumor size did not differ between these two cohorts, substantiation of this finding was sought. Measurement of cleaved caspase 3 protein levels in tumor tissue by Western blot demonstrated no differences amongst the three cohorts of mice, FIGS. 24C and D.

While the present invention is not limited to any particular mechanism, and an understanding of the mechanism is not necessary to practice the present invention, it is contemplated that endoglin affects two cellular processes: metastasis and tumor growth. If metastasis was simply driven by increased tumor size, then tumor volume should correlate with the number of metastases in a given mouse. A demonstration that this was not the situation was determined by comparing tumor volume and number of metastases for all mice at the 4 week time point. The resultant Spearman correlation coefficient, R, for NO-ENG, VC, and HI-ENG cohorts was −0.22, −0.24, and −0.35, respectively. For all mice in all cohorts considered together, R was −0.11.

Loss of Endoglin Results in Selective Loss of TGFβ Signaling

Endoglin can bind TGFβ (Barabara et al. (1999) J. Biol. Chem. 274:584-594; herein incorporated by reference in its entirety), TGFβ regulates PCa cell proliferation (Rohlff et al. (1998) Prostate 37:51-59; herein incorporated by reference in its entirety), and findings described herein show that endoglin status can affect cell proliferation. While the present invention is not limited to any particular mechanism, and an understanding of the mechanism is not necessary to practice the present invention, it was contemplated that endoglin loss decreased TGFβ signaling, thus allowing increased cell proliferation in NO-ENG cells. In several cell types, including human PCa, TGFβ increases expression of the cell cycle inhibitory protein, $p21^{waf1/cip1}$, induces cell cycle arrest, and inhibits cell proliferation (Rohlff et al. (1998) Prostate 37:51-59; herein incorporated by reference in its entirety). However, $p21^{waf1/cip1}$ protein expression in tumor tissue was not affected by endoglin expression status, FIGS. 23C and D.

Figure 23:
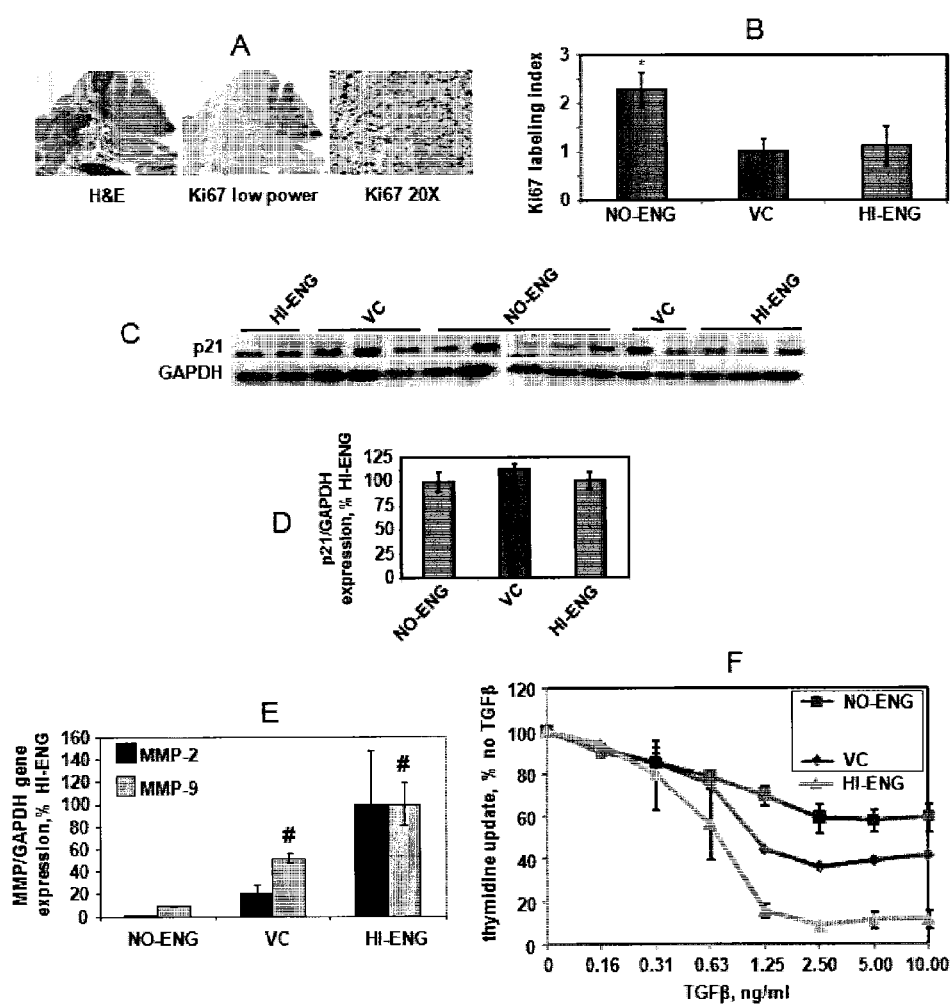
FIG. 23 shows that increased tumor growth is associated with increased cell proliferation and changes in TGFβ signaling. A, Representative photomicrographs of H&E and Ki67 stained tumor tissue under low magnification, with prospectively selected regions of interest (ROIs) denoted, and a high magnification photomicrograph of Ki67 stained cells in tissue. B, Ki67 labeling index is increased in NO-ENG tumor cells. Data are the mean±S.E.M. Ki67 labeling index for all mice in the indicated cohorts at 4 weeks. C, D, p21waf1/cip1 is not altered by endoglin. Western blot of protein extracted from tumor tissue is depicted in C, and mean±S.E.M. of quantified bands is graphically depicted D. * denotes P≤0.05 compared to VC. E, Loss of endoglin decreases MMP-2 and MMP-9 gene expression. Data are the mean±SD (N=2) level of gene expression in tumor tissue measured by qRT/PCR; similar results were seen in multiple replicate experiments (also N=2). # denotes P≤0.05 compared to NO-ENG tumor bearing mice. F, Loss of TGFβ-mediated growth inhibition is seen with loss of endoglin. Data are the mean±S.E.M. thymidine uptake, expressed as a percentage of non-TGFβ treated cells, of a single experiment performed in replicates of N=3; similar results were seen in a separate experiment (also N=3).

Though $p21^{waf1/cip1}$ findings suggest that endoglin does not regulate TGFβ signaling, the possibility of selective signaling was investigated. Both matrix metalloproteinase 2 (MMP-2) and MMP-9 are TGFβ-responsive genes in human PCa, including PC3-M cells, both increase cell invasion, and both are expressed at high levels in invasive PCa lesions in man (Wood et al. (1997) Clin. Exp. Metastasis 15:246-258; Huang et al. (2005) 65:3470-3478; each herein incorporated by reference in its entirety). As shown in FIG. 23E, loss of endoglin decreased the mean expression of both MMP-2 and MMP-9, consistent with selective loss of TGFβ signaling. Considering all three cohorts of mice, the MMP-9 decrease was significant (one way ANOVA p<0.001), while MMP-2 only trended downwards (p=0.24). Compared to NO-ENG mice, MMP-9 was significantly higher in VC and HI-ENG mice (2 sided t test p values 0.001 and 0.01, respectively), while MMP-2 increases only represented a trend (0.32 and 0.16). To provide more substantive evidence that loss of endoglin leads to loss of TGFβ signaling, HI-ENG, VC, and NO-ENG cells were treated with increasing concentrations of TGFβ, and thymidine uptake was measured. With progressive loss of endoglin, there was a progressive loss of TGFβ sensitivity, FIG. 23E.

Endoglin Increases Expression of Smad1 Responsive Genes

Figure 25:
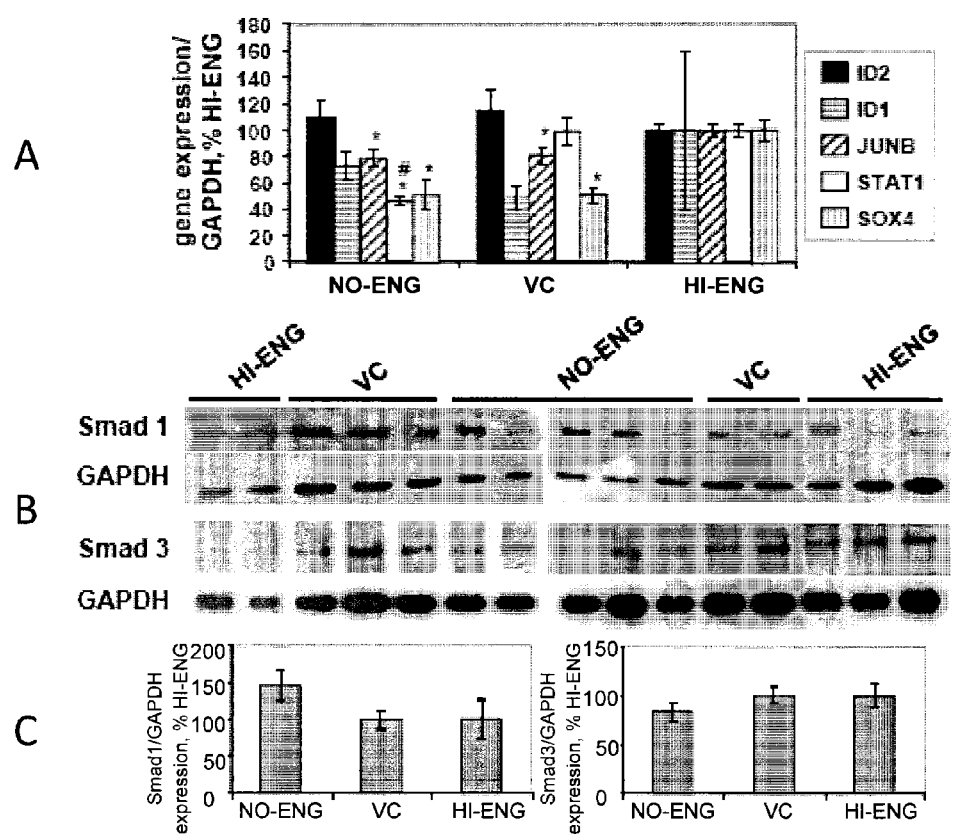
FIG. 25 shows that endoglin increases the expression of Smad1 responsive genes. A, Loss of endoglin decreases the expression of Smad1 responsive genes in mice. The expression of the indicated Smad1 responsive genes was measured in tumor tissue from the indicated cohorts of mice by qRT/PCR. Data are the mean±S.E.M. of a single experiment for all mice in the indicated cohort, run in replicates of N=2 for each mouse, and repeated at a separate time, also in replicates of N=2. * and # denote P≤0.05 compared to HI-ENG and VC cohorts, respectively. B, C, Endoglin does not alter Smad1 or Smad3 protein expression in mice. Western blot of tumor tissue protein is depicted in B, and mean±S.E.M. of quantified bands is graphically depicted C.

Endoglin inhibits cell invasion by activating the bone morphogenetic protein (BMP) responsive Smad, Smad1 (Craft et al. (2007) Oncogene 26:7240-7250; herein incorporated by reference in its entirety). The involvement of endoglin in activation Smad1 in tumor tissue was investigated. Because intrinsically high levels of prostatic acid phosphatase preclude an accurate measurement of phospho-Smad1 levels in tissue (Craft et al. (2007) Oncogene 26:7240-7250; herein incorporated by reference in its entirety), endoglin's effects upon the expression of known BMP and Smad1 responsive genes, SOX4, STAT1, JUNB, ID1 and ID2 (Ota et al. (2002) J. Cell Physiol. 193:299-318; Locklin et al. (2001) J. Bone Miner. Res. (2001) 16:2192-2204; each herein incorporated by reference in its entirety), were measured by qRT/PCR, FIG. 25A. With endoglin loss, JUNB, STAT1, and SOX4 expression significantly decreased (1-way ANOVA p=0.04, <0.001 and 0.002, respectively), while ID1 and ID2 were unaffected. If endoglin was activating Smad1, then total Smad protein levels should be constant. This was shown to be the situation by measuring Smad1 and Smad3 in tumor tissue, FIGS. 25B and C.

In experiments conducted during the course of developing some embodiments of the present invention, it was shown that endoglin suppresses cancer metastasis. This was demonstrated for the particular case of human PCa. With progressive loss of endoglin, a progressive increase in metastasis was observed. Metastasis to the bone is a dominant clinical feature of PCa (Zelefsky et al. (2008) CANCER: Principles and Practice of Oncology 1392-1462, New York, Lippincott Williams & Walkins; herein incorporated by reference in its entirety), however, metastasis to the bone was not a feature of the murine model described herein. However, it is important to consider that autopsy studies demonstrate that PCa metastases are in fact wide spread to organs throughout the body (Rubin et al. (2000) Clin. Cancer Res. 6:1038-1045; herein incorporated by reference in its entirety). Therefore, proteins that inhibit initial steps in the metastatic cascade, such as invasion out of the primary organ, are of particular importance because they preclude the development of later steps, no matter what the end organ is. Because endoglin suppressed PCa cell invasion (Liu et al. (2002) Oncogene 21:8272-8281; herein incorporated by reference in its entirety), including in early transformed prostate cell phenotypes (Craft et al. (2007) Oncogene 26:7240-7250; herein incorporated by reference in its entirety), it was hypothesized that endoglin would suppress metastasis, and that effects would be evident at initial steps in the metastatic cascade. To test this hypothesis a model was employed that specifically tests action at initial steps in the metastatic cascade, including inhibition of invasion (Lakshman et al. (2008) Cancer Res. 68:2024-2032; herein incorporated by reference in its entirety). In experiments described herein, it was shown that endoglin decreased the number of circulating PCa cells in the blood, thereby demonstrating activity at early steps in the metastatic cascade. Passage through the blood represents a middle step in the movement of cancer cells from their primary organ of origin to a distant organ (Ruoslahti (1996) Sci. Am. 275:27-77; herein incorporated by reference in its entirety). The presence of cancer cells, including PCa, in the blood is increasingly being evaluated clinically as a marker of future development of metastasis (Goodman et al. (2009) Cancer Epidemiol. Biomarkers Prev. 18:1904-1913; Kasimir-Bauer (2009) Mol. Diagn. Ther. 13:209-215; Helo et al. (2009) Clin. Chem. 55:765-773; Sastre et al. (2008) Ann. Oncol. 19:935-938; each herein incorporated by reference in its entirety).

Experiments described herein showed that endoglin suppresses human PCa tumor growth. Further, it was demonstrated that this was due to changes in cell proliferation, as assessed by Ki67 expression. Ki67 is an established indicator of human PCa cell proliferation, and a poor prognostic marker in men with PCa (Pollack et al. (2004) J. Clin. Oncol. 22:2133-2140; Inoue et al. (2005) Uriology 66:332-337; Bubendorf et al. (1996) J. Pathol. 178:437-441; each herein incorporated by reference in its entirety). While the present invention is not limited to any particular mechanism, and an understanding of the mechanism is not necessary to practice the present invention, it is contemplated that endoglin regulates the growth of cells in tumor tissue directly such that that loss of endoglin leads to a loss of TGFβ-mediated inhibition of cell proliferation. The likelihood that this mechanism is operative in tumor tissue is also supported by that fact that TGFβ is ubiquitous in tissue and is an important regulator of human PCa cell proliferation (Rohlff et al. (1998) Prostate 37:51-59; herein incorporated by reference in its entirety). While the present invention is not limited to any particular mechanism, and an understanding of the mechanism is not necessary to practice the present invention, it is contemplated that the role of increased cell proliferation as the cause of increased tumor growth is further supported by the fact that neither TUNEL nor cleaved caspase 3, both measures of apoptosis, were decreased in NO-ENG mice.

Notably, increased tumor size in mice was only observed in the NO-ENG cohort, where endoglin levels were undetectable. However, in cell culture-based studies there was a progressive loss of TGFβ-mediated suppression of cell proliferation with progressive loss of endoglin expression, seen across HI-ENG, VC and NO-ENG cells. These findings highlight the importance of examining endoglin biology in vivo. They also demonstrate that there are regulatory factors present in tissue that are not present under in vitro cell culture conditions. While the present invention is not limited to any particular mechanism, and an understanding of the mechanism is not necessary to practice the present invention, it is contemplated that endoglin loss decreased the expression of the TGFβ-responsive genes, MMP-2 and -9, but did not decrease expression of the TGFβ-inducible protein, $p21^{waf1/cip1}$, in tumor. In tissue culture, TGFβ induces both MMP-2 and $-9^{28}$, as well as $p21^{waf1/cip1}$ (Rohlff et al. (1998) Prostate 37:51-59; herein incorporated by reference in its entirety).

Together, while the present invention is not limited to any particular mechanism, and an understanding of the mechanism is not necessary to practice the present invention, it is contemplated that endoglin's regulation of metastasis is separate from its regulation of tumor growth. This is highlighted by the fact that HI-ENG and VC mice have identical tumor size, while the latter have increased metastases. Also, within individual cohorts, tumor size did not correlate with metastasis. While the present invention is not limited to any particular mechanism, and an understanding of the mechanism is not necessary to practice the present invention, it is contemplated that differential regulation of separate cellular functions likely relates to the fact that endoglin regulates different TGFβ superfamily signaling pathways.

Figure 26:
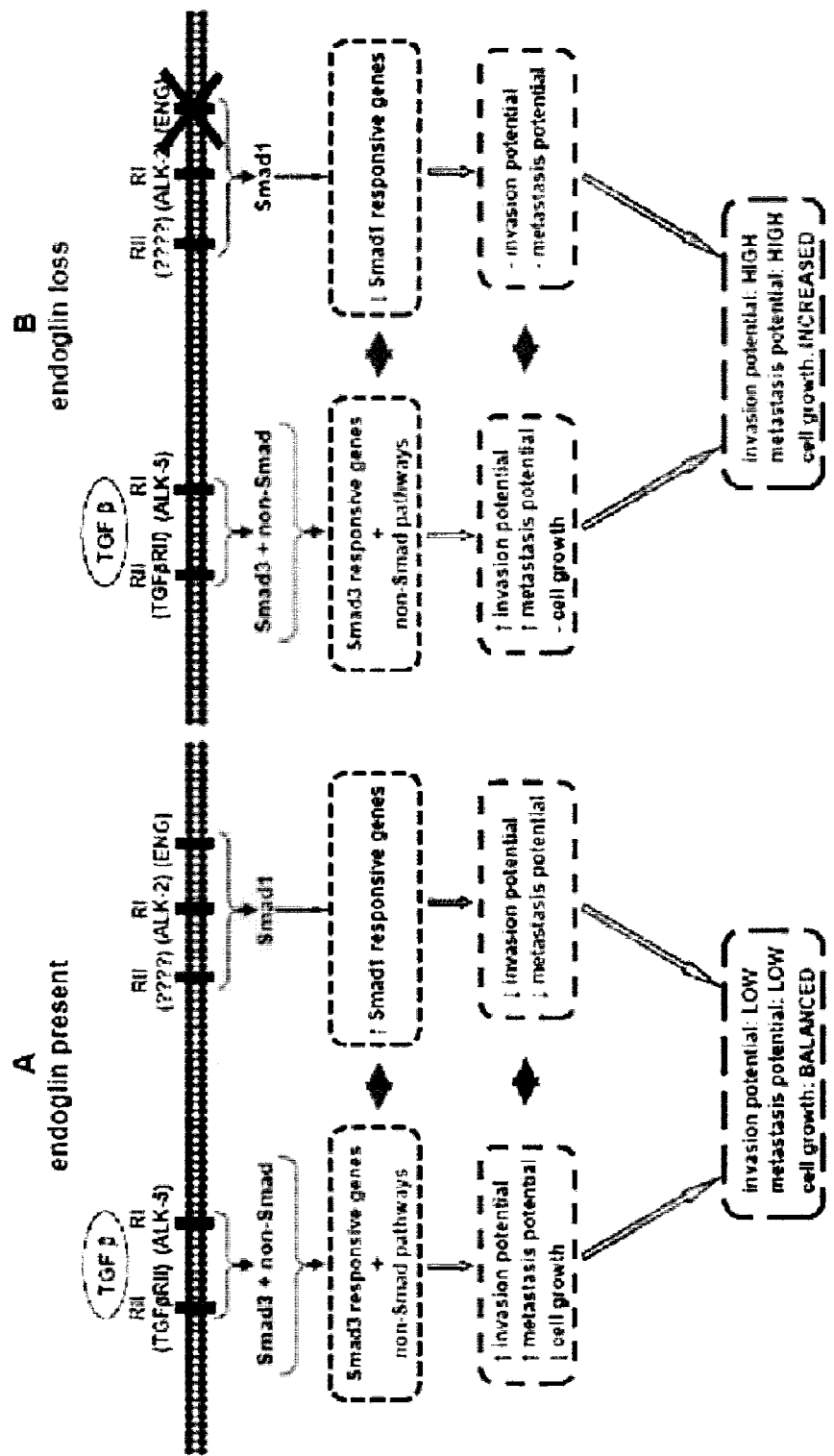
FIG. 26 shows a model of endoglin mediated regulation of metastatic potential and cell growth. A, Endoglin present. Transforming growth factor β (TGFβ) activates Smad3 and other TGFβ-responsive elements to stimulate cell invasion, thus increasing metastatic potential, and to inhibit cell growth. Counterbalancing this, endoglin-mediated Smad1 activation inhibits cell invasion, thus diminishing metastatic potential. Cell based integration of signals results in a phenotype characterized by low invasion, low metastatic potential, and controlled cell growth. B, Endoglin loss. With cancer progression, endoglin is lost. This decreases Smad1-mediated suppression of invasion and metastasis, and causes loss of TGFβ-mediated growth inhibition. Integration of signals results in a phenotype characterized by high invasion, high metastatic potential, and high cell growth. ↓=inhibition of individual cellular and systemic processes; ↑=stimulation of individual cellular and systemic processes; TGFβ=transforming growth factor β; TGFβRI and TGFβRII=type I and II TGFβ receptor; ALK=activin-like kinase receptor; ENG=endoglin.

Data presented herein support the model outlined in FIG. 26. Under the influence of TGFβ/Smad3, cell invasion is stimulated, thus increasing metastatic potential, and cell growth is inhibited. Counterbalancing this, endoglin-mediated Smad1 activation inhibits cell invasion, thus diminishing metastatic potential. Cell based integration of signals results in a phenotype characterized by low invasion, low metastatic potential, and controlled cell growth. However, loss of endoglin with cancer progression decreases Smad1-mediated suppression of invasion and metastasis, and causes loss of TGFβ-mediated growth inhibition. Integration of signals results in a phenotype characterized by high invasion, high metastatic potential, and high cell growth.

While data presented herein would appear to contradict reports that link endoglin expression to cancer progression, in fact they do not. It is important to realize that endoglin is expressed at high levels by endothelial cells (Cheifetz et al. (1992) J. Biol. Chem. 267:19027-19030; herein incorporated by reference in its entirety). With cancer-associated angiogenesis, endothelial cells increase, and therefore so does endoglin (Bertolino et al. (2005) Chest 128 (6 Suppl.):585S-590S; herein incorporated by reference in its entirety). Specifically, blood levels of circulating endoglin have been identified as a marker of angiogenesis and tumor burden, and a poor prognostic indicator Mysliwiec et al. (2008) Folia Histochem. Cytobiol. 46:487-492; Vo et al. (2008) Breast Cancer Res. Treat. DOI: 10.1007/s10549-008-0261-5; Fujita et al. (2009) Int. J. Cancer 124:664-669; Takahashi et al. (2001) Clin. Cancer Res. 7:524-532; each herein incorporated by reference in its entirety). Anti-endoglin antibody inhibits angiogenesis, thereby blocking tumor growth and metastasis (Uneda et al. (2009) Int. J. Cancer 125:1446-1453; herein incorporated by reference in its entirety). While the present invention is not limited to any particular mechanism, and an understanding of the mechanism is not necessary to practice the present invention, it is contemplated that in endothelial cells, endoglin enhances angiogenesis and cancer progression. In contrast, in epithelial cells, endoglin suppresses cancer progression.

Endoglin suppresses invasion and colony formation in esophageal epithelial cells (Wong et al. (2008) 123:2816-2823; herein incorporated by reference in its entirety) and suppresses cancer formation in skin epithelial cells (Perez-Gomez et al. (2007) Cancer Res. 67:10268-10277; herein incorporated by reference in its entirety. Additionally, endoglin suppresses PCa cell invasion (Liu et al. (2002) Oncogene 21:8272-8281; Craft et al. (2007) Oncogene 26:7240-4250; each herein incorporated by reference in its entirety). Interestingly, in breast epithelial cells, endoglin enhances invasion (Oxmann et al. (2008) Oncogene 27:3567-3575; herein incorporated by reference in its entirety), suggesting that it may have altered function in different cell types. In fact, demonstration of this occurs at the molecular level in that, in PCa cells, endoglin cooperated with the ALK2 type I receptor subtype to activate Smad1 (Craft et al. (2007) Oncogene 26:7240-4250; herein incorporated by reference in its entirety), whereas in endothelial cells, endoglin cooperates with ALK1 (Blanco et al. (2005) J. Cell Physiol. 204:574-587; Lebrin et al. (2004) EMBO J. 23:4018-4028; each herein incorporated by reference in its entirety).

In experiments presented herein, it is shown that endoglin suppresses cancer metastasis, and that this was associated with decreased expression in several Smad1-responsive genes examined. Endoglin acted at early steps in the metastatic cascade. This resulted in a decrease in circulating cancer cells in the blood. While the present invention is not limited to any particular mechanism, and an understanding of the mechanism is not necessary to practice the present invention, it is contemplated that a progressive loss of endoglin led to a progressive increase in metastasis, supporting the notion that loss of endoglin expression in man imparts a continuum of risk across a spectrum of expression. This notion is further supported by studies in which loss of endoglin expression was demonstrated during human PCa cell progression (Liu et al. (2002) Oncogene 21:8272-8281; herein incorporated by reference in its entirety). In those studies parental and more advanced cell type pairs from several different patients were examined, demonstrating lower endoglin expression with PCa progression in each instance. While the present invention is not limited to any particular mechanism, and an understanding of the mechanism is not necessary to practice the present invention, it is contemplated that endoglin suppressed human PCa tumor growth. Growth suppression was not continuous, and was only lost when endoglin expression was undetectable. Therefore, there is a threshold level of endoglin expression in man below which tumor growth in enhanced. While the present invention is not limited to any particular mechanism, and an understanding of the mechanism is not necessary to practice the present invention, it is contemplated that the loss of TGFβ's ability to suppress PCa cell growth in vitro when endoglin was lost is a mechanism by which endoglin suppressed tumor growth in vivo. Endoglin's affect upon TGFβ signaling became more complex in the in vivo situation, reflecting the more complex environment of tumor as compared to cell culture.

Example 15

Short-Term Animal Toxicity Studies with Compound 46

Short-term animal toxicity studies were conducted with compound 46, and there was no evidence of toxicity. Six week old athymic male mice were dosed by oral gavage with 0.15, 1.5, 15, or 150 mg KBU2046/kg body weight/day, or vehicle control, daily for 5 days. There were 3 mice per dose level. No adverse effects on behavior, food consumption, or continued weight gain were observed.

Example 16

Scaled-Up Production of Compound 46 and Stability Studies

Successful scale-up of synthesis of compound 46 was conducted according to the methods of Examples 7, 11, and the Detailed Description, yielding 10 g of material that is >98% pure (by HPLC). Compound stability was documented after exposure to 40 kGy of radiation (the level used to sterilize chow) and after exposure to high temperatures and pressures (i.e., autoclaving).

Pure R and S enantiomers of compound 46 have been synthesized, and it has been demonstrated that they do not undergo epimerization (as assayed by HPLC with chiral stationary phase), even when incubated at 37° C.

We claim:
1. A compound having the formula:

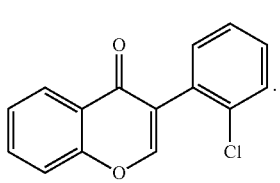 [SMILES: O=c1c(-c2ccccc2Cl)coc2ccccc12]

2. A pharmaceutical composition comprising the compound of claim 1.
3. A compound having the formula:

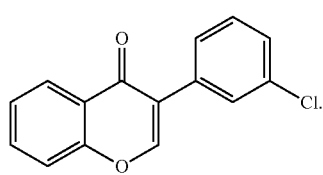 [SMILES: O=c1c(-c2cccc(Cl)c2)coc2ccccc12]

4. A pharmaceutical composition comprising the compound of claim 3.
5. A compound having the formula:

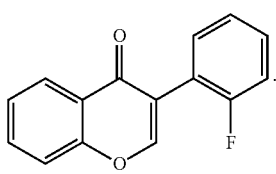

6. A pharmaceutical composition comprising the compound of claim 5.
7. A compound having the formula:

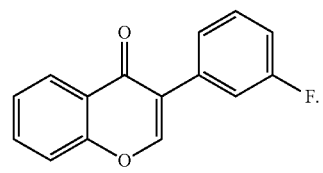 [SMILES: O=c1c(-c2cccc(F)c2)coc2ccccc12]

8. A pharmaceutical composition comprising the compound of claim 7.

9. A compound having the formula:

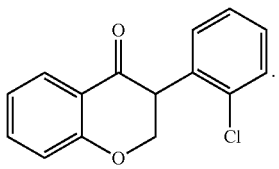

10. A pharmaceutical composition comprising the compound of claim 9.
11. A compound having the formula:

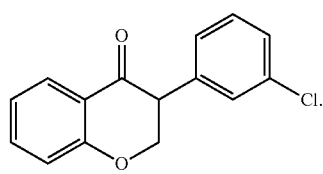 [SMILES: O=C1c2ccccc2OCC1c1cccc(Cl)c1]

12. A pharmaceutical composition comprising the compound of claim 11.
13. A compound having the formula:

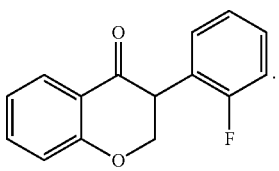 [SMILES: O=C1c2ccccc2OCC1c1ccccc1F]

14. A pharmaceutical composition comprising the compound of claim 13.
15. A compound having the formula:

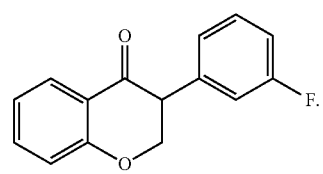 [SMILES: O=C1c2ccccc2OCC1c1cccc(F)c1]

16. A pharmaceutical composition comprising the compound of claim 15.

* * * * *

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1 ttcctcctttt gtctcccagc                                                     20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
attcctcctt tgtctcccag                                                      20

<210> SEQ ID NO 3
<211> LENGTH: 19
<212> TYPE: DNA
<213> ORGANISM: Artificial Sequence
<220> FEATURE:
<223> OTHER INFORMATION: Synthetic

<400> SEQUENCE: 3
attcctcctt tgtctccca                                                       19

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
gcctctttat cacctaccac a                                                    21

<210> SEQ ID NO 5
<211> LENGTH: 20
<212> TYPE: DNA
```

```
<213> ORGANISM: Artificial Sequence
<220> FEATURE:
<223> OTHER INFORMATION: Synthetic

<400> SEQUENCE: 5
aauuccucct ttgtcuccca                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
gucuctctat gtgtgggsuuu                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
ugugugttct cagtcucucu                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
cuccucgtcc aatttcucca                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
ggcuugctgt ggtcgaaggc                                               20
```